United States Patent
Goertz et al.

(10) Patent No.: US 9,795,135 B2
(45) Date of Patent: Oct. 24, 2017

(54) BINARY FUNGICIDAL COMPOSITION

(71) Applicant: BAYER CORPSCIENCE AKTIENGESELLSCHAFT, Monheim (DE)

(72) Inventors: Andreas Goertz, Gold River, CA (US); Mazen Es-Sayed, Langenfeld (DE)

(73) Assignee: BAYER CROPSCIENCE AKTIENGESELLSCHAFT, Monheim am Rhein (DE)

(*) Notice: Subject to any disclaimer, the term of this patent is extended or adjusted under 35 U.S.C. 154(b) by 0 days.

(21) Appl. No.: 14/907,219

(22) PCT Filed: Jul. 23, 2014

(86) PCT No.: PCT/EP2014/065770
§ 371 (c)(1),
(2) Date: Jan. 22, 2016

(87) PCT Pub. No.: WO2015/011166
PCT Pub. Date: Jan. 29, 2015

(65) Prior Publication Data
US 2016/0165889 A1    Jun. 16, 2016

(30) Foreign Application Priority Data
Jul. 24, 2013  (EP) .................................... 13177742

(51) Int. Cl.
*A01N 63/00*  (2006.01)
*A01N 43/42*  (2006.01)

(52) U.S. Cl.
CPC ............. *A01N 43/42* (2013.01); *A01N 63/00* (2013.01)

(58) Field of Classification Search
None
See application file for complete search history.

(56) References Cited

U.S. PATENT DOCUMENTS

| | | | |
|---|---|---|---|
| 5,215,747 A | 6/1993 | Hairston et al. | |
| 5,766,583 A * | 6/1998 | Luth | C12R 1/645 424/93.5 |

FOREIGN PATENT DOCUMENTS

| | | | | |
|---|---|---|---|---|
| DE | WO 2009037242 A2 * | 3/2009 | ............. | A01N 63/02 |
| EP | 1736471 A1 | 12/2006 | | |
| EP | 2517562 A1 | 10/2012 | | |
| JP | 2007217353 A | 8/2007 | | |
| JP | 20071944 A | 7/2008 | | |
| WO | WO 9850422 A1 * | 11/1998 | ............. | A01N 63/00 |
| WO | 2005070917 A1 | 8/2005 | | |
| WO | 2007011022 A1 | 1/2007 | | |
| WO | 2011077514 A1 | 6/2011 | | |

OTHER PUBLICATIONS

Gisi, Ulrich; "Synergistic Interactions of Fungicides in Mixtures" Phytopathology, 86, 1273-1279, 1996.*
International Search Report from corresponding PCT/EP2014/067705463, dated Jan. 9, 2014.
Adwinckle et al., "Evaluation of control tire blight infection of apple blossoms and shoots with SAR inducer, biological agents, a growth regulator, copper compounds, and other materials." Acta Horticulturae, vol. 590, (2002), pp. 325-331, XP0091741889561.
Thomas D. Flanagan. "Preparative Biochemistry", Molecular Biology. (1988) vol. 18: 377-378.

* cited by examiner

*Primary Examiner* — David Berke-Schlessel
(74) *Attorney, Agent, or Firm* — McBee Moore Woodward & Vanik IP, LLC; Susan McBee; David Woodward

(57) ABSTRACT

The present invention relates to novel compositions and/or formulations, to a process for preparing these compositions and/or formulations and to the use thereof as biologically active compositions and biologically active compositions and/or formulations, especially for the control of phytopathogenic fungi in plants, in the protection of materials and as plant growth regulators.

20 Claims, No Drawings

BINARY FUNGICIDAL COMPOSITION

CROSS REFERENCE TO RELATED APPLICATIONS

This application is a §371 National Stage Application of PCT/EP2014/065770, filed 23 Jul. 2014 which claims priority to EP 13177742.7, filed 24 Jul. 2013.

BACKGROUND

Field of Invention

The present invention relates to novel compositions and/or formulations, to a process for preparing these compositions and/or formulations and to the use thereof as biologically active compositions and biologically active formulations, especially for the control of phytopathogenic fungi in plants, in the protection of materials and as plant growth regulators.

Description of Related Art

Quinoline compounds are known as active compounds having controlling effects to rice blast (*Pyrcularia oryzae*) and gray mold (*Botrytis cinerea*) of tomato, cucumber and kidney bean etc. Control can be achieved by an application method such as seed disinfection, foliar spray treatment etc. (cf. WO 2005/070917 A1, JP 2007-1944 A, WO 2007/011022 A1, JP 2007-217353 A).

Moreover, it is known that these compounds can be mixed with different fungicidal compounds e.g. from the group consisting of a strobilurin series compound, a triazole series compound etc.; resulting compositions are for example known from EP 2517562 A1.

However the ecological and economic demands made on modern active ingredients, for example fungicides, are increasing constantly, for example with respect to activity spectrum, toxicity, selectivity, application rate, formation of residues and favourable manufacture. A further problem arising with the use of synthetic fungicides is that the repeated and exclusive application of a fungicide often leads to the selection of resistant microorganisms. Normally, such are also cross-resistant to other active ingredients having the same mode of action. An effective control of the pathogens with said active compounds is then no longer possible. However, active ingredients having new mechanisms of action are difficult to find and expensive to develop.

The risk of resistance development in pathogen populations as well as environmental and human health concerns have fostered interest in identifying alternatives to synthetic fungicides for managing plant diseases. The use of biological control agents (BCAs) is one alternative. However, the effectiveness of most BCAs is not at the same level as for conventional fungicides, especially in case of severe infection pressure. Consequently, known biological control agents, their mutants and metabolites produced by them are, in particular in low application rates, not entirely satisfactory.

Thus, there is a constant need for developing new, alternative plant protection products which in some areas at least help to fulfill the above-mentioned requirements. One way of fulfilling such need can be the development of novel compositions and/or formulations comprising of fungicides and biological control agents which have advantages over the known compositions and/or formulations at least in some areas.

In view of this, it was in particular an object of the present invention to provide compositions and/or formulations which exhibit activity against phytopathogenic fungi in plants, in the protection of materials and as plant growth regulators. Moreover, it was a further particular object of the present invention, to reduce the application rates and broaden the activity spectrum of the fungicides and the biological control agents, and thereby to provide a composition and/or formulation which, preferably at a reduced total amount of active compounds applied, has improved activity against phytopathogenic fungi. In particular, it was a further object of the present invention to provide a composition and/or formulation which, when applied to a crop, results in a decreased amount of residues in the crop, and nevertheless provides efficient disease control.

SUMMARY OF THE INVENTION

It has now surprisingly been found that compositions and/or formulations comprising (A) at least one compound of the general formula (I)

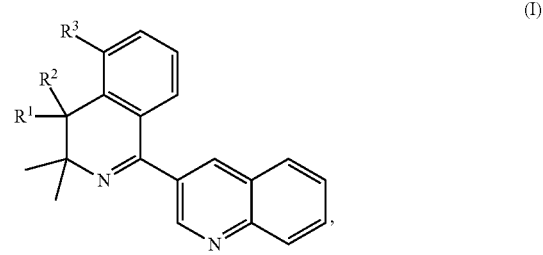

wherein
$R^1$ represents a methyl group or halogen and
$R^2$ represents a methyl group or halogen and
$R^3$ represents hydrogen or halogen and
(B) at least one biological control agent,
act in a fungicidal fashion. In some embodiments, such compositions and/or formulations act in a synergistic fashion.

The invention also comprises a method for preparing an agricultural composition comprising adding agriculturally suitable additives such as suitable extenders, solvents, spontaneity promoters, carriers, emulsifiers, dispersants, frost protectants, biocides, thickeners, adjuvants or the like to the composition according to the invention. Furthermore the invention comprises a method for reducing damage of plants and plant parts or losses in harvested fruits or vegetables caused by phytopathogenic fungi by controlling such phytopathogenic fungi, comprising applying the composition and/or formulation to the plant or the phytopathogenic fungi or the habitat of the plant or the habitat of the phytopathogenic fungi. In this connection the plants can be genetically modified or non-genetically modified.

In view of this, the problem underlying the present invention has been solved by providing novel compositions and/or formulations which exhibit fungicidal and/or synergistic activity against phytopathogenic fungi in plants, in the protection of materials and as plant growth regulators. Moreover, the novel compositions and/or formulations according to the invention enable reduced application rates and broaden the activity spectrum of the fungicides and the biological control agents Finally the novel compositions and/or formulations provide improved activity against phytopathogenic fungi and consequently provide efficient disease control for reducing damage of plants and plant parts or losses in harvested fruits or vegetables.

DETAILED DESCRIPTION OF A PREFERRED EMBODIMENT

The problem underlying the present invention has been solved by providing novel compositions and/or formulations comprising
(A) at least one compound of the general formula (I), whereby the compound of the general formula (I) is represented by one of the compounds (I-1) to (I-3):

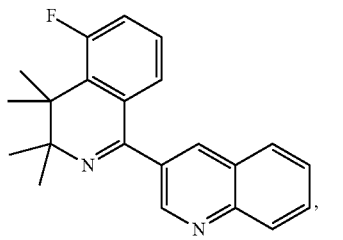

(I-1)

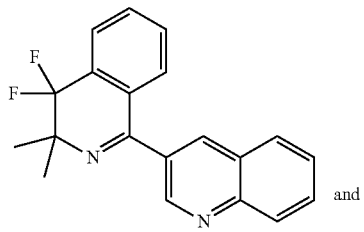

(I-2)

and

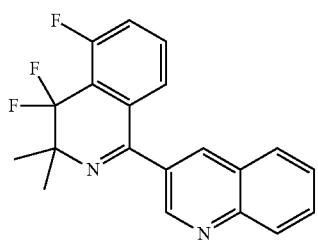

(I-3)

and
(B) at least one biological control agent,
which act in a fungicidal and/or synergistic fashion for efficient disease control comprising reducing damage of plants and plant parts or losses in harvested fruits or vegetables.

In general "pesticidal" means the ability of a substance to increase mortality or inhibit the growth rate of phytopathogenic fungi. The definition also comprises the ability of a substance to increase mortality or inhibit the growth rate of phytopathogenic fungi and/or plant pests. The term is used herein, to describe the property of a substance to exhibit activity against phytopathogenic fungi, insects, mites and/or nematodes.

"Fungicides" as well as the terms "fungicidal" and "acting in a fungicidal fashion" refer to the ability of a substance to increase mortality or inhibit growth rates of phytopathogenic fungi. Fungicides can be used in crop protection for control of phytopathogenic fungi. They are characterized by an outstanding efficacy against a broad spectrum of phytopathogenic fungi. As used herein, the term "phytopathogenic fungi" comprises all organisms of the kingdom of fungi including Oomycetes, which can cause damage of plants and/or damage of plant parts and/or losses in harvested fruits or vegetables. Specific phytopathogenic fungi are described later.

"Insecticides" as well as the term "insecticidal" refers to the ability of a substance to increase mortality or inhibit growth rate of insects. As used herein, the term "insects" comprises all organisms in the class "Insecta".

"Nematicide" and "nematicidal" refers to the ability of a substance to increase mortality or inhibit the growth rate of nematodes. In general, the term "nematode" comprises eggs, larvae, juvenile and mature forms of said organism.

"Acaricide" and "acaricidal" refers to the ability of a substance to increase mortality or inhibit growth rate of ectoparasites belonging to the class Arachnida, sub-class Acari.

Biological Control Agents

As used herein, the term "biological control" is defined as control of harmful organisms such as a phytopathogenic fungi and/or insects and/or acarids and/or nematodes by the use or employment of a biological control agent.

As used herein, the term "biological control agent" is defined as an organism other than the harmful organisms and/or proteins or secondary metabolites produced by such an organism for the purpose of biological control. Mutants of the second organism shall be included within the definition of the biological control agent. The term "mutant" refers to a variant of the parental strain as well as methods for obtaining a mutant or variant in which the pesticidal activity is greater than that expressed by the parental strain. The "parent strain" is defined herein as the original strain before mutagenesis. To obtain such mutants the parental strain may be treated with a chemical such as N-methyl-N'-nitro-N-nitrosoguanidine, ethylmethanesulfone, or by irradiation using gamma, x-ray, or UV-irradiation, or by other means well known to those skilled in the art. Known mechanisms of biological control agents comprise enteric bacteria that control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

A "variant" is a strain having all the identifying characteristics of the NRRL or ATCC Accession Numbers as indicated in this text and can be identified as having a genome that hybridizes under conditions of high stringency to the genome of the NRRL or ATCC Accession Numbers.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A variant of the indicated NRRL or ATCC Accession Number may also be defined as a strain having a genomic sequence that is greater than 85%, more preferably greater than 90% or more preferably greater than 95% sequence identity to the genome of the indicated NRRL or ATCC Accession Number. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example, those described in Current Protocols in Molecular Biology (F. M. Ausubel et al., eds., 1987).

NRRL is the abbreviation for the Agricultural Research Service Culture Collection, an international depositary authority for the purposes of depositing microorganism strains under the Budapest treaty on the international recognition of the deposit of microorganisms for the purposes of patent procedure, having the address National Center for Agricultural Utilization Research, Agricultural Research service, U.S. Department of Agriculture, 1815 North university Street, Peroira, Ill. 61604 USA.

ATCC is the abbreviation for the American Type Culture Collection, an international depositary authority for the purposes of depositing microorganism strains under the Budapest treaty on the international recognition of the deposit of microorganisms for the purposes of patent procedure, having the address ATCC Patent Depository, 10801 University Blvd., Manassas, Va. 10110 USA.

According to the present invention the biological control agents (B) are selected from the group consisting of:
B1. bacteria,
B2. fungi,
B3. protozoas,
B4. viruses,
B5. entomopathogenic nematode,
B6. proteins or secondary metabolites.

According to the invention the term "bacteria" include spore-forming, root-colonizing bacteria, or bacteria and their metabolites useful as biological fungicides, biological insecticdes, biological nematicdes or biological miticides, or soil amendments improving plant health and growth.

*Bacillus subtilis* AQ713 (Accession No. B-21661), also named *Bacillus subtilis* QST713, (in the following sometimes referred to as B1.1.1) exhibits a broad fungicidal and bactericidal activity and also exhibits corn rootworm activity (WO 98/50422 A1). Furthermore *Bacillus subtilis* AQ713 (Accession No. B-21661) contributes to an efficient crop productivity under unfavourable environmental conditions, e.g. by minimizing the influence of abiotic stress conditions. Commercially available formulations of this strain are available under the tradenames SERENADE® Max, SERENADE® Soil, SERENADE® Aso, SERENADE® CPB and RHAPSODY® from Bayer CropScience LP, US.

As described in WO 00/58442 A1 *Bacillus pumilus* QST2808 (NRRL Accession No. B-30087, in the following sometimes referred to as B1.1.6) is able to inhibit a broad range of fungal plant diseases in vivo. Moreover, the combination of this strain with *Bacillus thuringiensis* enhances the insecticidal activity of the latter. Commercially available formulations of this strain are sold under the tradenames SONATA® and BALLAD® Plus from Bayer CropScience LP, US.

*Bacillus subtilis* AQ30002, (Accession No. NRRL B-50421), also named *Bacillus subtilis* QST30002 (in the following sometimes referred to as B1.1.18) is described in U.S. patent application Ser. No. 13/330,576. It exhibits a broad fungicidal and bactericidal activity. Furthermore *Bacillus subtilis* AQ713 (Accession No. NRRL B-50421) contributes to an efficient crop productivity under unfavourable environmental conditions, e.g. by minimizing the influence of abiotic stress conditions. Commercially available formulation of this strain are available under the tradename Serenade-DPZ®.

Further examples of such bacteria to be used or employed according to the invention are (the numbering is used throughout the complete following description of the invention): B1.1 *Bacillus subtilis*, in particular strain QST713/AQ713 (e.g. SERENADE MAX from Bayer CropScience LP, US, having NRRL Accession No. B-21661 and described in U.S. Pat. No. 6,060,051); B1.2 *Bacillus subtilis* strain AQ153 (having NRRL Accession No. 55614 and described in U.S. Pat. No. 5,753,222); B1.3 *Bacillus* sp. strain AQ175 (having ATCC Accession No. 55608 and described in U.S. Pat. No. 5,869,042); B1.4 *Bacillus* sp. strain AQ177 (having ATCC Accession No. 55609 and described in U.S. Pat. No. 5,869,042); B1.5 *Bacillus* sp. strain AQ178 (having ATCC Accession No. 53522 and described in U.S. Pat. No. 5,869,042); B1.6 *Bacillus pumilus*, in particular strain QST2808 (e.g. Sonata® from Bayer CropScience LP, US, having Accession No. NRRL B-30087 and described in U.S. Pat. No. 6,245,551); B1.7 *Bacillus pumilus*, in particular strain GB34 (e.g. Yield Shield® from Bayer CropScience AG, DE); B1.8 *Bacillus thuringiensis* strain AQ52 (having Accession No. NRRL B-21619 and described in U.S. Pat. No. 5,919,447); B1.9 *Streptomyces* sp. strains, in particular the strain having Accession No. NRRL B-30145 and described in U.S. Pat. No. 6,524,577; B1.10 *Streptomyces galbus* (=*Streptomyces griseoviridis*), in particular *Streptomyces galbus* strain QST 6047 and mutants thereof (having Accession No. NRRL B-30232 and described in U.S. Pat. No. 6,682,925); B1.11 *Bacillus chitinosporus*, in particular strain AQ746 (having Accession No. NRRL B-21618 and described in U.S. Pat. No. 5,733,544); B1.12 *Bacillus mycoides*, strain AQ726 (having Accession No. NRRL B-21664 and described in U.S. Pat. Nos. 5,906,818 and 6,210,665); B1.13 *Bacillus pumilus*, in particular strain AQ717 (having Accession No. NRRL B21662 and described in U.S. Pat. No. 6,001,637); B1.14 *Bacillus subtilis*, in particular strain AQ743 (having Accession No. NRRL B-21665 and described in U.S. Pat. No. 6,015,553); B1.15 *Rhodococcus globerulus* strain AQ719 (having Accession No. NRRL B21663); B1.16 *Bacillus thuringiensis* subsp. *aizawai*, in particular strain ABTS-1857 (SD-1372; e.g. XenTarn® from Bayer Crop Science AG, DE); B1.17 *Bacillus firmus*, in particular, strain CNMC 1-1582 (e.g. VOTIVO from Bayer CropScience); B1.18 *Bacillus subtilis*, in particular strain AQ30002, (having Accession No. NRRL B-50421 and described in U.S. patent application Ser. No. 13/330,576); B1.19 *Bacillus subtilis*, in particular strain AQ30004 (having Accession No. NRRL B-50455 and described in U.S. patent application Ser. No. 13/330,576); B1.20 *Bacillus amyloliquefaciens*, strain D747 (e.g. Bacstar® from Etec Crop Solutions, NZ and also e.g. Double Nickel™ from Certis, US); B1.21 *Bacillus pumilus*, in particular strain BU F-33 (e.g. Integral F-33 from Becker Underwood, US); B1.22 *B. subtilis* var. *amyloliquefaciens* strain FZB24 (e.g. Taegro® from Novozymes, US); B1.23 *Paenibacillus polymyxa*, in particular strain AC-1 (e.g. Topseed from Green Biotech Company Ltd.); B1.24 *Pseudomonas proradix* (e.g. Proradix® from Sourcon Padena); B1.25 *Bacillus amyloliquefaciens* strain MBI 600 (e.g. Subtilex from Becker Underwood, US); B1.26 *Bacillus amyloliquefaciens* strain GB03 (e.g. Kodiak® from Bayer Crop Science AG, DE); B1.27 *Bacillus amyloliquefaciens* strain DB 101 (e.g. Shelter from Dagutat Bio lab, ZA); B1.28 *Bacillus amyloliquefaciens* strain DB 102 (e.g. Artemis from Dagutat Bio lab, ZA); B1.29 *Bacillus amyloliq-* uefaciens isolate B246 (e.g. Avogreen from University of Pretoria); B1.30 *Bacillus licheniformis*, in particular strain SB3086 (e.g. EcoGuard™ Biofungicide and Green Releaf from Novozymes); B1.31 *Pseudomonas syringae*, in particular strain MA-4 (e.g. Biosave from EcoScience, US); B1.32 *Pseudomonas syringae* strain 742RS (e.g. Frostban C from Frost Technology Corp); B1.33 *Pseudomonas fluorescens*, in particular strain 1629RS (e.g. Frostban D from Frost Technology Corp); B1.34 *Streptomyces galbus* (*Streptomyces griseoviridis*), in particular strain K61 (Accession No. DSM 7206; e.g. Mycostop® from Verdera, cf. Crop Protection 2006, 25, 468-475); B1.35 *Streptomyces lydicus*, in particular strain WYEC108 (e.g. Actinovate from Natural Industries, US); B1.36 *Agrobacterium radiobacter*, in particular strain K84 (e.g. Galltrol-A from AgBioChem, CA); B1.37 *Agrobacterium radiobacter* strain K1026 (e.g. Nogall from Becker Underwood, US); B1.38 *Bacillus lentimorbus;* B1.39 *Bacillus mycoides*, isolate J. (e.g. BmJ from Certis USA); B1.40 *Bacillus sphaericus*, in particular Serotype H5a5b strain 2362 (e.g. VectoLex® from Valent BioSciences, US); B1.41 *Bacillus thuringiensis* subsp. *kurstaki* strain BMP 123 from Becker Microbial Products, IL; B1.42 *Bacillus thuringiensis* subsp. *aizawai*, in particular serotype H-7 (e.g. Florbac WG from Valent BioSciences, US); B1.43 *Bacillus thuringiensis* subsp. *kurstaki* strain HD-1 (e.g. Dipel® ES from Valent BioSciences, US); B1.44 *Bacillus thuringiensis* subsp. *tenebrionis* strain NB 176 (SD-5428; e.g. Novodor® FC from BioFa DE); B1.45 *Bacillus thuringiensis* var. *japonensis* strain Buibui; B1.46 *Burkholderia* spp., in particular strain A396 (Accession No. NRRL B-50319; e.g. MBI-206 TGAI from Marrone Bio Innovations); B1.47 *Chromobacterium subtsugae*, in particular strain PRAA4-1T (MBI-203; e.g. Grandevo from Marrone Bio Innovations); B1.48 *Paenibacillus popilliae* (formerly *Bacillus popilliae*; e.g. Milky spore disease from St. Gabriel Laboratories); B1.49 *Xenorhabdus luminescens*; B1.50 *Xenorhabdus nematophila*; B1.51 *Bacillus thuringiensis*, in particular *Bacillus thuringiensis* subspecies *israelensis* (serotype H-14); B1.52 *Bacillus amyloliquefaciens*, in particular strain FZB42 (e.g. RhizoVital® from ABiTEP, DE); B1.53 *Bacillus cereus*; B1.54 spores of *Bacillus cereus* strain CNCM 1-1562 (cf. U.S. Pat. No. 6,406,690); B1.55 *Bacillus laterosporus* (also known as *Brevibacillus laterosporus;* e.g. Bio-Tode from Agro-Organics, SA); B1.56 *Bacillus megaterium*, strain YFM3.25 (e.g. Bioarc from BioArc); B1.57 *Bacillus mojavensis*, strain SR11 (CECT-7666) by Probelte, Sa; B1.58 *Bacillus nematocida;* B1.59 *Pasteuria nishizawae* (e.g. oyacyst LF/ST from *Pasteuria* Bioscience); B1.60 *Pasteuria penetrans* (formerly *Bacillus penetrans*, e.g. *Pasteuria* wettable powder from *Pasteuria* Bioscience); B1.61 *Pasteuria usgae* (e.g. Econem™ from *Pasteuria* Bioscience); B1.62 compositions comprising nematicidal *Streptomycete* sp., such as *Streptomyces lydicus* (commercially e.g. ACTINOVATE®); B1.63 compositions comprising nematicidal *Streptomycete* sp., such as *Streptomyces saraceticus* (e.g. Clanda from A & A Group (Agro Chemical Corp.); B1.64 *Bacillus amyloliquefaciens*, in particular strain IN937a; B1.65 *Bacillus cereus*, in particular strain BP01 (ATCC 55675, e.g. Mepichlor from Arysta, US and also e.g. Mepplus from Micro-Flo Company LLC, US); B1.66 *Bradyrhizobium japonicum* (e.g. Optimize from Novozymes); B1.67 *Delftia acidovorans*, in particular strain RAY209 (e.g. BioBoost® from Brett Young Seeds); B1.68 *Lactobacillus* sp. (e.g. Lactoplant from LactoPAFI); B1.69 *Pseudomonas aeruginosa*, in particular strain PN1; B1.70 *Rhizobium leguminosarum*, in particular bv. *viceae* strain Z25 (Accession No. CECT 4585); B1.71 *Streptomyces acidiscabies*, in particular strain RL-110T (e.g. MBI-005EP from Marrone Bioinnovations, CA); B1.72 *Bacillus azotoformans*; B1.73 *Bacillus smithii*; B1.74 *Bacillus subtilis*, in particular strain DB 101; B1.75 *Lysobacter antibioticus*, in particular strain 13-1 (cf. Biological Control 2008, 45, 288-296); B1.76 *Pantoea agglomerans*, in particular strain E325 (Accession No. NRRL B-21856); B1.77 *Bacillus coagulans*, in particular strain TQ33; B1.78 *Bacillus popilliae* (e.g. Cronox by Bio-Crop, CO); B1.79 *Bacillus cepacia* (e.g. Deny Stine by Microbial Products); B1.80 *Lactobacillus acidophilus* (e.g. Fruitsan by Inagrosa-Industrias Agrobiologicas, S.A); B1.81 *Lysobacter enzymogenes*, in particular strain C3 (cf. J Nematol. 2006 June; 38(2): 233-239); B1.82 *Pseudomonas aeruginosa*, in particular strain WS-1; B1.83 *Pseudomonas aureofaciens*, in particular strain TX-1 (e.g. Spot-Less Biofungicide by Eco Soils Systems, CA); B1.84 *Pseudomonas cepacia* (formerly known as *Burkholderia cepacia*), in particular type Wisconsin, strain M54; B1.85 *Pseudomonas cepacia* (formerly known as *Burkholderia cepacia*), in particular type Wisconsin, strain J82; B1.86 *Pseudomonas chlororaphis*, in particular strain 63-28 (e.g. ATEze by EcoSoil Systems); B1.87 *Pseudomonas fluoresces*, in particular strain A506 (e.g. Blightban by NuFarm and also e.g. Frostban B by Frost Technology Corp); B1.88 *Pseudomonas resinovorans* (e.g. Solanacure by Agricultural Research Council, SA); B1.89 *Streptomyces* sp., in particular strain WYE 324 (KCTCO342BP); B1.90 *Streptomyces candidus*, in particular strain Y21007-2 (e.g. BioBac by Biontech, TW); B1.91 *Brevibacillus brevis* (formerly *Bacillus brevis;* e.g. Brevisin); B1.92 *Pectobacterium carotovorum* (formerly *Erwinia carotovora;* e.g. BioKeeper by Nissan, JP); B1.93 *Pseudomonas chlororaphis*, in particular strain MA 342 (e.g. Cedomon by Bioagri, S); B1.94 *Bacillus thuringiensis* subsp. *kurstaki* strain ABTS 351; B1.95 *Bacillus thuringiensis* subsp. *kurstaki* strain PB 54; B1.96 *Bacillus thuringiensis* subsp. *kurstaki* strain SA 11; B1.97 *Bacillus thuringiensis* subsp. *kurstaki* strain SA 12; B1.98 *Bacillus thuringiensis* subsp. *kurstaki* strain EG 2348; B1.99 *Bacillus thuringiensis* var. *Colmeri* (e.g. TianBaoBTc by Changzhou Jianghai Chemical Factory); B1.100 *Bacillus thuringiensis* subsp. *aizawai* strain GC-91; B1.101 *Rhizobium meliloti*; B1.102 *Serratia entomophila* (e.g. Invade® by Wrightson Seeds); B1.103 *Serratia marcescens*, in particular strain SRM (Accession No. MTCC 8708); B1.104 *Streptomyces prasinus* (cf. "Prasinons A and B: potent insecticides from *Streptomyces prasinus*" Applied microbiology 1973 November); B1.105 *Bacillus kurstaki*; B1.106 *Bacillus aizawai*; B1.107 *Bacillus albolactis*; B1.108 *Bacillus thuringiensis* strain CR-371 (Accession No. ATCC 55273); B1.109 *Pasteuria thornei*; B1.110 *Azo-rhizobium caulinodans*, preferably strain ZB-SK-5; B1.111 *Azospirillum amazonense*; B1.112 *Azospirillum brasilense*; B1.113 *Azospirillum halopraeference*; B1.114 *Azospirillum irakense*; B1.115 *Azospirillum lipoferum*; B1.116 *Azotobacter chroococcum*, preferably strain H 23; B1.117 *Azotobacter vinelandii*, preferably strain ATCC 12837; B1.118 *Bacillus lacticola* by Micro-Flo Company; B1.119 *Bacillus lactimorbus* by Micro-Ho Company; B1.120 *Bacillus lactis* from Micro-Ho Company; B1.121 *Bacillus maroccanus* from Micro Flo Company; B1.122 *Bacillus metiens* from Micro Flo Company; B1.123 *Bacillus nigrificans* from Micro Flo Company; B1.124 *Bacillus siamensis*, in particular strain KCTC 13613T; B1.125 *Bacillus tequilensis*, in particular strain MI-0943; B1.126 *Gluconacetobacter diazotrophicus*; B1.127 *Rhizobium fredii*; B1.128 *Thiobacillus* sp. (e.g. Cropaid from Cropaid Ltd UK); B1.129 *Xanthomonas campestris* (herbicidal activity), in particular pv *poae* (e.g.

Camperico); B1.130 *Agrobacterium vitis*, in particular the non-pathogenic strain VAR03-1; B1.131 *Bacillus acidocaldarius*; B1.132 *Bacillus acidoterrestris*; B1.133 *Bacillus alcalophilus*; B1.134 *Bacillus alvei*; B1.135 *Bacillus aminoglucosidicus*; B1.136 *Bacillus aminovorans*; B1.137 *Bacillus amylolyticus*; B1.138 *Bacillus amyloliquefaciens*, strain B3; B1.139 *Bacillus aneurinolyticus*; B1.140 *Bacillus atrophaeus*; B1.141 *Bacillus badius*; B1.142 *Bacillus circulans*; B1.143 *Bacillus fastidiosus*; B1.144 *Bacillus lautus*; B1.145 *Bacillus lentus*; B1.146 *Bacillus medusa*; B1.147 *Bacillus psychrosaccharolyticus*; B1.148 *Bacillus subtilis* subspecies natto (formerly *Bacillus* natto); B1.149 *Bacillus thuringiensis*, in particular strain AM65-52 (e.g. VectoBac® by Valent BioSciences, US); B1.150 *Bacillus thuringiensis israelensis* strain BMP 144 (e.g. Aquabac by Becker Microbial Products IL); B1.151 *Bacillus thuringiensis* subspecies. *Aegypti* (e.g. Agerin); B1.152 *Bacillus thuringiensis* var. *darmstadiensis* strain 24-91 (e.g. Baciturin); B1.153 *Bacillus thuringiensis* var. *dendrolimus* (e.g. Dendrobacillin); B1.154 *Bacillus thuringiensis* var. galleriae; B1.155 *Bacillus thuringiensis* subsp. *Morrisoni*; B1.156 *Bacillus thuringiensis* var. san diego (e.g. M-One® by Mycogen Corporation, US); B1.157 *Bacillus thuringiensis* subsp. *thuringiensis* serotype 1, strain MPPL002; B1.158 *Bacillus thuringiensis* var. *thuringiensis*; B1.159 *Bacillus thuringiensis* var. 7216 (e.g. Amactic and Pethian); B1.160 *Bacillus thuringiensis* var. T36 (e.g. Cahat); B1.161 *Bacillus uniflagellatus*; B1.162 *Brevibacillus brevis* (formerly *Bacillus brevis*), in particular strain SS86-3; B1.163 *Brevibacillus brevis* (formerly *Bacillus brevis*), in particular strain SS86-4; B1.164 *Brevibacillus brevis* (formerly *Bacillus brevis*), in particular strain SS86-5; B1.165 *Brevibacillus brevis* (formerly *Bacillus brevis*), in particular strain 2904; B1.166 *Brevibacillus laterosporus* (formerly *Bacillus laterosporus*); B1.167 *Brevibacillus laterosporus* (formerly *Bacillus laterosporus*), in particular strain ATCC 64; B1.168 *Brevibacillus laterosporus* (formerly *Bacillus laterosporus*), in particular strain NRS 1111; B1.169 *Brevibacillus laterosporus* (formerly *Bacillus laterosporus*), in particular strain NRS 1645; B1.170 *Brevibacillus laterosporus* (formerly *Bacillus laterosporus*), in particular strain NRS 1647; B1.171 *Brevibacillus laterosporus* (formerly *Bacillus laterosporus*), in particular strain BPM3; B1.172 *Brevibacillus laterosporus* (formerly *Bacillus laterosporus*), in particular strain G4; B1.173 *Brevibacillus laterosporus* (formerly *Bacillus laterosporus*), in particular strain NCIMB; B1.174 *Brevibacillus laterosporus* (formerly *Bacillus laterosporus*), in particular strain 41419; B1.175 *Corynebacterium paurometabolum*; B1.176 Herbaspirilum *rubrisubalbicans*; B1.177 *Herbaspirilum seropedicae*; B1.178 *Paenibacillus alvei*, in particular strain 1113DT-1A; B1.179 *Paenibacillus alvei*, in particular strain D12E; B1.180 *Paenibacillus alvei*, in particular strain 46C3; B1.181 *Paenibacillus alvei*, in particular strain 2771; B1.182 *Paenibacillus macerans*; B1.183 *Pasteuria ramose*; B1.184 *Pasteuria renifomis*; B1.185 *Pseudomonas putida*; B1.186 *Rhizobium loti*; B1.187 *Rhizobium trifolii*; B1.188 *Rhizobium tropici*; B1.189 *Serratia marcescens*, in particular strain R35; B1.190 *Streptomyces colombiensis*; B1.191 *Streptomyces goshikiensis*; B1.192 *Streptomyces lavendulae*; B1.193 *Streptomyces lydicus*, in particular strain WYCD108US; B1.194 *Streptomyces rimosus*; B1.195 *Streptomyces venezuelae*; B1.196 *Virgibacillus pantothenticus* (formerly *Bacillus pantothenticus*), in particular strain ATCC 14576/DSM 491; B1.197 *Bacillus thuringiensis* strain BD#32 (Accession No. NRRL B-21530 and described in U.S. Pat. No. 5,645,831); B1.198 *Streptomyces* sp. strain WYE 20 (KCTC 0341BP) and B1.199 *Bacillus agri*.

In some embodiments of the invention such biological control agents which are summarized under the term bacteria according to the invention include: B1.1.1 *Bacillus subtilis*, strain QST713/AQ713 (Accession No. NRRL B-21661); B1.1.6 *Bacillus pumilus*, strain QST2808 (Accession No. NRRL B-30087); B1.1.7 *Bacillus pumilus*, strain GB34; B1.1.9 *Streptomyces* sp., strain having Accession No. NRRL B-30145; B1.1.10 *Streptomyces galbus* (=*Streptomyces griseoviridis*), strain QST 6047 (Accession No. NRRL B-30232); B1.1.11 *Bacillus chitinosporus*, strain AQ746 (Accession No. NRRL B-21618); B1.1.13 *Bacillus pumilus*, strain AQ717 (having Accession No. NRRL B21662); B1.1.14 *Bacillus subtilis*, strain AQ743 (having Accession No. NRRL B-21665); 1.1.16 *Bacillus thuringiensis* subsp. *aizawai*, strain ABTS-1857 (SD-1372); B1.1.17 *Bacillus firmus*, strain CNMC 1-1582; B1.1.18 *Bacillus subtilis*, strain AQ30002, (Accession No. NRRL B-50421); B1.1.19 *Bacillus subtilis*, strain AQ30004 (Accession No. NRRL B-50455); B1.1.21 *Bacillus pumilus*, strain BU F-33; B1.1.23 *Paenibacillus polymyxa*, strain AC-1; B1.1.30 *Bacillus licheniformis*, strain SB3086; B1.1.31 *Pseudomonas syringae*, strain MA-4; B1.1.33 *Pseudomonas fluorescens*, strain 1629RS; B1.1.34 *Streptomyces galbus* (*Streptomyces griseoviridis*), strain K61 (Accession No. DSM 7206); B1.1.35 *Streptomyces lydicus*, strain WYEC108; B1.1.36 *Agrobacterium radiobacter*, strain K84; B1.1.40 *Bacillus sphaericus*, Serotype H5a5b strain 2362; B1.1.42 *Bacillus thuringiensis* subsp. *aizawai*, serotype H-7; B1.1.46 *Burkholderia* spp., strain A396 (Accession No. NRRL B-50319); B1.1.47 *Chromobacterium subtsugae*, strain PRAA4-1T (MBI-203); B1.1.51 *Bacillus thuringiensis* subspecies *israelensis* (serotype H-14); B1.1.52 *Bacillus amyloliquefaciens*, strain FZB42; B1.1.64 *Bacillus amyloliquefaciens*, strain IN937a; B1.1.65 *Bacillus cereus*, strain BP01 (ATCC Accession No. 55675); B1.1.67 Delftia *acidovorans*, strain RAY209; B1.1.69 *Pseudomonas aeruginosa*, strain PN1; B1.1.70 Rhizobium *leguminosarum*; Bv. *viceae* strain Z25 (Accession No. CECT 4585); B1.1.71 *Streptomyces acidiscabies*, strain RL-110T; B1.1.74 *Bacillus subtilis*, strain DB 101; B1.1.75 *Lysobacter antibioticus*, strain 13-1; B1.1.76 *Pantoea agglomerans*, strain E325 (Accession No. NRRL B-21856); B1.1.77 *Bacillus coagulans*, strain TQ33; B1.1.81 *Lysobacter enzymogenes*, strain C3; B1.1.82 *Pseudomonas aeruginosa*, strain WS-1; B1.1.83 *Pseudomonas aureofaciens*, strain TX-1; B1.1.84 *Pseudomonas cepacia* (formerly known as *Burkholderia cepacia*); type Wisconsin, strain M54; B1.1.85 *Pseudomonas cepacia* (formerly known as *Burkholderia cepacia*); type Wisconsin, strain J82; B1.1.86 *Pseudomonas chlororaphis*, strain 63-28; B1.1.87 *Pseudomonas fluorescens*, strain A506; B1.1.89 *Streptomyces* sp., strain WYE 324 (KCTCO342BP); B1.1.90 *Streptomyces candidus*, strain Y21007-2; B1.1.93 *Pseudomonas chlororaphis*, strain MA 342; B1.1.103 *Serratia marcescens*, strain SRM; B1.1.124 *Bacillus siamensis*, strain KCTC 13613T; B1.1.125 *Bacillus tequilensis*, strain NII-0943; B1.1.129 *Xanthomonas campestris* (herbicidal activity); pv poae; B1.1.130 *Agrobacterium vitis*, the non-pathogenic strain VAR03-1; B1.1.149 *Bacillus thuringiensis*, strain AM65-52; B1.1.162 *Brevibacillus brevis* (formerly *Bacillus brevis*), strain SS86-3; B1.1.163 *Brevibacillus brevis* (formerly *Bacillus brevis*), strain SS86-4; B1.1.164 *Brevibacillus brevis* (formerly *Bacillus brevis*), strain SS86-5; B1.1.165 *Brevibacillus brevis* (formerly *Bacillus brevis*), strain 2904; B1.1.167 *Brevibacillus laterosporus* (formerly *Bacillus laterosporus*), strain ATCC 64; B1.1.168 *Brevibacillus laterosporus* (formerly *Bacillus laterosporus*), strain NRS 1111; B1.1.169

*Brevibacillus laterosporus* (formerly *Bacillus laterosporus*), strain NRS 1645; B1.1.170 *Brevibacillus laterosporus* (formerly *Bacillus laterosporus*), strain NRS 1647; B1.1.171 *Brevibacillus laterosporus* (formerly *Bacillus laterosporus*), strain BPM3; B1.1.172 *Brevibacillus laterosporus* (formerly *Bacillus laterosporus*), strain G4; B1.1.173 *Brevibacillus laterosporus* (formerly *Bacillus laterosporus*), strain NCIMB; B1.1.174 *Brevibacillus laterosporus* (formerly *Bacillus laterosporus*), strain 41419; B1.1.178 *Paenibacillus alvei*, strain III3DT-1A; B1.1.179 *Paenibacillus alvei*, strain 1112E; B1.1.180 *Paenibacillus alvei*, strain 46C3; B1.1.181 *Paenibacillus alvei*, strain 2771; B1.1.188 *Rhizobium tropici*; B1.1.189 *Serratia marcescens*, strain R35; B1.1.193 *Streptomyces lydicus*, strain WYCD108US and B1.1.196 *Virgibacillus pantothenticus* (formerly *Bacillus pantothenticus*), strain ATCC 14576/DSM 491.

According to the invention the term "fungi" comprises all organisms belonging to the kingdom of fungi, including yeast, useful as biological fungicides, biological insecticdes, biological nematicdes or biological miticides, or soil amendments improving plant health and growth. Examples of such fungi to be used or employed according to the invention are (the numbering is used throughout the complete following description of the invention): B2.1 *Coniothyrium minitans*, in particular strain CON/M/91-8 (Accession No. DSM-9660; e.g. Contans® from Encore Technologies, LLC); B2.2 *Metschnikowia fructicola*, in particular strain NRRL Y-30752 (e.g. Shemer® from Bayer CropScience); B2.3 *Microsphaeropsis ochracea* (e.g. Microx® from Prophyta); B2.4 *Muscodor albus*, in particular strain QST 20799 (Accession No. NRRL 30547); B2.5 *Trichoderma* spp., including *Trichoderma atroviride*, strain SC1 (described in International Application No. PCT/IT2008/000196); B2.6 *Trichoderma harzianum rifai* strain KRL-AG2 (also known as strain T-22, /ATCC 208479, e.g. PLANTSHIELD T-22G, Rootshield®, and TurfShield from BioWorks, US); B2.7 *Muscodor roseus* strain A3-5 (Accession No. NRRL 30548); B2.8 *Paecilomyces lilacinus*, in particular spores of *P. lilacinus* strain 251 (AGAL 89/030550; e.g. BioAct from Prophyta); B2.9 *Trichoderma koningii*; B2.10 *Talaromyces flavus*, strain V117b (e.g. PROTUS® WG by Prophyta, DE); B2.11 *Trichoderma atroviride*, strain no. V08/002387; B2.12 *Trichoderma atroviride*, strain no. NMI No. V08/002388; B2.13 *Trichoderma atroviride*, strain no. NMI No. V08/002389; B2.14 *Trichoderma atroviride*, strain no. NMI No. V08/002390; B2.15 *Trichoderma harzianum*, strain ITEM 908 (e.g. Trianum-P from Koppert); B2.16 *Pseudozyma aphidis*; B2.17 *Pseudozyma aphidis* (from Yissum Research Development Company of the Hebrew University of Jerusalem); B2.18 *Arthrobotrys dactyloides*; B2.19 *Arthrobotrys oligospora;* B2.20 *Arthrobotrys superba;* B2.21 *Aspergillus flavus*, strain NRRL 21882 (e.g. Afla-Guard® from Syngenta); B2.22 *Aspergillus flavus*, strain AF36 (e.g. AF36 from Arizona Cotton Research and Protection Council, US); B2.23 *Cryptococcus albidus* (e.g. YieldPlus® from Anchor Bio-Technologies, ZA); B2.24 *Cryptococcus flavescens*, strain 4C (NRRL Y-50379); B2.25 *Gliocladium roseum*, strain 321U from W.F. Stoneman Company LLC; B2.26 *Phlebiopsis* (or *Phlebia* or *Peniophora*) *gigantea*, in particular strain VRA 1835 (ATCC 90304); B2.27 *Phlebiopsis* (or *Phlebia* or *Peniophora*) *gigantea*, in particular strain VRA 1984 (DSM16201); B2.28 *Phlebiopsis* (or *Phlebia* or *Peniophora*) *gigantea*, in particular strain VRA 1985 (DSM16202); B2.29 *Phlebiopsis* (or *Phlebia* or *Peniophora*) *gigantea*, in particular strain VRA 1986 (DSM16203); B2.30 *Phlebiopsis* (or *Phlebia* or *Peniophora*) *gigantea*, in particular strain FOC PG B20/5 (IMI390096); B2.31 *Phlebiopsis* (or *Phlebia* or *Peniophora*) *gigantea*, in particular strain FOC PG SP log 6 (IMI390097); B2.32 *Phlebiopsis* (or *Phlebia* or *Peniophora*) *gigantea*, in particular strain FOC PG SP log 5 (IMI390098); B2.33 *Phlebiopsis* (or *Phlebia* or *Peniophora*) *gigantea*, in particular strain FOC PG BU3 (IMI390099); B2.34 *Phlebiopsis* (or *Phlebia* or *Peniophora*) *gigantea*, in particular strain FOC PG BU4 (IMI390100); B2.35 *Phlebiopsis* (or *Phlebia* or *Peniophora*) *gigantea*, in particular strain FOC PG 410.3 (IMI390101); B2.36 *Phlebiopsis* (or *Phlebia* or *Peniophora*) *gigantea*, in particular strain FOC PG 97/1062/116/1.1 (IMI390102); B2.37 *Phlebiopsis* (or *Phlebia* or *Peniophora*) *gigantea*, in particular strain FOC PG B22/SP1287/3.1 (IMI390103); B2.38 *Phlebiopsis* (or *Phlebia* or *Peniophora*) *gigantea*, in particular strain FOC PG SH1 (IMI390104); B2.39 *Phlebiopsis* (or *Phlebia* or *Peniophora*) *gigantea*, in particular strain FOC PG B22/SP1190/3.2 (IMI390105; e.g. Rotstop® from Verdera and FIN, PG-Agromaster®, PG-Fungler®, PG-IBL®, PG-Poszwald®, and Rotex® from e-nema, DE); B2.40 *Pythium oligandrum*, strain DV74 or M1 (ATCC 38472; e.g. Polyversum from Biopreparaty, CZ); B2.41 *Saccharomyces cerevisae*, strain CNCM No. 1-3936 (from Lesaffre et Compagnie, FR); B2.42 *Saccharomyces cerevisae*, strain CNCM No. 1-3937 (from Lesaffre et Compagnie, FR); B2.43 *Saccharomyces cerevisae*, strain CNCM No. 1-3938 (from Lesaffre et Compagnie, FR); B2.44 *Saccharomyces cerevisae*, strain CNCM No. 1-3939 (from Lesaffre et Compagnie, FR); B2.45 *Scleroderma citrinum;* B2.46 *Trichoderma asperellum*, strain ICC 012 from Isagro; B2.47 *Trichoderma asperellum*, strain SKT-1 (e.g. ECO-HOPE® from Kumiai Chemical Industry); B2.48 *Trichoderma atroviride*, strain CNCM 1-1237 (e.g. Esquive® WP from Agrauxine, FR); B2.49 *Trichoderma atroviride*, strain LC52 (e.g. Tenet by Agrimm Technologies Limited); B2.50 *Trichoderma atroviride*, strain ATCC 20476 (IMI 206040); B2.51 *Trichoderma atroviride*, strain T11 (IMI352941/CECT20498); B2.52 *Trichoderma hatmatum;* B2.53 *Trichoderma harzianum;* B2.54 *Trichoderma harzianum rifai* T39 (e.g. Trichodex® from Makhteshim, US); B2.55 *Trichoderma harzianum*, in particular, strain KD (e.g. Trichoplus from Biological Control Products, SA (acquired by Becker Underwood)); B2.56 *Trichoderma harzianum*, strain KD (e.g. Eco-T from Plant Health Products, SZ); B2.57 *Trichoderma harzianum*, strain TH35 (e.g. Root-Pro by Mycontrol); B2.58 *Trichoderma virens* (also known as *Gliocladium virens*), in particular strain GL-21 (e.g. SoilGard 12G by Certis, US); B2.59 *Trichoderma viride*, strain TV1 (e.g. Trianum-P by Koppert); B2.60 *Beauveria bassiana*, strain ATCC 74040 (e.g. Naturalis® from Intrachem Bio Italia); B2.61 *Beauveria bassiana* strain GHA (Accession No. ATCC 74250; e.g. BotaniGuard Es and Mycontrol-0 from Laverlam International Corporation); B2.62 *Beauveria bassiana* strain ATP02 (Accession No. DSM 24665); B2.63 *Beauveria bassiana* strain CG 716 (e.g. BoveMax® from Novozymes); B2.64 *Hirsutella citriformis;* B2.65 *Hirsutella thompsonii* (with some strains e.g. Mycohit and ABTEC from Agro Bio-tech Research Centre, IN); B2.66 *Lecanicillium lecanii* (formerly known as *Verticillium lecanii*) conidia of strain KV01 (e.g. Mycotal® and Vertalec® from Koppert/Arysta); B2.67 *Lecanicillium lecanii* (formerly known as *Verticillium lecanii*) conidia of strain DAOM198499; B2.68 *Lecanicillium lecanii* (formerly known as *Verticillium lecanii*) conidia of strain DAOM216596; B2.69 *Lecanicillium muscarium* (formerly *Verticillium lecanii*), strain VE 6/CABI(=IMI) 268317/CBS102071/2.70 ARSEF5128; B2.71 *Metarhizium anisopliae*, strain F52 (DSM3884/ATCC 90448; e.g. BIO 1020 by Bayer CropScience and also e.g. Met52 by Novozymes); B2.72 *Metarhizium anisopliae* var. *acridum* (e.g. GreenGuard by Becker Underwood, US); B2.73 *Metarhizium anisopliae* var. *acridum* isolate IMI 330189 (AR-SEF7486; e.g. Green Muscle by Biological Control Products); B2.74 *Nomuraea rileyi*; B2.75 *Paecilomyces fumosoroseus* (new: *Isaria fumosorosea*), strain apopka 97 (e.g. PreFeRal® WG from Biobest); B2.76 *Paecilomyces fumosoroseus* (new: *Isaria fumosorosea*) strain FE 9901 (e.g. NoFly® from Natural Industries Inc., a Novozymes company); B2.77 *Harposporium anguillullae*; B2.78 *Hirsutella minnesotensis*; B2.79 *Monacrosporium cionopagum*; B2.80 *Monacrosporium psychrophilum*; B2.81 *Myrothecium verrucaria*, strain AARC-0255 (e.g. DiTera™ by Valent Biosciences); B2.82 compositions comprising the fungus *Paecilomyces lilacinus* (commercially available as e.g. MELOCON® or BIOACT); B2.83 *Paecilomyces variotii*, strain Q-09 (e.g. Nemaquim® from Quimia, MX); B2.84 compositions comprising the bacterium *Pasteuria* including *Pasteuria usgae* (commercially available as e.g.) ECONEM®; B2.85 *Stagonospora phaseoli* (commercially available e.g. from Syngenta); B2.86 *Trichoderma lignorum*, in particular strain TL-0601 (e.g. Mycotric from Futureco Bioscience, ES); B2.87 *Penicillium bilaii*, strain ATCC 22348 (e.g. JumpStart® from Novozymes); B2.88 *Penicillium bilaii*, in particular strain ATCC 22348 (e.g. PB-50 PROVIDE from Philom Bios Inc., Saskatoon, Saskatchewan); B2.89 *Rhizopogon amylopogon* (e.g. Myco-Sol from Helena Chemical Company); B2.90 *Rhizopogon fulvigleba* (e.g. Myco-Sol from Helena Chemical Company); B2.91 *Trichoderma harzianum*, strain TSTh20; B2.92 *Phoma macrostroma*, strain 94-44B (e.g. Phoma H and Phoma P by Scotts, US); B2.93 *Sclerotinia minor*, strain IMI 344141 (e.g. Sarritor by Agrium Advanced Technologies); B2.94 *Ampelomyces quisqualis*, in particular strain AQ 10 (e.g. AQ 10® by IntrachemBio Italia); B2.95 Arkansas fungus 18, ARF; B2.96 *Aureobasidium pullulans*, in particular blastospores of strain DSM14940; B2.97 *Aureobasidium pullulans*, in particular blastospores of strain DSM14941; B2.98 *Aureobasidium pullulans*, in particular mixtures of blastospores of strains DSM14940 and DSM14941 (e.g. Botector® by bio-ferm, CH); B2.99 *Candida oleophila*, strain 0 (e.g. Nexy® by BioNext); B2.100 *Candida oleophila*, isolate 1-182 (e.g. Aspire® by Ecogen, US); B2.101 *Candida saitoana*, strain NRRL Y-21022 (by Biotechnology Research And Development Corporation); B2.102 *Chaetomium cupreum* (e.g. BIOKUPRUM™ by AgriLife); B2.103 *Chaetomium globosum* (e.g. Rivadiom by Rivale); B2.104 *Cladosporium cladosporioides*, strain H39 (by Stichting Dienst Landbouwkundig Onderzoek); B2.105 *Cryptococcus flavescens*, strain 3C (NRRL Y-50378); B2.106 Dactylaria *candida*; B2.107 *Dilophosphora alopecuri* (e.g. Twist Fungus); B2.108 *Fusarium oxysporum*, strain Fo47 (e.g. Fusaclean by Natural Plant Protection); B2.109 *Gliocladium catenulatum* (Synonym: *Clonostachys rosea* f. *catenulate*) strain J1446 (e.g. Prestop® by AgBio Inc. and also e.g. Primastop® by Kemira Agro Oy); B2.110 *Penicillium vemiculatum*; B2.111 *Pichia anomala*, strain WRL-076 (NRRL Y-30842); B2.112 *Pseudozyma flocculosa*, strain PF-A22 UL (e.g. Sporodex® L by Plant Products Co., CA); B2.113 *Trichoderma atroviride*, strain SKT-1 (FERM P-16510); B2.114 *Trichoderma atroviride*, strain SKT-2 (FERM P-16511); B2.115 *Trichoderma atroviride*, strain SKT-3 (FERM P-17021); B2.116 *Trichoderma gamsii* (formerly *T. viride*), strain ICC080 (IMI CC 392151 CABI, e.g. BioDerma by AGROBIOSOL DE MEXICO, S.A. DE C.V.); B2.117 *Trichoderma harzianum*, strain DB 103 (e.g. T-Gro 7456 by Dagutat Biolab); B2.118 *Trichoderma polysporum*, strain IMI 206039 (e.g. Binab TF WP by BINAB Bio-Innovation AB, Sweden); B2.119 *Trichoderma stromaticum* (e.g. Tricovab by Ceplac; Brazil); B2.120 *Tsukamurella paurometabola*, strain C-924 (e.g. HeberNem®); B2.121 *Ulocladium oudemansii*, in particular strain HRU3 (e.g. Botry-Zen® by Botry-Zen Ltd, NZ); B2.122 *Verticillium albo-atrum* (formerly *V. dahliae*), strain WCS850 (CBS 276.92; e.g. Dutch Trig by Tree Care Innovations); B2.123 *Aschersonia aleyrodis*; B2.124 *Beauveria brongniartii* (e.g. Beaupro from Andermatt Biocontrol AG); B2.125 *Conidiobolus obscurus*; B2.126 *Entomophthora virulenta* (e.g. Vektor from Ecomic); B2.127 *Lagenidium giganteum*; B2.128 *Metarhizium flavoviride*; B2.129 *Mucor haemelis* (e.g. BioAvard from Indore Biotech Inputs & Research); B2.130 *Pandora delphacis*; B2.131 *Sporothrix insectorum* (e.g. *Sporothrix* Es from Biocerto; BR); B2.132 *Zoophtora radicans*; B2.133 *Fusarium solani*, strain Fs5; B2.134 *Hirsutella rhossiliensis*; B2.135 *Monacrosporium drechsleri*; B2.136 *Monacrosporium gephyropagum*; B2.137 *Nematoctonus geogenius*; B2.138 *Nematoctonus leiosporus*; B2.139 *Neocosmospora vasinfecta*; B2.140 *Paraglomus* sp, in particular *Paraglomus brasilianum*; B2.141 *Pochonia chlamydosporia* (also known as *Vercillium chlamydosporium*), in particular var *catenulata* (IMI SD 187; e.g. KlamiC from The National Center of Animal and Plant Health (CENSA); CU); B2.142 *Stagonospora heteroderae;* B2.143 *Glomus aggregatum*; B2.144 *Glomus clarum*; B2.145 *Glomus deserticola*; B2.146 *Glomus etunicatum*; B2.147 *Glomus intraradices*; B2.148 *Glomus monosporum*; B2.149 *Glomus mosseae*; B2.150 *Laccaria bicolor*; B2.151 *Rhizopogon luteolus*; B2.152 *Rhizopogon tinctorus*; B2.153 *Rhizopogon villosulus*; B2.154 *Scleroderma cepa*; B2.155 *Suillus granulatus*; B2.156 *Suillus punctatapies*; B2.157 *Trichoderma harzianum*, strain 1295-22; B2.158 *Colletotrichum gloeosporioides*, strain ATCC 20358 (e.g. Collego (aka LockDown by Agriultural Research Initiatives); B2.159 *Stagonospora atriplici*; B2.160 *Cylindrocarpon heteronema*; B2.161 *Exophiala jeanselmei*; B2.162 *Exophilia pisciphila*; B2.163 *Fusarium aspergilus*; B2.164 *Gigaspora margarita*; B2.165 *Gigaspora monosporum*; B2.166 *Glomus brasilianum*; B2.167 *Laccaria laccata;* B2.168 *Ophiostoma piliferum*, strain D97 (e.g. Sylvanex); B2.169 *Sarcocystis singaporensis*; B2.170 *Trichoderma asperellum*, strain T34 (e.g. T34 Biocontrol by Bioncontrol Technologies, ES); B2.171 *Meristacrum asterospermum*; B2.172 *Muscodor albus*, in particular strain 620 (Accession No. NRRL 30547; described in US 2012/0114610); B2.173 *Nomuraea rileyi*, in particular strain SA86101 (cf. Braz. Arch. Biol. Technol. Vol. 46, No. 1, pp 13-18); B2.174 *Nomuraea rileyi*, in particular strain GU87401 (cf. Braz. Arch. Biol. Technol. Vol. 46, No. 1, pp 13-18); B2.175 *Nomuraea rileyi*, in particular strain SR86151 (cf. Braz. Arch. Biol. Technol. Vol. 46, No. 1, pp 13-18); B2.176 *Nomuraea rileyi*, in particular strain CG128 (cf. Braz. Arch. Biol. Technol. Vol. 46, No. 1, pp 13-18); B2.177 *Nomuraea rileyi*, in particular strain VA9101 (cf. Braz. Arch. Biol. Technol. Vol. 46, No. 1, pp 13-18); B2.178 *Trichoderma album* (product known as e.g. Bio-Zeid) and B2.179 mixtures of *Trichoderma asperellum* strain ICC 012 and *Trichoderma gamsii* strain ICC 080 (product known as e.g. BIO-TAM™ from Bayer CropScience LP, US).

In some embodiments of the invention such biological control agents which are summarized under the term fungi according to the invention include: B2.2.1 *Coniothyrium minitans*, strain CON/M/91-8 (Accession No. DSM-9660); B2.2.2 *Metschnikowia fructicola*, strain NRRL Y-30752; B2.2.4 *Muscodor albus*, strain QST 20799 (Accession No.

NRRL 30547); B2.2.8 *Paecilomyces lilacinus*, spores of *P. lilacinus* strain 251 (AGAL 89/030550); B2.2.26 *Phlebiopsis* (or *Phlebia* or *Peniophora*) *gigantea*, strain VRA 1835 (ATCC Accession No. 90304); B2.2.27 *Phlebiopsis* (or *Phlebia* or *Peniophora*) *gigantea*, strain VRA 1984 (DSM16201); B2.2.28 *Phlebiopsis* (or *Phlebia* or *Peniophora*) *gigantea*, strain VRA 1985 (DSM16202); B2.2.29 *Phlebiopsis* (or *Phlebia* or *Peniophora*) *gigantea*, strain VRA 1986 (DSM16203); B2.2.30 *Phlebiopsis* (or *Phlebia* or *Peniophora*) *gigantea*, strain FOC PG B20/5 (IMI390096); B2.2.31 *Phlebiopsis* (or *Phlebia* or *Peniophora*) *gigantea*, strain FOC PG SP log 6 (IMI390097); B2.2.32 *Phlebiopsis* (or *Phlebia* or *Peniophora*) *gigantea*, strain FOC PG SP log 5 (IMI390098); B2.2.33 *Phlebiopsis* (or *Phlebia* or *Peniophora*) *gigantea*, strain FOC PG BU3 (IMI390099); B2.2.34 *Phlebiopsis* (or *Phlebia* or *Peniophora*) *gigantea*, strain FOC PG BU4 (IMI390100); B2.2.35 *Phlebiopsis* (or *Phlebia* or *Peniophora*) *gigantea*, strain FOC PG 410.3 (IMI390101); B2.2.36 *Phlebiopsis* (or *Phlebia* or *Peniophora*) *gigantea*, strain FOC PG 97/1062/116/1.1 (IMI390102); B2.2.37 *Phlebiopsis* (or *Phlebia* or *Peniophora*) *gigantea*, strain FOC PG B22/SP1287/3.1 (IMI390103); B2.2.38 *Phlebiopsis* (or *Phlebia* or *Peniophora*) *gigantea*, strain FOC PG SH1 (IMI390104); B2.2.39 *Phlebiopsis* (or *Phlebia* or *Peniophora*) *gigantea*, strain FOC PG B22/SP1190/3.2 (IMI390105); B2.2.55 *Trichoderma harzianum*, strain KD; B2.2.58 *Trichoderma virens* (also known as *Gliocladium virens*), strain GL-21; B2.2.86 *Trichoderma lignorum*, strain TL-0601; B2.2.88 *Penicillium bilaii*, strain ATCC 22348; B2.2.96 *Aureobasidium pullulans*; Blastospores of strain DSM14940; B2.2.97 *Aureobasidium pullulans*; Blastospores of strain DSM14941; B2.2.98 *Aureobasidium pullulans*, mixtures of blastospores of strains DSM14940 and DSM14941; B2.2.121 *Ulocladium oudemansii*, strain HRU3; B2.2.140 *Paraglomus* sp, *Paraglomus brasilianum*; B2.2.141 *Pochonia chlamydosporia* (also known as *Vercillium chlamydosporium*); var. *catenulata* (IMI SD 187); B2.2.172 *Muscodor albus*, strain 620 (Accession No. NRRL 30547; B2.2.173 *Nomuraea rileyi*, strain SA86101; B2.2.174 *Nomuraea rileyi*, strain GU87401; B2.2.175 *Nomuraea rileyi*, strain SR86151; B2.2.176 *Nomuraea rileyi*, strain CG128 and B2.2.177 *Nomuraea rileyi*, strain VA9101.

According to the invention examples of protozoas to be used or employed according to the invention are (the numbering is used throughout the complete following description of the invention): B3.1 *Nosema locustae* (product known as e.g. NoloBait); B3.2 *Thelohania solenopsis* and B3.3 *Vairimorpha* spp.

According to the invention examples of viruses to be used or employed according to the invention are (the numbering is used throughout the complete following description of the invention): B4.1 *Adoxophyes orana* (summer fruit *tortrix*) granulosis virus (GV); (product known as e.g. BIOFA-Capex®); B4.2 *Agrotis segetum* (turnip moth) nuclear polyhedrosis virus (NPV); B4.3 *Anticarsia gemmatalis* (Woolly pyrol moth) mNPV (product known as e.g. Polygen); B4.4 *Autographa californica* (Alfalfa Looper) mNPV (product known as e.g. VPN80 from *Agricola* El Sol); B4.5 *Biston suppressaria* (tea looper) NPV; B4.6 *Bombyx mori* (silkworm) NPV; B4.7 *Clyptophlebia leucotreta* (false codling moth) GV (product known as e.g. Cryptex); B4.8 *Cydia pomonella* (Codling moth) granulosis virus (GV) (product known as e.g. Madex Plus); B4.9 *Dendrolimus punctatus* (Masson pine moth) CPV; B4.10 *Helicoverpa annigera* NPV (product known as e.g. AgBiTech-ViVUS Max); B4.11 *Helicoverpa* (previously *Heliothis*) *zea* (corn earworm) NPV (product known as e.g. Elcar); B4.12 *Leucoma salicis* (satin moth) NPV; B4.13 *Lymantria dispar* (gypsy moth) NPV (product known as e.g. Gypcheck); B4.14 *Neodiprion abietis* (balsam-fir sawfly) NPV (product known as e.g. Abietiv); B4.15 *Neodiprion lecontei* (red-headed pinesawfly) NPV (product known as e.g. Lecontvirus); B4.16 *Neodiprion sertifer* (Pine sawfly) NPV (product known as e.g. Neocheck-S); B4.17 *Orgyia pseudotsugata* (Douglas-fir tussock moth) NPV (product known as e.g. Virtuss); B4.18 *Phthorimaea operculella* (tobacco leaf miner) GV (product known as e.g. Matapol); B4.19 *Pieris rapae* (small white) GV; B4.20 *Plutella xylostella* (diamondback moth) GV (product known as e.g. Plutec); B4.21 *Spodoptera albula* (gray-streaked armywom moth) mNPV (product known as e.g. VPN 82); B4.22 *Spodoptera exempta* (true armyworm) mNPV (product known as e.g. Spodec); B4.23 *Spodoptera exigua* (sugarbeet armyworm) mNPV (product known as e.g. Spexit from Andermatt Biocontrol); B4.24 *Spodoptera frugiperda* (fall armyworm) mNPV (product known as e.g. Baculovirus VPN); B4.25 *Spodoptera littoralis* (tobacco cutworm) NPV (procucts known as Spodoptrin from NPP Calliope France); and B4.26 *Spodoptera litura* (oriental leafworm moth) NPV (product known as e.g. Littovir).

According to the invention examples of nematodes to be used or employed according to the invention are (the numbering is used throughout the complete following description of the invention): B5.1 *Abbreviata caucasica*; B5.2 *Acuaria* spp.; B5.3 *Agamermis decaudata*; B5.4 *Allantonema* spp.; B5.5 *Amphimermis* spp.; B5.6 *Beddingia* (=*Deladenus*) *siridicola*; B5.7 *Bovienema* spp.; B5.7a *Cameronia* spp.; B5.8 *Chitwoodiella ovofilamenta*; B5.9 *Contortylenchus* spp.; B5.10 *Culicimermis* spp.; B5.11 *Diplotriaena* spp.; B5.12 *Empidomermis* spp.; B5.13 *Filipjevimeris leipsandra*; B5.14 *Gastromermmis* spp.; B5.15 *Gongylonema* spp.; B5.16 *Gynopoecilia pseudovipara*; B5.17 *Heterorhabditis* spp., in particular *Heterorhabditis bacteriophora* (product known as e.g. B-Green); or *Heterorhabditis baujardi*, or *Heterorhabditis heliothidis* (product known as e.g. Nematon); or *Heterorhabditis indica*, *Heterorhabditis marelatus*, *Heterorhabditis megidis*, *Heterorhabditis zealandica*; B5.18 *Hexamermis* spp.; B5.19 *Hydromermis* spp.; B5.20 *Isomermis* spp.; B5.21 *Limnomermis* spp.; B5.22 *Maupasina weissi*; B5.23 *Mermis nigrescens*; B5.24 *Mesomermis* spp.; B5.25 *Neomesomermis* spp.; B5.26 *Neoparasitylenchus rugulosi*; B5.27 *Octomyomermis* spp.; B5.28 *Parasitaphelenchus* spp.; B5.29 *Parasitorhabditis* spp.; B5.30 *Parasitylenchus* spp.; B5.31 *Perutilimermis culicis*; B5.32 *Phasmarhabditis hermaphrodita*; B5.33 *Physaloptera* spp.; B5.34 *Protrellatus* spp.; B5.35 *Pterygodermatites* spp.; B5.36 *Romanomermis* spp.; B5.37 *Seuratum cadarachense*; B5.38 *Sphaerulariopsis* spp.; B5.39 *Spirura guianensis*, B5.40 *Steinernema* spp. (=Neoaplectana spp.), in particular *Steinernema carpocapsae* (product known as e.g. Biocontrol); or *Steinernema feltiae* (=Neoaplectana carpocapsae); (product known as e.g. Nemasys®); or *Steinernema glaseri* (procucts known as Biotopia); or *Steinernema kraussei* (product known as e.g. Larvesure); or *Steinernema riobrave* (product known as e.g. Biovector); or *Steinernema scapterisci* (product known as e.g. Nematac S); or *Steinernema scarabaei*, or *Steinernema siamkayai*; B5.41 *Strelkovimermis peterseni*; B5.42 *Subulura* spp.; B5.43 *Sulphuretylenchus elongatus* and B5.44 *Tetrameres* spp The term "proteins or secondary metabolite" refers to any compound, substance or byproduct of a fermentation of a microorganism that has pesticidal activity. The definition comprises any compound, substance or byproduct of a fermentation of a microorganism that has fungicidal activity. Examples of such proteins or secondary metabolites to be used or employed according to the invention are (the numbering is used throughout the complete following description of the invention): B6.1 Harpin (isolated by *Erwinia amylovora*, product known as e.g. Harp-N-Tek™, Messenger®, Employ™, ProAct™); B6.2 terpene constituents of extract of *Chenopodium ambrosioides* near *ambrosioides* as synthetically manufactured containing a mixture of three terpenes, i.e. α-terpinene, p-cymene and limonene, as pesticidally active ingredients (product known as e.g. Requiem® from Bayer CropScience LP, US).

In some embodiments of the invention such biological control agents which are summarized under the term proteins or secondary metabolites according to the invention comprise B6.6.2 terpene constituents of extract of *Chenopodium ambrosioides* near *ambrosioides* as synthetically manufactured containing a mixture of three terpenes, i.e. α-terpinene, p-cymene and limonene, as pesticidally active ingredients.

Unless indicated otherwise, the embodiments described below for the compositions and/or formulations disclosed herein are also applicable to respective embodiments of other aspects disclosed herein.

According to the present invention the biological control agents (B) are particularly selected from the group consisting of:
B1. bacteria,
B2. fungi,
B6. proteins or secondary metabolites.

Preferred are biological control agents selected from the group of bacteria consisting of B1.1.1 *Bacillus subtilis*, strain QST713/AQ713 (Accession No. NRRL B-21661); B1.2 *Bacillus subtilis* strain AQ153 (Accession No. NRRL 55614); B1.3 *Bacillus* sp. strain AQ175 (ATCC Accession No. 55608); B1.4 *Bacillus* sp. strain AQ177 (ATCC Accession No. 55609); B1.5 *Bacillus* sp. strain AQ178 (ATCC Accession No. 53522); B1.1.6 *Bacillus pumilus*, strain QST2808 (Accession No. NRRL B-30087); B1.1.7 *Bacillus pumilus*, strain GB34; B1.8 *Bacillus thuringiensis* strain AQ52 (Accession No. NRRL B-21619); B1.1.9 *Streptomyces* sp., strain having Accession No. NRRL B-30145; B1.1.10 *Streptomyces galbus* (=*Streptomyces griseoviridis*), strain QST 6047 (Accession No. NRRL B-30232); B1.1.11 *Bacillus chitinosporus*, strain AQ746 (Accession No. NRRL B-21618); B1.12 *Bacillus mycoides*, strain AQ726 (having Accession No. NRRL B-21664); B1.1.13 *Bacillus pumilus*, strain AQ717 (having Accession No. NRRL B21662); B1.1.14 *Bacillus subtilis*, strain AQ743 (having Accession No. NRRL B-21665); B1.15 *Rhodococcus globerulus* strain AQ719 (Accession No. NRRL B21663); B1.1.16 *Bacillus thuringiensis* subsp. *aizawai*, strain ABTS-1857 (SD-1372); B1.1.17 *Bacillus firmus*, strain CNMC I-1582; B1.1.18 *Bacillus subtilis*, strain AQ30002, (Accession No. NRRL B-50421); B1.1.19 *Bacillus subtilis*, strain AQ30004 (Accession No. NRRL B-50455); B1.20 *Bacillus amyloliquefaciens*, strain D747; B1.1.21 *Bacillus pumilus*, strain BU F-33; B1.22 *B. subtilis* var. *amyloliquefaciens* strain FZB24; B1.1.23 *Paenibacillus polymyxa*, strain AC-1; B1.24 *Pseudomonas proradix*, B1.25 *Bacillus amyloliquefaciens* strain MBI 600; B1.26 *Bacillus amyloliquefaciens* strain GB03; B1.27 *Bacillus amyloliquefaciens* strain DB 101; B1.28 *Bacillus amyloliquefaciens* strain DB 102; B1.29 *Bacillus amyloliquefaciens* isolate B246; B1.1.30 *Bacillus licheniformis*, strain SB3086; B1.1.31 *Pseudomonas syringae*, strain MA-4, B1.32 *Pseudomonas syringae* strain 742RS; B1.1.33 *Pseudomonas fluorescens*, strain 1629RS; B1.1.34 *Streptomyces galbus* (*Streptomyces griseoviridis*), strain K61 (Accession No. DSM 7206); B1.1.35 *Streptomyces lydicus*, strain WYEC108; B1.1.36 *Agrobacterium radiobacter*, strain K84; B1.37 *Agrobacterium radiobacter* strain K1026; B1.38 *Bacillus lentimorbus*; B1.39 *Bacillus mycoides*, isolate J.; B1.1.40 *Bacillus sphaericus*, Serotype H5a5b strain 2362; B1.41 *Bacillus thuringiensis* subsp. *kurstaki* strain BMP 123 from Becker Microbial Products, IL; B1.1.42 *Bacillus thuringiensis* subsp. *aizawai*, serotype H-7; B1.43 *Bacillus thuringiensis* subsp. *kurstaki* strain HD-1; B1.44 *Bacillus thuringiensis* subsp. *tenebrionis* strain NB 176; B1.45 *Bacillus thuringiensis* var. *japonensis* strain Buibui; B1.1.46 *Burkholderia* spp., strain A396 (Accession No. NRRL B-50319); B1.1.47 *Chromobacterium subtsugae*, strain PRAA4-1T (MBI-203); B1.48 *Paenibacillus popilliae* (formerly *Bacillus popilliae*); B1.49 *Xenorhabdus luminescens*; B1.50 *Xenorhabdus nematophila*; B1.1.51 *Bacillus thuringiensis* subspecies *israelensis* (serotype H-14); B1.1.52 *Bacillus amyloliquefaciens*, strain FZB42; B1.53 *Bacillus cereus*; B1.54 spores of *Bacillus cereus* strain CNCM I-1562; B1.55 *Bacillus laterosporus* (also known as *Brevibacillus laterosporus*); B1.56 *Bacillus megaterium*, strain YFM3.25; B1.57 *Bacillus mojavensis*, strain SR11 (CECT-7666); B1.58 *Bacillus nematocida*; B1.59 *Pasteuria nishizawae*; B1.60 *Pasteuria penetrans* (formerly *Bacillus penetrans*); B1.61 *Pasteuria usgae*; B1.62 compositions comprising nematicidal *Streptomycete* sp., such as *Streptomyces lydicus*; B1.63 compositions comprising nematicidal *Streptomycete* sp., such as *Streptomyces saraceticus*; B1.1.64 *Bacillus amyloliquefaciens*, strain IN937a; B1.1.65 *Bacillus cereus*, strain BP01 (ATCC Accession No. 55675); B1.66 *Bradyrhizobium japonicum*; B1.1.67 *Delftia acidovorans*, strain RAY209; B1.68 *Lactobacillus* sp.; B1.1.69 *Pseudomonas aeruginosa*, strain PN1; B1.1.70 *Rhizobium leguminosarum*; Bv. *viceae* strain Z25 (Accession No. CECT 4585); B1.1.71 *Streptomyces acidiscabies*, strain RL-110T.

Preferred are biological control agents selected from the group of fungi consisting of B2.2.1 *Coniothyrium minitans*, strain CON/M/91-8 (Accession No. DSM-9660); B2.2.2 *Metschnikowia fructicola*, strain NRRL Y-30752; B2.3 *Microsphaeropsis ochracea*; B2.2.4 *Muscodor albus*, strain QST 20799 (Accession No. NRRL 30547); B2.5 *Trichoderma atroviride*, strain SC1; B2.6 *Trichoderma harzianum rifai* strain KRL-AG2 (also known as strain T-22, /ATCC Accession No. 208479); B2.7 *Muscodor roseus* strain A3-5 (Accession No. NRRL 30548); B2.2.8 *Paecilomyces lilacinus*, spores of *P. lilacinus* strain 251 (AGAL 89/030550); B2.9 *Trichoderma koningii*; B2.10 *Talaromyces flavus*, strain V117b; B2.11 *Trichoderma atroviride*, strain no. V08/002387; B2.12 *Trichoderma atroviride*, strain no. NMI No. V08/002388; B2.13 *Trichoderma atroviride*, strain no. NMI No. V08/002389; B2.14 *Trichoderma atroviride*, strain no. NMI No. V08/002390; B2.15 *Trichoderma harzianum*, strain ITEM 908; B2.16 *Pseudozyma aphidis*; B2.17 *Pseudozyma aphidis* (from Yissum Research Development Company of the Hebrew University of Jerusalem); B2.18 *Arthrobotrys dactyloides*; B2.19 *Arthrobotrys oligospora*; B2.20 *Arthrobotrys superba*; B2.21 *Aspergillus flavus*, strain NRRL 21882; B2.22 *Aspergillus flavus*, strain AF36; B2.23 *Cryptococcus albidus*; B2.24 *Cryptococcus flavescens*, strain 4C (Accession No. NRRL Y-50379); B2.25 *Gliocladium roseum*, strain 321U from W.F. Stoneman Company LLC; B2.2.26 *Phlebiopsis* (or *Phlebia* or *Peniophora*) *gigantea*, strain VRA 1835 (ATCC Accession No. 90304); B2.2.27 *Phlebiopsis* (or *Phlebia* or *Peniophora*) *gigantea*, strain VRA 1984

(DSM16201); B2.2.28 *Phlebiopsis* (or *Phlebia* or *Peniophora*) *gigantea*, strain VRA 1985 (DSM16202); B2.2.29 *Phlebiopsis* (or *Phlebia* or *Peniophora*) *gigantea*, strain VRA 1986 (DSM16203); B2.2.30 *Phlebiopsis* (or *Phlebia* or *Peniophora*) *gigantea*, strain FOC PG B20/5 (IMI390096); B2.2.31 *Phlebiopsis* (or *Phlebia* or *Peniophora*) *gigantea*, strain FOC PG SP log 6 (IMI390097); B2.2.32 *Phlebiopsis* (or *Phlebia* or *Peniophora*) *gigantea*, strain FOC PG SP log 5 (IMI390098); B2.2.33 *Phlebiopsis* (or *Phlebia* or *Peniophora*) *gigantea*, strain FOC PG BU3 (IMI390099); B2.2.34 *Phlebiopsis* (or *Phlebia* or *Peniophora*) *gigantea*, strain FOC PG BU4 (IMI390100); B2.2.35 *Phlebiopsis* (or *Phlebia* or *Peniophora*) *gigantea*, strain FOC PG 410.3 (IMI390101); B2.2.36 *Phlebiopsis* (or *Phlebia* or *Peniophora*) *gigantea*, strain FOC PG 97/1062/116/1.1 (IMI390102); B2.2.37 *Phlebiopsis* (or *Phlebia* or *Peniophora*) *gigantea*, strain FOC PG B22/SP1287/3.1 (IMI390103); B2.2.38 *Phlebiopsis* (or *Phlebia* or *Peniophora*) *gigantea*, strain FOC PG SH1 (IMI390104); B2.2.39 *Phlebiopsis* (or *Phlebia* or *Peniophora*) *gigantea*, strain FOC PG B22/SP1190/3.2 (IMI390105); B2.40 *Pythium oligandrum*, strain DV74 or M1 (ATCC 38472); B2.41 *Saccharomyces cerevisae*, strain CNCM No. 1-3936 (from Lesaffre et Compagnie, FR); B2.42 *Saccharomyces cerevisae*, strain CNCM No. 1-3937 (from Lesaffre et Compagnie, FR); B2.43 *Saccharomyces cerevisae*, strain CNCM No. 1-3938 (from Lesaffre et Compagnie, FR); B2.44 *Saccharomyces cerevisae*, strain CNCM No. 1-3939 (from Lesaffre et Compagnie, FR); B2.45 *Scleroderma citrinum*; B2.46 *Trichoderma asperellum*, strain ICC 012 from Isagro; B2.47 *Trichoderma asperellum*, strain SKT-1; B2.48 *Trichoderma atroviride*, strain CNCM 1-1237; B2.49 *Trichoderma atroviride*, strain LC52; B2.50 *Trichoderma atroviride*, strain ATCC 20476 (IMI 206040); B2.51 *Trichoderma atroviride*, strain T11 (IMI352941/CECT20498); B2.52 *Trichoderma harmatum*; B2.53 *Trichoderma harzianum*; B2.54 *Trichoderma harzianum rifai* T39; B2.2.55 *Trichoderma harzianum*, strain KD, B2.56 *Trichoderma harzianum*, strain KD; B2.57 *Trichoderma harzianum*, strain TH35; B2.2.58 *Trichoderma virens* (also known as *Gliocladium virens*), strain GL-21; B2.59 *Trichoderma viride*, strain TV1( ); B2.60 *Beauveria bassiana*, strain ATCC 74040; B2.61 *Beauveria bassiana* strain GHA (ATCC Accession No. 74250); B2.62 *Beauveria bassiana* strain ATP02 (Accession No. DSM 24665); B2.63 *Beauveria bassiana* strain CG 716; B2.64 *Hirsutella citrifomris*; B2.65 *Hirsutella thompsonii*; B2.66 *Lecanicillium lecanii* (formerly known as *Verticillium lecanii*) conidia of strain KV01; B2.67 *Lecanicillium lecanii* (formerly known as *Verticillium lecanii*) conidia of strain DAOM198499; B2.68 *Lecanicillium lecanii* (formerly known as *Verticillium lecanii*) conidia of strain DAOM216596; B2.69 *Lecanicillium muscarium* (formerly *Verticillium lecanii*), strain VE 6/CABI(=IMI) 268317/CBS102071/ARSEF5128; B2.71 *Metarhizium anisopliae*, strain F52 (DSM3884/ATCC 90448); B2.72 *Metarhizium anisopliae* var. *acridum*; B2.73 *Metarhizium anisopliae* var. *acridum* isolate IMI 330189 (ARSEF7486); B2.74 *Nomuraea rileyi*; B2.75 *Paecilomyces fumosoroseus* (new: *Isaria fumosorosea*), strain apopka 97; B2.76 *Paecilomyces fumosoroseus* (new: *Isaria fumosorosea*) strain FE 9901; B2.77 *Harposporium anguillullae*; B2.78 *Hirsutella minnesotensis*; B2.79 *Monacrosporium cionopagum*; B2.80 *Monacrosporium psychrophilum*; B2.81 *Myrothecium verrucaria*, strain AARC-0255; B2.82 compositions comprising the fungus *Paecilomyces lilacinus*; B2.83 *Paecilomyces variotii*, strain Q-09; B2.84 compositions comprising the bacterium *Pasteuria* including *Pasteuria usgae*; B2.85 *Stagonospora phaseoli*; B2.2.86 *Trichoderma lignorum*, strain TL-0601; B2.87 *Penicillium bilaii*, strain ATCC 22348; B2.2.88 *Penicillium bilaii*, strain ATCC 22348; B2.89 *Rhizopogon amylopogon*; B2.90 *Rhizopogon fulvigleba*; B2.91 *Trichoderma harzianum*, strain TSTh20; B2.92 *Phoma macrostroma*, strain 94-44B; B2.93 *Sclerotinia minor*, strain IMI 344141.

Preferred are biological control agents selected from the group of proteins or secondary metabolite consisting of: B6.6.2 terpene constituents of extract of *Chenopodium ambrosioides* near *ambrosioides* as synthetically manufactured containing a mixture of three terpenes, i.e. α-terpinene, p-cymene and limonene, as pesticidally active ingredients Particularly preferred are biological control agents selected from the group of bacteria consisting of B1.1.1 *Bacillus subtilis*, strain QST713/AQ713 (Accession No. NRRL B-21661); B1.2 *Bacillus subtilis* strain AQ153 (Accession No. NRRL 55614); B1.3 *Bacillus* sp. strain AQ175 (ATCC Accession No. 55608); B1.4 *Bacillus* sp. strain AQ177 (ATCC Accession No. 55609); B1.5 *Bacillus* sp. strain AQ178 (ATCC Accession No. 53522); B1.1.6 *Bacillus pumilus*, strain QST2808 (Accession No. NRRL B-30087); B1.1.7 *Bacillus pumilus*, strain GB34; B1.8 *Bacillus thuringiensis* strain AQ52 (Accession No. NRRL B-21619); B1.1.9 *Streptomyces* sp., strain having Accession No. NRRL B-30145; B1.1.10 *Streptomyces galbus* (=*Streptomyces griseoviridis*), strain QST 6047 (Accession No. NRRL B-30232); B1.1.11 *Bacillus chitinosporus*, strain AQ746 (Accession No. NRRL B-21618); B1.12 *Bacillus mycoides*, strain AQ726 (having Accession No. NRRL B-21664); B1.1.13 *Bacillus pumilus*, strain AQ717 (having Accession No. NRRL B21662); B1.1.14 *Bacillus subtilis*, strain AQ743 (having Accession No. NRRL B-21665); B1.15 *Rhodococcus globerulus* strain AQ719 (Accession No. NRRL B21663); B1.1.16 *Bacillus thuringiensis* subsp. *aizawai*, strain ABTS-1857 (SD-1372); B1.1.17 *Bacillus firmus*, strain CNMC 1-1582; B1.1.18 *Bacillus subtilis*, strain AQ30002, (Accession No. NRRL B-50421); B1.1.19 *Bacillus subtilis*, strain AQ30004 (Accession No. NRRL B-50455.

Particularly preferred are biological control agents selected from the group of fungi consisting of B2.2.1 *Coniothyrium minitans*, strain CON/M/91-8 (Accession No. DSM-9660); B2.2.2 *Metschnikowia fructicola*, strain NRRL Y-30752; B2.3 *Microsphaeropsis ochracea*; B2.2.4 *Muscodor albus*, strain QST 20799 (Accession No. NRRL 30547); B2.5 *Trichoderma atroviride*, strain SC1; B2.6 *Trichoderma harzianum rifai* strain KRL-AG2 (also known as strain T-22, /ATCC Accession No. 208479); B2.7 *Muscodor roseus* strain A3-5 (Accession No. NRRL 30548); B2.2.8 *Paecilomyces lilacinus*, spores of *P. lilacinus* strain 251 (AGAL 89/030550); B2.9 *Trichoderma koningii*; B2.10 *Talaromyces flavus*, strain V117b; B2.11 *Trichoderma atroviride*, strain no. V08/002387; B2.12 *Trichoderma atroviride*, strain no. NMI No. V08/002388; B2.13 *Trichoderma atroviride*, strain no. NMI No. V08/002389; B2.14 *Trichoderma atroviride*, strain no. NMI No. V08/002390; B2.15 *Trichoderma harzianum*, strain ITEM 908.

Most preferred are biological control agents selected from the group of bacteria consisting of B1.1 *Bacillus subtilis*, in particular strain QST713/AQ713 (available as SERENADE MAX from Bayer CropScience LP, US, having NRRL Accession No. B-21661 and described in U.S. Pat. No. 6,060,051); B1.6 *Bacillus pumilus*, in particular strain QST2808 (available as Sonata® from Bayer CropScience LP, US, having Accession No. NRRL B-30087 and described in U.S. Pat. No. 6,245,551) and B1.18 *Bacillus*

*subtilis*, in particular strain AQ30002, (having Accession No. NRRL B-50421 and described in U.S. patent application Ser. No. 13/330,576).

Furthermore preferred are biological control agents selected from the group of bacteria consisting of B1.1.1 *Bacillus subtilis*, strain QST713/AQ713 (Accession No. NRRL B-21661); B1.1.6 *Bacillus pumilus*, strain QST2808 (Accession No. NRRL B-30087) and B1.1.18 *Bacillus subtilis*, strain AQ30002, (Accession No. NRRL B-50421).

The following combinations exemplify specific embodiments of the composition according to the present invention:
(I-1)+(B1.1), (I-1)+(B1.2), (I-1)+(B1.3), (I-1)+(B1.4), (I-1)+(B1.5), (I-1)+(B1.6), (I-1)+(B1.7), (I-1)+(B1.8), (I-1)+(B1.9), (I-1)+(B1.10), (I-1)+(B1.11), (I-1)+(B1.12), (I-1)+(B1.13), (I-1)+(B1.14), (I-1)+(B1.15), (I-1)+(B1.16), (I-1)+(B1.17), (I-1)+(B1.18), (I-1)+(B1.19), (I-1)+(B1.20), (I-1)+(B1.21), (I-1)+(B1.22), (I-1)+(B1.23), (I-1)+(B1.24), (I-1)+(B1.25), (I-1)+(B1.26), (I-1)+(B1.27), (I-1)+(B1.28), (I-1)+(B1.29), (I-1)+(B1.30), (I-1)+(B1.31), (I-1)+(B1.32), (I-1)+(B1.33), (I-1)+(B1.34), (I-1)+(B1.35), (I-1)+(B1.36), (I-1)+(B1.37), (I-1)+(B1.38), (I-1)+(B1.39), (I-1)+(B1.40), (I-1)+(B1.41), (I-1)+(B1.42), (I-1)+(B1.43), (I-1)+(B1.44), (I-1)+(B1.45), (I-1)+(B1.46), (I-1)+(B1.47), (I-1)+(B1.48), (I-1)+(B1.49), (I-1)+(B1.50), (I-1)+(B1.51), (I-1)+(B1.52), (I-1)+(B1.53), (I-1)+(B1.54), (I-1)+(B1.55), (I-1)+(B1.56), (I-1)+(B1.57), (I-1)+(B1.58), (I-1)+(B1.59), (I-1)+(B1.60), (I-1)+(B1.61), (I-1)+(B1.62), (I-1)+(B1.63), (I-1)+(B1.64), (I-1)+(B1.65), (I-1)+(B1.66), (I-1)+(B1.67), (I-1)+(B1.68), (I-1)+(B1.69), (I-1)+(B1.70), (I-1)+(B1.71), (I-1)+(B1.72), (I-1)+(B1.73), (I-1)+(B1.74), (I-1)+(B1.75), (I-1)+(B1.76), (I-1)+(B1.77), (I-1)+(B1.78), (I-1)+(B1.79), (I-1)+(B1.80), (I-1)+(B1.81), (I-1)+(B1.82), (I-1)+(B1.83), (I-1)+(B1.84), (I-1)+(B1.85), (I-1)+(B1.86), (I-1)+(B1.87), (I-1)+(B1.88), (I-1)+(B1.89), (I-1)+(B1.90), (I-1)+(B1.91), (I-1)+(B1.92), (I-1)+(B1.93), (I-1)+(B1.94), (I-1)+(B1.95), (I-1)+(B1.96), (I-1)+(B1.97), (I-1)+(B1.98), (I-1)+(B1.99), (I-1)+(B1.100), (I-1)+(B1.101), (I-1)+(B1.102), (I-1)+(B1.103), (I-1)+(B1.104), (I-1)+(B1.105), (I-1)+(B1.106), (I-1)+(B1.107), (I-1)+(B1.108), (I-1)+(B1.109), (I-1)+(B1.110), (I-1)+(B1.111), (I-1)+(B1.112), (I-1)+(B1.113), (I-1)+(B1.114), (I-1)+(B1.115), (I-1)+(B1.116), (I-1)+(B1.117), (I-1)+(B1.118), (I-1)+(B1.119), (I-1)+(B1.120), (I-1)+(B1.121), (I-1)+(B1.122), (I-1)+(B1.123), (I-1)+(B1.124), (I-1)+(B1.125), (I-1)+(B1.126), (I-1)+(B1.127), (I-1)+(B1.128), (I-1)+(B1.129), (I-1)+(B1.130), (I-1)+(B1.131), (I-1)+(B1.132), (I-1)+(B1.133), (I-1)+(B1.134), (I-1)+(B1.135), (I-1)+(B1.136), (I-1)+(B1.137), (I-1)+(B1.138), (I-1)+(B1.139), (I-1)+(B1.140), (I-1)+(B1.141), (I-1)+(B1.142), (I-1)+(B1.143), (I-1)+(B1.144), (I-1)+(B1.145), (I-1)+(B1.146), (I-1)+(B1.147), (I-1)+(B1.148), (I-1)+(B1.149), (I-1)+(B1.150), (I-1)+(B1.151), (I-1)+(B1.152), (I-1)+(B1.153), (I-1)+(B1.154), (I-1)+(B1.155), (I-1)+(B1.156), (I-1)+(B1.157), (I-1)+(B1.158), (I-1)+(B1.159), (I-1)+(B1.160), (I-1)+(B1.161), (I-1)+(B1.162), (I-1)+(B1.163), (I-1)+(B1.164), (I-1)+(B1.165), (I-1)+(B1.166), (I-1)+(B1.167), (I-1)+(B1.168), (I-1)+(B1.169), (I-1)+(B1.170), (I-1)+(B1.171), (I-1)+(B1.172), (I-1)+(B1.173), (I-1)+(B1.174), (I-1)+(B1.175), (I-1)+(B1.176), (I-1)+(B1.177), (I-1)+(B1.178), (I-1)+(B1.179), (I-1)+(B1.180), (I-1)+(B1.181), (I-1)+(B1.182), (I-1)+(B1.183), (I-1)+(B1.184), (I-1)+(B1.185), (I-1)+(B1.186), (I-1)+(B1.187), (I-1)+(B1.188), (I-1)+(B1.189), (I-1)+(B1.190), (I-1)+(B1.191), (I-1)+(B1.192), (I-1)+(B1.193), (I-1)+(B1.194), (I-1)+(B1.195), (I-1)+(B1.196), (I-1)+(B1.197), (I-1)+(B1.198), (I-1)+(B1.199), (I-1)+(B1.1.1), (I-1)+(B1.1.6), (I-1)+(B1.1.7), (I-1)+(B1.1.9), (I-1)+(B1.1.10), (I-1)+(B1.1.11), (I-1)+(B1.1.13), (I-1)+(B1.1.14), (I-1)+(B1.1.16), (I-1)+(B1.1.17), (I-1)+(B1.1.18), (I-1)+(B1.1.19), (I-1)+(B1.1.21), (I-1)+(B1.1.23), (I-1)+(B1.1.30), (I-1)+(B1.1.31), (I-1)+(B1.1.33), (I-1)+(B1.1.34), (I-1)+(B1.1.35), (I-1)+(B1.1.36), (I-1)+(B1.1.40), (I-1)+(B1.1.42), (I-1)+(B1.1.46), (I-1)+(B1.1.47), (I-1)+(B1.1.51), (I-1)+(B1.1.52), (I-1)+(B1.1.64), (I-1)+(B1.1.65), (I-1)+(B1.1.67), (I-1)+(B1.1.69), (I-1)+(B1.1.70), (I-1)+(B1.1.71), (I-1)+(B1.1.74), (I-1)+(B1.1.75), (I-1)+(B1.1.76), (I-1)+(B1.1.77), (I-1)+(B1.1.81), (I-1)+(B1.1.82), (I-1)+(B1.1.83), (I-1)+(B1.1.84), (I-1)+(B1.1.85), (I-1)+(B1.1.86), (I-1)+(B1.1.87), (I-1)+(B1.1.89), (I-1)+(B1.1.90), (I-1)+(B1.1.93), (I-1)+(B1.1.103), (I-1)+(B1.1.124), (I-1)+(B1.1.125), (I-1)+(B1.1.129), (I-1)+(B1.1.130), (I-1)+(B1.1.149), (I-1)+(B1.1.162), (I-1)+(B1.1.163), (I-1)+(B1.1.164), (I-1)+(B1.1.165), (I-1)+(B1.1.167), (I-1)+(B1.1.168), (I-1)+(B1.1.169), (I-1)+(B1.1.170), (I-1)+(B1.1.171), (I-1)+(B1.1.172), (I-1)+(B1.1.173), (I-1)+(B1.1.174), (I-1)+(B1.1.178), (I-1)+(B1.1.179), (I-1)+(B1.1.180), (I-1)+(B1.1.181), (I-1)+(B1.1.189), (I-1)+(B1.1.193), (I-1)+(B1.1.196), (I-1)+(B2.1), (I-1)+(B2.2), (I-1)+(B2.3), (I-1)+(B2.4), (I-1)+(B2.5), (I-1)+(B2.6), (I-1)+(B2.7), (I-1)+(B2.8), (I-1)+(B2.9), (I-1)+(B2.10), (I-1)+(B2.11), (I-1)+(B2.12), (I-1)+(B2.13), (I-1)+(B2.14), (I-1)+(B2.15), (I-1)+(B2.16), (I-1)+(B2.17), (I-1)+(B2.18), (I-1)+(B2.19), (I-1)+(B2.20), (I-1)+(B2.21), (I-1)+(B2.22), (I-1)+(B2.23), (I-1)+(B2.24), (I-1)+(B2.25), (I-1)+(B2.26), (I-1)+(B2.27), (I-1)+(B2.28), (I-1)+(B2.29), (I-1)+(B2.30), (I-1)+(B2.31), (I-1)+(B2.32), (I-1)+(B2.33), (I-1)+(B2.34), (I-1)+(B2.35), (I-1)+(B2.36), (I-1)+(B2.37), (I-1)+(B2.38), (I-1)+(B2.39), (I-1)+(B2.40), (I-1)+(B2.41), (I-1)+(B2.42), (I-1)+(B2.43), (I-1)+(B2.44), (I-1)+(B2.45), (I-1)+(B2.46), (I-1)+(B2.47), (I-1)+(B2.48), (I-1)+(B2.49), (I-1)+(B2.50), (I-1)+(B2.51), (I-1)+(B2.52), (I-1)+(B2.53), (I-1)+(B2.54), (I-1)+(B2.55), (I-1)+(B2.56), (I-1)+(B2.57), (I-1)+(B2.58), (I-1)+(B2.59), (I-1)+(B2.60), (I-1)+(B2.61), (I-1)+(B2.62), (I-1)+(B2.63), (I-1)+(B2.64), (I-1)+(B2.65), (I-1)+(B2.66), (I-1)+(B2.67), (I-1)+(B2.68), (I-1)+(B2.69), (I-1)+(B2.71), (I-1)+(B2.72), (I-1)+(B2.73), (I-1)+(B2.74), (I-1)+(B2.75), (I-1)+(B2.76), (I-1)+(B2.77), (I-1)+(B2.78), (I-1)+(B2.79), (I-1)+(B2.80), (I-1)+(B2.81), (I-1)+(B2.82), (I-1)+(B2.83), (I-1)+(B2.84), (I-1)+(B2.85), (I-1)+(B2.86), (I-1)+(B2.87), (I-1)+(B2.88), (I-1)+(B2.89), (I-1)+(B2.90), (I-1)+(B2.91), (I-1)+(B2.92), (I-1)+(B2.93), (I-1)+(B2.94), (I-1)+(B2.95), (I-1)+(B2.96), (I-1)+(B2.97), (I-1)+(B2.98), (I-1)+(B2.99), (I-1)+(B2.100), (I-1)+(B2.101), (I-1)+(B2.102), (I-1)+(B2.103), (I-1)+(B2.104), (I-1)+(B2.105), (I-1)+(B2.106), (I-1)+(B2.107), (I-1)+(B2.108), (I-1)+(B2.109), (I-1)+(B2.110), (I-1)+(B2.111), (I-1)+(B2.112), (I-1)+(B2.113), (I-1)+(B2.114), (I-1)+(B2.115), (I-1)+(B2.116), (I-1)+(B2.117), (I-1)+(B2.118), (I-1)+(B2.119), (I-1)+(B2.120), (I-1)+(B2.121), (I-1)+(B2.122), (I-1)+(B2.123), (I-1)+(B2.124), (I-1)+(B2.125), (I-1)+(B2.126), (I-1)+(B2.127), (I-1)+(B2.128), (I-1)+(B2.129), (I-1)+(B2.130), (I-1)+(B2.131), (I-1)+(B2.132), (I-1)+(B2.133), (I-1)+(B2.134), (I-1)+(B2.135), (I-1)+(B2.136), (I-1)+(B2.137), (I-1)+(B2.138), (I-1)+(B2.139), (I-1)+(B2.140), (I-1)+(B2.141), (I-1)+(B2.142), (I-1)+(B2.143), (I-1)+(B2.144), (I-1)+(B2.145), (I-1)+(B2.146), (I-1)+(B2.147), (I-1)+(B2.148), (I-1)+(B2.149), (I-1)+(B2.150), (I-1)+(B2.151), (I-1)+(B2.152), (I-1)+(B2.153), (I-1)+(B2.154), (I-1)+(B2.155), (I-1)+(B2.156), (I-1)+(B2.157), (I-1)+(B2.158), (I-1)+(B2.159), (I-1)+(B2.160), (I-1)+(B2.161), (I-1)+(B2.162), (I-1)+(B2.163), (I-1)+(B2.164), (I-1)+(B2.165), (I-1)+(B2.166), (I-1)+(B2.167), (I-1)+(B2.168), (I-1)+(B2.169), (I-1)+(B2.170), (I-1)+(B2.171), (I-1)+(B2.172), (I-1)+(B2.173), (I-1)+(B2.174), (I-1)+(B2.175), (I-1)+(B2.176), (I-1)+(B2.177), (I-1)+(B2.178), (I-1)+(B2.179), (I-1)+(B2.2.1), (I-1)+(B2.2.2), (I-1)+(B2.2.4), (I-1)+(B2.2.8), (I-1)+(B2.2.26), (I-1)+(B2.2.27), (I-1)+(B2.2.28), (I-1)+(B2.2.29), (I-1)+(B2.2.30), (I-1)+(B2.2.31), (I-1)+(B2.2.32), (I-1)+(B2.2.33), (I-1)+(B2.2.34), (I-1)+(B2.2.35), (I-1)+(B2.2.36), (I-1)+(B2.2.37), (I-1)+(B2.2.38), (I-1)+(B2.2.39), (I-1)+(B2.2.55), (I-1)+(B2.2.58), (I-1)+(B2.2.86), (I-1)+(B2.2.88), (I-1)+(B2.2.94), (I-1)+(B2.2.96), (I-1)+(B2.2.97), (I-1)+(B2.2.98), (I-1)+(B2.2.121), (I-1)+(B2.2.140), (I-1)+(B2.2.141), (I-1)+(B2.2.172), (I-1)+(B2.2.173), (I-1)+(B2.2.174), (I-1)+(B2.2.175), (I-1)+(B2.2.176), (I-1)+(B2.2.177), (I-1)+(B3.1), (I-1)+(B3.2), (I-1)+(B3.3), (I-1)+(B4.1), (I-1)+(B4.2), (I-1)+(B4.3), (I-1)+(B4.4), (I-1)+(B4.5), (I-1)+(B4.6), (I-1)+(B4.7), (I-1)+(B4.8), (I-1)+(B4.9), (I-1)+(B4.10), (I-1)+(B4.11), (I-1)+(B4.12), (I-1)+(B4.13), (I-1)+(B4.14), (I-1)+(B4.15), (I-1)+(B4.16), (I-1)+(B4.17), (I-1)+(B4.18), (I-1)+(B4.19), (I-1)+(B4.20), (I-1)+(B4.21), (I-1)+(B4.22), (I-1)+(B4.23), (I-1)+(B4.24), (I-1)+(B4.25), (I-1)+(B4.26), (I-1)+(B5.1), (I-1)+(B5.2), (I-1)+(B5.3), (I-1)+(B5.4), (I-1)+(B5.5), (I-1)+(B5.6), (I-1)+(B5.7), (I-1)+(B5.8), (I-1)+(B5.9), (I-1)+(B5.10), (I-1)+(B5.11), (I-1)+(B5.12), (I-1)+(B5.13), (I-1)+(B5.14), (I-1)+(B5.15), (I-1)+(B5.16), (I-1)+(B5.17), (I-1)+(B5.18), (I-1)+(B5.19), (I-1)+(B5.20), (I-1)+(B5.21), (I-1)+(B5.22), (I-1)+(B5.23), (I-1)+(B5.24), (I-1)+(B5.25), (I-1)+(B5.26), (I-1)+(B5.27), (I-1)+(B5.28), (I-1)+(B5.29), (I-1)+(B5.30), (I-1)+(B5.31), (I-1)+(B5.32), (I-1)+(B5.33), (I-1)+(B5.34), (I-1)+(B5.35), (I-1)+(B5.36), (I-1)+(B5.37), (I-1)+(B5.38), (I-1)+(B5.39), (I-1)+(B5.40), (I-1)+(B5.41), (I-1)+(B5.42), (I-1)+(B5.43), (I-1)+(B5.44), (I-1)+(B6.1), (I-1)+(B6.2), (I-1)+(B6.6.2), (I-2)+(B1.1), (I-2)+(B1.2), (I-2)+(B1.3), (I-2)+(B1.4), (I-2)+(B1.5), (I-2)+(B1.6), (I-2)+(B1.7), (I-2)+(B1.8), (I-2)+(B1.9), (I-2)+(B1.10), (I-2)+(B1.11), (I-2)+(B1.12), (I-2)+(B1.13), (I-2)+(B1.14), (I-2)+(B1.15), (I-2)+(B1.16), (I-2)+(B1.17), (I-2)+(B1.18), (I-2)+(B1.19), (I-2)+(B1.20), (I-2)+(B1.21), (I-2)+(B1.22), (I-2)+(B1.23), (I-2)+(B1.24), (I-2)+(B1.25), (I-2)+(B1.26), (I-2)+(B1.27), (I-2)+(B1.28), (I-2)+(B1.29), (I-2)+(B1.30), (I-2)+(B1.31), (I-2)+(B1.32), (I-2)+(B1.33), (I-2)+(B1.34), (I-2)+(B1.35), (I-2)+(B1.36), (I-2)+(B1.37), (I-2)+(B1.38), (I-2)+(B1.39), (I-2)+(B1.40), (I-2)+(B1.41), (I-2)+(B1.42), (I-2)+(B1.43), (I-2)+(B1.44), (I-2)+(B1.45), (I-2)+(B1.46), (I-2)+(B1.47), (I-2)+(B1.48), (I-2)+(B1.49), (I-2)+(B1.50), (I-2)+(B1.51), (I-2)+(B1.52), (I-2)+(B1.53), (I-2)+(B1.54), (I-2)+(B1.55), (I-2)+(B1.56), (I-2)+(B1.57), (I-2)+(B1.58), (I-2)+(B1.59), (I-2)+(B1.60), (I-2)+(B1.61), (I-2)+(B1.62), (I-2)+(B1.63), (I-2)+(B1.64), (I-2)+(B1.65), (I-2)+(B1.66), (I-2)+(B1.67), (I-2)+(B1.68), (I-2)+(B1.69), (I-2)+(B1.70), (I-2)+(B1.71), (I-2)+(B1.72), (I-2)+(B1.73), (I-2)+(B1.74), (I-2)+(B1.75), (I-2)+(B1.76), (I-2)+(B1.77), (I-2)+(B1.78), (I-2)+(B1.79), (I-2)+(B1.80), (I-2)+(B1.81), (I-2)+(B1.82), (I-2)+(B1.83), (I-2)+(B1.84), (I-2)+(B1.85), (I-2)+(B1.86), (I-2)+(B1.87), (I-2)+(B1.88), (I-2)+(B1.89), (I-2)+(B1.90), (I-2)+(B1.91), (I-2)+(B1.92), (I-2)+(B1.93), (I-2)+(B1.94), (I-2)+(B1.95), (I-2)+(B1.96), (I-2)+(B1.97), (I-2)+(B1.98), (I-2)+(B1.99), (I-2)+(B1.100), (I-2)+(B1.101), (I-2)+(B1.102), (I-2)+(B1.103), (I-2)+(B1.104), (I-2)+(B1.105), (I-2)+(B1.106), (I-2)+(B1.107), (I-2)+(B1.108), (I-2)+(B1.109), (I-2)+(B1.110), (I-2)+(B1.111), (I-2)+(B1.112), (I-2)+(B1.113), (I-2)+(B1.114), (I-2)+(B1.115), (I-2)+(B1.116), (I-2)+(B1.117), (I-2)+(B1.118), (I-2)+(B1.119), (I-2)+(B1.120), (I-2)+(B1.121), (I-2)+(B1.122), (I-2)+(B1.123), (I-2)+(B1.124), (I-2)+(B1.125), (I-2)+(B1.126), (I-2)+(B1.127), (I-2)+(B1.128), (I-2)+(B1.129), (I-2)+(B1.130), (I-2)+(B1.131), (I-2)+(B1.132), (I-2)+(B1.133), (I-2)+(B1.134), (I-2)+(B1.135), (I-2)+(B1.136), (I-2)+(B1.137), (I-2)+(B1.138), (I-2)+(B1.139), (I-2)+(B1.140), (I-2)+(B1.141), (I-2)+(B1.142), (I-2)+(B1.143), (I-2)+(B1.144), (I-2)+(B1.145), (I-2)+(B1.146), (I-2)+(B1.147), (I-2)+(B1.148), (I-2)+(B1.149), (I-2)+(B1.150), (I-2)+(B1.151), (I-2)+(B1.152), (I-2)+(B1.153), (I-2)+(B1.154), (I-2)+(B1.155), (I-2)+(B1.156), (I-2)+(B1.157), (I-2)+(B1.158), (I-2)+(B1.159), (I-2)+(B1.160), (I-2)+(B1.161), (I-2)+(B1.162), (I-2)+(B1.163), (I-2)+(B1.164), (I-2)+(B1.165), (I-2)+(B1.166), (I-2)+(B1.167), (I-2)+(B1.168), (I-2)+(B1.169), (I-2)+(B1.170), (I-2)+(B1.171), (I-2)+(B1.172), (I-2)+(B1.173), (I-2)+(B1.174), (I-2)+(B1.175), (I-2)+(B1.176), (I-2)+(B1.177), (I-2)+(B1.178), (I-2)+(B1.179), (I-2)+(B1.180), (I-2)+(B1.181), (I-2)+(B1.182), (I-2)+(B1.183), (I-2)+(B1.184), (I-2)+(B1.185), (I-2)+(B1.186), (I-2)+(B1.187), (I-2)+(B1.188), (I-2)+(B1.189), (I-2)+(B1.190), (I-2)+(B1.191), (I-2)+(B1.192), (I-2)+(B1.193), (I-2)+(B1.194), (I-2)+(B1.195), (I-2)+(B1.196), (I-2)+(B1.197), (I-2)+(B1.198), (I-2)+(B1.199), (I-2)+(B1.1.1), (I-2)+(B1.1.6), (I-2)+(B1.1.7), (I-2)+(B1.1.9), (I-2)+(B1.1.10), (I-2)+(B1.1.11), (I-2)+(B1.1.13), (I-2)+(B1.1.14), (I-2)+(B1.1.16), (I-2)+(B1.1.17), (I-2)+(B1.1.18), (I-2)+(B1.1.19), (I-2)+(B1.1.21), (I-2)+(B1.1.23), (I-2)+(B1.1.30), (I-2)+(B1.1.31), (I-2)+(B1.1.33), (I-2)+(B1.1.34), (I-2)+(B1.1.35), (I-2)+(B1.1.36), (I-2)+(B1.1.40), (I-2)+(B1.1.42), (I-2)+(B1.1.46), (I-2)+(B1.1.47), (I-2)+(B1.1.51), (I-2)+(B1.1.52), (I-2)+(B1.1.64), (I-2)+(B1.1.65), (I-2)+(B1.1.67), (I-2)+(B1.1.69), (I-2)+(B1.1.70), (I-2)+(B1.1.71), (I-2)+(B1.1.74), (I-2)+(B1.1.75), (I-2)+(B1.1.76), (I-2)+(B1.1.77), (I-2)+(B1.1.81), (I-2)+(B1.1.82), (I-2)+(B1.1.83), (I-2)+(B1.1.84), (I-2)+(B1.1.85), (I-2)+(B1.1.86), (I-2)+(B1.1.87), (I-2)+(B1.1.89), (I-2)+(B1.1.90), (I-2)+(B1.1.93), (I-2)+(B1.1.103), (I-2)+(B1.1.124), (I-2)+(B1.1.125), (I-2)+(B1.1.129), (I-2)+(B1.1.130), (I-2)+(B1.1.149), (I-2)+(B1.1.162), (I-2)+(B1.1.163), (I-2)+(B1.1.164), (I-2)+(B1.1.165), (I-2)+(B1.1.167), (I-2)+(B1.1.168), (I-2)+(B1.1.169), (I-2)+(B1.1.170), (I-2)+(B1.1.171), (I-2)+(B1.1.172), (I-2)+(B1.1.173), (I-2)+(B1.1.174), (I-2)+(B1.1.178), (I-2)+(B1.1.179), (I-2)+(B1.1.180), (I-2)+(B1.1.181), (I-2)+(B1.1.189), (I-2)+(B1.1.193), (I-2)+(B1.1.196), (I-2)+(B2.1), (I-2)+(B2.2), (I-2)+(B2.3), (I-2)+(B2.4), (I-2)+(B2.5), (I-2)+(B2.6), (I-2)+(B2.7), (I-2)+(B2.8), (I-2)+(B2.9), (I-2)+(B2.10), (I-2)+(B2.11), (I-2)+(B2.12), (I-2)+(B2.13), (I-2)+(B2.14), (I-2)+(B2.15), (I-2)+(B2.16), (I-2)+(B2.17), (I-2)+(B2.18), (I-2)+(B2.19), (I-2)+(B2.20), (I-2)+(B2.21), (I-2)+(B2.22), (I-2)+(B2.23), (I-2)+(B2.24), (I-2)+(B2.25), (I-2)+(B2.26), (I-2)+(B2.27), (I-2)+(B2.28), (I-2)+(B2.29), (I-2)+(B2.30), (I-2)+(B2.31), (I-2)+(B2.32), (I-2)+(B2.33), (I-2)+(B2.34), (I-2)+(B2.35), (I-2)+(B2.36), (I-2)+(B2.37), (I-2)+(B2.38), (I-2)+(B2.39), (I-2)+(B2.40), (I-2)+(B2.41), (I-2)+(B2.42), (I-2)+(B2.43), (I-2)+(B2.44), (I-2)+(B2.45), (I-2)+(B2.46), (I-2)+(B2.47), (I-2)+(B2.48), (I-2)+(B2.49), (I-2)+(B2.50), (I-2)+(B2.51), (I-2)+(B2.52), (I-2)+(B2.53), (I-2)+(B2.54), (I-2)+(B2.55), (I-2)+(B2.56), (I-2)+(B2.57), (I-2)+(B2.58), (I-2)+(B2.59), (I-2)+(B2.60), (I-2)+(B2.61), (I-2)+(B2.62), (I-2)+(B2.63), (I-2)+(B2.64), (I-2)+(B2.65), (I-2)+(B2.66), (I-2)+(B2.67), (I-2)+(B2.68), (I-2)+(B2.69), (I-2)+(B2.71), (I-2)+(B2.72), (I-2)+(B2.73), (I-2)+(B2.74), (I-2)+(B2.75), (I-2)+(B2.76), (I-2)+(B2.77), (I-2)+(B2.78), (I-2)+(B2.79), (I-2)+(B2.80), (I-2)+(B2.81), (I-2)+(B2.82), (I-2)+(B2.83), (I-2)+(B2.84), (I-2)+(B2.85), (I-2)+(B2.86), (I-2)+(B2.87), (I-2)+(B2.88), (I-2)+(B2.89), (I-2)+(B2.90), (I-2)+(B2.91), (I-2)+(B2.92), (I-2)+(B2.93), (I-2)+(B2.94), (I-2)+(B2.95), (I-2)+(B2.96), (I-2)+(B2.97), (I-2)+(B2.98), (I-2)+(B2.99), (I-2)+(B2.100), (I-2)+(B2.101), (I-2)+(B2.102), (I-2)+

(B2.103), (I-2)+(B2.104), (I-2)+(B2.105), (I-2)+(B2.106), (I-2)+(B2.107), (I-2)+(B2.108), (I-2)+(B2.109), (I-2)+(B2.110), (I-2)+(B2.111), (I-2)+(B2.112), (I-2)+(B2.113), (I-2)+(B2.114), (I-2)+(B2.115), (I-2)+(B2.116), (I-2)+(B2.117), (I-2)+(B2.118), (I-2)+(B2.119), (I-2)+(B2.120), (I-2)+(B2.121), (I-2)+(B2.122), (I-2)+(B2.123), (I-2)+(B2.124), (I-2)+(B2.125), (I-2)+(B2.126), (I-2)+(B2.127), (I-2)+(B2.128), (I-2)+(B2.129), (I-2)+(B2.130), (I-2)+(B2.131), (I-2)+(B2.132), (I-2)+(B2.133), (I-2)+(B2.134), (I-2)+(B2.135), (I-2)+(B2.136), (I-2)+(B2.137), (I-2)+(B2.138), (I-2)+(B2.139), (I-2)+(B2.140), (I-2)+(B2.141), (I-2)+(B2.142), (I-2)+(B2.143), (I-2)+(B2.144), (I-2)+(B2.145), (I-2)+(B2.146), (I-2)+(B2.147), (I-2)+(B2.148), (I-2)+(B2.149), (I-2)+(B2.150), (I-2)+(B2.151), (I-2)+(B2.152), (I-2)+(B2.153), (I-2)+(B2.154), (I-2)+(B2.155), (I-2)+(B2.156), (I-2)+(B2.157), (I-2)+(B2.158), (I-2)+(B2.159), (I-2)+(B2.160), (I-2)+(B2.161), (I-2)+(B2.162), (I-2)+(B2.163), (I-2)+(B2.164), (I-2)+(B2.165), (I-2)+(B2.166), (I-2)+(B2.167), (I-2)+(B2.168), (I-2)+(B2.169), (I-2)+(B2.170), (I-2)+(B2.171), (I-2)+(B2.172), (I-2)+(B2.173), (I-2)+(B2.174), (I-2)+(B2.175), (I-2)+(B2.176), (I-2)+(B2.177), (I-2)+(B2.178), (I-2)+(B2.179), (I-2)+(B2.2.1), (I-2)+(B2.2.2), (I-2)+(B2.2.4), (I-2)+(B2.2.8), (I-2)+(B2.2.26), (I-2)+(B2.2.27), (I-2)+(B2.2.28), (I-2)+(B2.2.29), (I-2)+(B2.2.30), (I-2)+(B2.2.31), (I-2)+(B2.2.32), (I-2)+(B2.2.33), (I-2)+(B2.2.34), (I-2)+(B2.2.35), (I-2)+(B2.2.36), (I-2)+(B2.2.37), (I-2)+(B2.2.38), (I-2)+(B2.2.39), (I-2)+(B2.2.55), (I-2)+(B2.2.58), (I-2)+(B2.2.86), (I-2)+(B2.2.88), (I-2)+(B2.2.94), (I-2)+(B2.2.96), (I-2)+(B2.2.97), (I-2)+(B2.2.98), (I-2)+(B2.2.121), (I-2)+(B2.2.140), (I-2)+(B2.2.141), (I-2)+(B2.2.172), (I-2)+(B2.2.173), (I-2)+(B2.2.174), (I-2)+(B2.2.175), (I-2)+(B2.2.176), (I-2)+(B2.2.177), (I-2)+(B3.1), (I-2)+(B3.2), (I-2)+(B3.3), (I-2)+(B4.1), (I-2)+(B4.2), (I-2)+(B4.3), (I-2)+(B4.4), (I-2)+(B4.5), (I-2)+(B4.6), (I-2)+(B4.7), (I-2)+(B4.8), (I-2)+(B4.9), (I-2)+(B4.10), (I-2)+(B4.11), (I-2)+(B4.12), (I-2)+(B4.13), (I-2)+(B4.14), (I-2)+(B4.15), (I-2)+(B4.16), (I-2)+(B4.17), (I-2)+(B4.18), (I-2)+(B4.19), (I-2)+(B4.20), (I-2)+(B4.21), (I-2)+(B4.22), (I-2)+(B4.23), (I-2)+(B4.24), (I-2)+(B4.25), (I-2)+(B4.26), (I-2)+(B5.1), (I-2)+(B5.2), (I-2)+(B5.3), (I-2)+(B5.4), (I-2)+(B5.5), (I-2)+(B5.6), (I-2)+(B5.7), (I-2)+(B5.8), (I-2)+(B5.9), (I-2)+(B5.10), (I-2)+(B5.11), (I-2)+(B5.12), (I-2)+(B5.13), (I-2)+(B5.14), (I-2)+(B5.15), (I-2)+(B5.16), (I-2)+(B5.17), (I-2)+(B5.18), (I-2)+(B5.19), (I-2)+(B5.20), (I-2)+(B5.21), (I-2)+(B5.22), (I-2)+(B5.23), (I-2)+(B5.24), (I-2)+(B5.25), (I-2)+(B5.26), (I-2)+(B5.27), (I-2)+(B5.28), (I-2)+(B5.29), (I-2)+(B5.30), (I-2)+(B5.31), (I-2)+(B5.32), (I-2)+(B5.33), (I-2)+(B5.34), (I-2)+(B5.35), (I-2)+(B5.36), (I-2)+(B5.37), (I-2)+(B5.38), (I-2)+(B5.39), (I-2)+(B5.40), (I-2)+(B5.41), (I-2)+(B5.42), (I-2)+(B5.43), (I-2)+(B5.44), (I-2)+(B6.1), (I-2)+(B6.2), (I-2)+(B6.6.2)

(I-3)+(B1.1), (I-3)+(B1.2), (I-3)+(B1.3), (I-3)+(B1.4), (I-3)+(B1.5), (I-3)+(B1.6), (I-3)+(B1.7), (I-3)+(B1.8), (I-3)+(B1.9), (I-3)+(B1.10), (I-3)+(B1.11), (I-3)+(B1.12), (I-3)+(B1.13), (I-3)+(B1.14), (I-3)+(B1.15), (I-3)+(B1.16), (I-3)+(B1.17), (I-3)+(B1.18), (I-3)+(B1.19), (I-3)+(B1.20), (I-3)+(B1.21), (I-3)+(B1.22), (I-3)+(B1.23), (I-3)+(B1.24), (I-3)+(B1.25), (I-3)+(B1.26), (I-3)+(B1.27), (I-3)+(B1.28), (I-3)+(B1.29), (I-3)+(B1.30), (I-3)+(B1.31), (I-3)+(B1.32), (I-3)+(B1.33), (I-3)+(B1.34), (I-3)+(B1.35), (I-3)+(B1.36), (I-3)+(B1.37), (I-3)+(B1.38), (I-3)+(B1.39), (I-3)+(B1.40), (I-3)+(B1.41), (I-3)+(B1.42), (I-3)+(B1.43), (I-3)+(B1.44), (I-3)+(B1.45), (I-3)+(B1.46), (I-3)+(B1.47), (I-3)+(B1.48), (I-3)+(B1.49), (I-3)+(B1.50), (I-3)+(B1.51), (I-3)+(B1.52), (I-3)+(B1.53), (I-3)+(B1.54), (I-3)+(B1.55), (I-3)+(B1.56), (I-3)+(B1.57), (I-3)+(B1.58), (I-3)+(B1.59), (I-3)+(B1.60), (I-3)+(B1.61), (I-3)+(B1.62), (I-3)+(B1.63), (I-3)+(B1.64), (I-3)+(B1.65), (I-3)+(B1.66), (I-3)+(B1.67), (I-3)+(B1.68), (I-3)+(B1.69), (I-3)+(B1.70), (I-3)+(B1.71), (I-3)+(B1.72), (I-3)+(B1.73), (I-3)+(B1.74), (I-3)+(B1.75), (I-3)+(B1.76), (I-3)+(B1.77), (I-3)+(B1.78), (I-3)+(B1.79), (I-3)+(B1.80), (I-3)+(B1.81), (I-3)+(B1.82), (I-3)+(B1.83), (I-3)+(B1.84), (I-3)+(B1.85), (I-3)+(B1.86), (I-3)+(B1.87), (I-3)+(B1.88), (I-3)+(B1.89), (I-3)+(B1.90), (I-3)+(B1.91), (I-3)+(B1.92), (I-3)+(B1.93), (I-3)+(B1.94), (I-3)+(B1.95), (I-3)+(B1.96), (I-3)+(B1.97), (I-3)+(B1.98), (I-3)+(B1.99), (I-3)+(B1.100), (I-3)+(B1.101), (I-3)+(B1.102), (I-3)+(B1.103), (I-3)+(B1.104), (I-3)+(B1.105), (I-3)+(B1.106), (I-3)+(B1.107), (I-3)+(B1.108), (I-3)+(B1.109), (I-3)+(B1.110), (I-3)+(B1.111), (I-3)+(B1.112), (I-3)+(B1.113), (I-3)+(B1.114), (I-3)+(B1.115), (I-3)+(B1.116), (I-3)+(B1.117), (I-3)+(B1.118), (I-3)+(B1.119), (I-3)+(B1.120), (I-3)+(B1.121), (I-3)+(B1.122), (I-3)+(B1.123), (I-3)+(B1.124), (I-3)+(B1.125), (I-3)+(B1.126), (I-3)+(B1.127), (I-3)+(B1.128), (I-3)+(B1.129), (I-3)+(B1.130), (I-3)+(B1.131), (I-3)+(B1.132), (I-3)+(B1.133), (I-3)+(B1.134), (I-3)+(B1.135), (I-3)+(B1.136), (I-3)+(B1.137), (I-3)+(B1.138), (I-3)+(B1.139), (I-3)+(B1.140), (I-3)+(B1.141), (I-3)+(B1.142), (I-3)+(B1.143), (I-3)+(B1.144), (I-3)+(B1.145), (I-3)+(B1.146), (I-3)+(B1.147), (I-3)+(B1.148), (I-3)+(B1.149), (I-3)+(B1.150), (I-3)+(B1.151), (I-3)+(B1.152), (I-3)+(B1.153), (I-3)+(B1.154), (I-3)+(B1.155), (I-3)+(B1.156), (I-3)+(B1.157), (I-3)+(B1.158), (I-3)+(B1.159), (I-3)+(B1.160), (I-3)+(B1.161), (I-3)+(B1.162), (I-3)+(B1.163), (I-3)+(B1.164), (I-3)+(B1.165), (I-3)+(B1.166), (I-3)+(B1.167), (I-3)+(B1.168), (I-3)+(B1.169), (I-3)+(B1.170), (I-3)+(B1.171), (I-3)+(B1.172), (I-3)+(B1.173), (I-3)+(B1.174), (I-3)+(B1.175), (I-3)+(B1.176), (I-3)+(B1.177), (I-3)+(B1.178), (I-3)+(B1.179), (I-3)+(B1.180), (I-3)+(B1.181), (I-3)+(B1.182), (I-3)+(B1.183), (I-3)+(B1.184), (I-3)+(B1.185), (I-3)+(B1.186), (I-3)+(B1.187), (I-3)+(B1.188), (I-3)+(B1.189), (I-3)+(B1.190), (I-3)+(B1.191), (I-3)+(B1.192), (I-3)+(B1.193), (I-3)+(B1.194), (I-3)+(B1.195), (I-3)+(B1.196), (I-3)+(B1.197), (I-3)+(B1.198), (I-3)+(B1.199), (I-3)+(B1.1.1), (I-3)+(B1.1.6), (I-3)+(B1.1.7), (I-3)+(B1.1.9), (I-3)+(B1.1.10), (I-3)+(B1.1.11), (I-3)+(B1.1.13), (I-3)+(B1.1.14), (I-3)+(B1.1.16), (I-3)+(B1.1.17), (I-3)+(B1.1.18), (I-3)+(B1.1.19), (I-3)+(B1.1.21), (I-3)+(B1.1.23), (I-3)+(B1.1.30), (I-3)+(B1.1.31), (I-3)+(B1.1.33), (I-3)+(B1.1.34), (I-3)+(B1.1.35), (I-3)+(B1.1.36), (I-3)+(B1.1.40), (I-3)+(B1.1.42), (I-3)+(B1.1.46), (I-3)+(B1.1.47), (I-3)+(B1.1.51), (I-3)+(B1.1.52), (I-3)+(B1.1.64), (I-3)+(B1.1.65), (I-3)+(B1.1.67), (I-3)+(B1.1.69), (I-3)+(B1.1.70), (I-3)+(B1.1.71), (I-3)+(B1.1.74), (I-3)+(B1.1.75), (I-3)+(B1.1.76), (I-3)+(B1.1.77), (I-3)+(B1.1.81), (I-3)+(B1.1.82), (I-3)+(B1.1.83), (I-3)+(B1.1.84), (I-3)+(B1.1.85), (I-3)+(B1.1.86), (I-3)+(B1.1.87), (I-3)+(B1.1.89), (I-3)+(B1.1.90), (I-3)+(B1.1.93), (I-3)+(B1.1.103), (I-3)+(B1.1.124), (I-3)+(B1.1.125), (I-3)+(B1.1.129), (I-3)+(B1.1.130), (I-3)+(B1.1.149), (I-3)+(B1.1.162), (I-3)+(B1.1.163), (I-3)+(B1.1.164), (I-3)+(B1.1.165), (I-3)+(B1.1.167), (I-3)+(B1.1.168), (I-3)+(B1.1.169), (I-3)+(B1.1.170), (I-3)+(B1.1.171), (I-3)+(B1.1.172), (I-3)+(B1.1.173), (I-3)+(B1.1.174), (I-3)+(B1.1.178), (I-3)+(B1.1.179), (I-3)+(B1.1.180), (I-3)+(B1.1.181), (I-3)+(B1.1.189), (I-3)+(B1.1.193), (I-3)+(B1.1.196), (I-3)+(B2.1), (I-3)+(B2.2), (I-3)+(B2.3), (I-3)+(B2.4), (I-3)+(B2.5), (I-3)+(B2.6), (I-3)+(B2.7), (I-3)+(B2.8), (I-3)+(B2.9), (I-3)+(B2.10), (I-3)+(B2.11), (I-3)+(B2.12), (I-3)+(B2.13), (I-3)+(B2.14), (I-3)+(B2.15), (I-3)+(B2.16), (I-3)+(B2.17), (I-3)+(B2.18), (I-3)+(B2.19), (I-3)+(B2.20), (I-3)+(B2.21), (I-3)+(B2.22), (I-3)+(B2.23), (I-3)+(B2.24), (I-3)+(B2.25), (I-3)+(B2.26), (I-3)+(B2.27), (I-3)+(B2.28), (I-3)+(B2.29), (I-3)+(B2.30), (I-3)+(B2.31), (I-3)+(B2.32), (I-3)+(B2.33), (I-3)+(B2.34), (I-3)+(B2.35), (I-3)+(B2.36), (I-3)+(B2.37), (I-3)+(B2.38), (I-3)+(B2.39), (I-3)+(B2.40), (I-3)+(B2.41), (I-3)+(B2.42), (I-3)+(B2.43), (I-3)+(B2.44), (I-3)+(B2.45), (I-3)+(B2.46), (I-3)+(B2.47), (I-3)+(B2.48), (I-3)+(B2.49), (I-3)+(B2.50), (I-3)+(B2.51), (I-3)+(B2.52), (I-3)+(B2.53), (I-3)+(B2.54), (I-3)+(B2.55), (I-3)+(B2.56), (I-3)+(B2.57), (I-3)+(B2.58), (I-3)+(B2.59), (I-3)+(B2.60), (I-3)+(B2.61), (I-3)+(B2.62), (I-3)+(B2.63), (I-3)+(B2.64), (I-3)+(B2.65), (I-3)+(B2.66), (I-3)+(B2.67), (I-3)+(B2.68), (I-3)+(B2.69), (I-3)+(B2.71), (I-3)+(B2.72), (I-3)+(B2.73), (I-3)+(B2.74), (I-3)+(B2.75), (I-3)+(B2.76), (I-3)+(B2.77), (I-3)+(B2.78), (I-3)+(B2.79), (I-3)+(B2.80), (I-3)+(B2.81), (I-3)+(B2.82), (I-3)+(B2.83), (I-3)+(B2.84), (I-3)+(B2.85), (I-3)+(B2.86), (I-3)+(B2.87), (I-3)+(B2.88), (I-3)+(B2.89), (I-3)+(B2.90), (I-3)+(B2.91), (I-3)+(B2.92), (I-3)+(B2.93), (I-3)+(B2.94), (I-3)+(B2.95), (I-3)+(B2.96), (I-3)+(B2.97), (I-3)+(B2.98), (I-3)+(B2.99), (I-3)+(B2.100), (I-3)+(B2.101), (I-3)+(B2.102), (I-3)+(B2.103), (I-3)+(B2.104), (I-3)+(B2.105), (I-3)+(B2.106), (I-3)+(B2.107), (I-3)+(B2.108), (I-3)+(B2.109), (I-3)+(B2.110), (I-3)+(B2.111), (I-3)+(B2.112), (I-3)+(B2.113), (I-3)+(B2.114), (I-3)+(B2.115), (I-3)+(B2.116), (I-3)+(B2.117), (I-3)+(B2.118), (I-3)+(B2.119), (I-3)+(B2.120), (I-3)+(B2.121), (I-3)+(B2.122), (I-3)+(B2.123), (I-3)+(B2.124), (I-3)+(B2.125), (I-3)+(B2.126), (I-3)+(B2.127), (I-3)+(B2.128), (I-3)+(B2.129), (I-3)+(B2.130), (I-3)+(B2.131), (I-3)+(B2.132), (I-3)+(B2.133), (I-3)+(B2.134), (I-3)+(B2.135), (I-3)+(B2.136), (I-3)+(B2.137), (I-3)+(B2.138), (I-3)+(B2.139), (I-3)+(B2.140), (I-3)+(B2.141), (I-3)+(B2.142), (I-3)+(B2.143), (I-3)+(B2.144), (I-3)+(B2.145), (I-3)+(B2.146), (I-3)+(B2.147), (I-3)+(B2.148), (I-3)+(B2.149), (I-3)+(B2.150), (I-3)+(B2.151), (I-3)+(B2.152), (I-3)+(B2.153), (I-3)+(B2.154), (I-3)+(B2.155), (I-3)+(B2.156), (I-3)+(B2.157), (I-3)+(B2.158), (I-3)+(B2.159), (I-3)+(B2.160), (I-3)+(B2.161), (I-3)+(B2.162), (I-3)+(B2.163), (I-3)+(B2.164), (I-3)+(B2.165), (I-3)+(B2.166), (I-3)+(B2.167), (I-3)+(B2.168), (I-3)+(B2.169), (I-3)+(B2.170), (I-3)+(B2.171), (I-3)+(B2.172), (I-3)+(B2.173), (I-3)+(B2.174), (I-3)+(B2.175), (I-3)+(B2.176), (I-3)+(B2.177), (I-3)+(B2.178), (I-3)+(B2.179), (I-3)+(B2.2.1), (I-3)+(B2.2.2), (I-3)+(B2.2.4), (I-3)+(B2.2.8), (I-3)+(B2.2.26), (I-3)+(B2.2.27), (I-3)+(B2.2.28), (I-3)+(B2.2.29), (I-3)+(B2.2.30), (I-3)+(B2.2.31), (I-3)+(B2.2.32), (I-3)+(B2.2.33), (I-3)+(B2.2.34), (I-3)+(B2.2.35), (I-3)+(B2.2.36), (I-3)+(B2.2.37), (I-3)+(B2.2.38), (I-3)+(B2.2.39), (I-3)+(B2.2.55), (I-3)+(B2.2.58), (I-3)+(B2.2.86), (I-3)+(B2.2.88), (I-3)+(B2.2.94), (I-3)+(B2.2.96), (I-3)+(B2.2.97), (I-3)+(B2.2.98), (I-3)+(B2.2.121), (I-3)+(B2.2.140), (I-3)+(B2.2.141), (I-3)+(B2.2.172), (I-3)+(B2.2.173), (I-3)+(B2.2.174), (I-3)+(B2.2.175), (I-3)+(B2.2.176), (I-3)+(B2.2.177), (I-3)+(B3.1), (I-3)+(B3.2), (I-3)+(B3.3), (I-3)+(B4.1), (I-3)+(B4.2), (I-3)+(B4.3), (I-3)+(B4.4), (I-3)+(B4.5), (I-3)+(B4.6), (I-3)+(B4.7), (I-3)+(B4.8), (I-3)+(B4.9), (I-3)+(B4.10), (I-3)+(B4.11), (I-3)+(B4.12), (I-3)+(B4.13), (I-3)+(B4.14), (I-3)+(B4.15), (I-3)+(B4.16), (I-3)+(B4.17), (I-3)+(B4.18), (I-3)+(B4.19), (I-3)+(B4.20), (I-3)+(B4.21), (I-3)+(B4.22), (I-3)+(B4.23), (I-3)+(B4.24), (I-3)+(B4.25), (I-3)+(B4.26), (I-3)+(B5.1), (I-3)+(B5.2), (I-3)+(B5.3), (I-3)+(B5.4), (I-3)+(B5.5), (I-3)+(B5.6), (I-3)+(B5.7), (I-3)+(B5.8), (I-3)+(B5.9), (I-3)+(B5.10), (I-3)+(B5.11), (I-3)+(B5.12), (I-3)+(B5.13), (I-3)+(B5.14), (I-3)+(B5.15), (I-3)+(B5.16), (I-3)+(B5.17), (I-3)+(B5.18), (I-3)+(B5.19), (I-3)+(B5.20), (I-3)+(B5.21), (I-3)+(B5.22), (I-3)+(B5.23), (I-3)+(B5.24), (I-3)+(B5.25), (I-3)+(B5.26), (I-3)+(B5.27), (I-3)+(B5.28), (I-3)+(B5.29), (I-3)+(B5.30), (I-3)+(B5.31), (I-3)+(B5.32), (I-3)+(B5.33), (I-3)+(B5.34), (I-3)+(B5.35), (I-3)+(B5.36), (I-3)+(B5.37), (I-3)+(B5.38), (I-3)+(B5.39), (I-3)+(B5.40), (I-3)+(B5.41), (I-3)+(B5.42), (I-3)+(B5.43), (I-3)+(B5.44), (I-3)+(B6.1), (I-3)+(B6.2), (I-3)+(B6.6.2).

The following combinations are particularly preferred: (I-1)+(B1.1), (I-1)+(B1.6), (I-1)+(B1.18), (I-2)+(B1.1), (I-2)+(B1.6), (I-2)+(B1.18), (I-3)+(B1.1), (I-3)+(B1.6), (I-3)+(B1.18), (I-1)+(B1.1.1), (I-1)+(B1.1.6), (I-1)+(B1.1.18), (I-2)+(B1.1.1), (I-2)+(B1.1.6), (I-2)+(B1.1.18), (I-3)+(B1.1.1), (I-3)+(B1.1.6), (I-3)+(B1.1.18).

The following combinations are most preferred: (I-1)+(B1.1), (I-1)+(B1.6), (I-1)+(B1.18), (I-2)+(B1.1), (I-2)+(B1.6), (I-2)+(B1.18), (I-3)+(B1.1), (I-3)+(B1.6), (I-3)+(B1.18).

The following combinations are furthermore preferred: (I-1)+(B1.1.1), (I-1)+(B1.1.6), (I-1)+(B1.1.18), (I-2)+(B1.1.1), (I-2)+(B1.1.6), (I-2)+(B1.1.18), (I-3)+(B1.1.1), (I-3)+(B1.1.6), (I-3)+(B1.1.18)

In the context of the present invention the term "composition" shall mean a physical mixture comprising compounds of the formula (I) and at least one biological control agent.

As used herein, the term "comprising" is to be interpreted as specifying the presence of the stated features, integers, steps, components or compounds as referred to, but does not preclude the presence or addition of one or more features, integers, steps, components or compounds, or groups thereof. Thus, e.g. a composition and/or formulation comprising a compound of the formula (I) and at least on biological control agent may comprise more compounds or more biological control agents than the actually cited ones, i.e. the composition and/or formulation may further comprise at least one compound (C) selected from the group consisting of fungicides. However, in context with the present disclosure, the term "comprising" also encloses "consisting of" and "including".

As used herein the term "at least one" shall refer to either one compound or biological control agent or the like, but also encompasses the presence of (at least) two, (at least) three or (at least) four compounds or biological control agents or the like.

The compositions may be used alone or in combination with other active ingredients such as fungicides. The active ingredients specified herein by their "common name" are known and described, for example, in the Pesticide Manual or can be searched in the internet (e.g. http://www.alanwood.net/pesticides). Where a compound can be present in tautomeric form, such a compound is understood herein before mentioned and herein below also to include, where applicable, corresponding tautomeric forms, even when these are not specifically mentioned in each case.

Examples of such fungicides to be used in combination with the composition and/or formulation according to the invention are (the numbering is used throughout the complete following description of the invention):

1) Inhibitors of the ergosterol biosynthesis, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazol, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafine, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-5-(difluoromethyl)-2-methyl-4-[3-(trimethylsilyl)propoxylphenyl]-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]1H-imidazole-1-carbothioate, (1.65) Pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-yl thiocyanate, (1.68) 5-(allylsulfanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-yl thiocyanate, (1.73) 1-{[rel(2R,3R)-3-(2-chlorophenyl)-2-(2,4-difluorophenyl)oxiran-2-yl]methyl}-1H-1,2,4-triazol-5-yl thiocyanate, (1.74) 5-(allylsulfanyl)-1-{[rel(2R,3S)-3-(2-chlorophenyl)-2-(2,4-difluorophenyl)oxiran-2-yl]methyl}-1H-1,2,4-triazole, (1.75) 5-(allylsulfanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4-triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of the respiratory chain at complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (synepimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) Isofetamid, (2.44) 1-methyl-3-

(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain at complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[(R{[(1E)-1-(3-{[(E)-1-fluoro-2-phenylvinyl]oxy}phenyl)ethylidene]amino}oxy)methyl]phenyl}-2-(methoxyimino)-N-methylacetamide, (3.27) Fenaminostrobin, (3.28) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino]methyl}sulfanyl)methyl]phenyl}-3-methoxyacrylate, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Inhibitors of the mitosis and cell division, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable to have a multisite action, for example (5.01) bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper (2+) sulfate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulfur and sulfur preparations including calcium polysulfide, (5.31) thiram, (5.32) tolylfluanid, (5.33) zineb, (5.34) ziram, (5.35) anilazine.

6) Compounds capable to induce a host defence, for example (6.01) acibenzolar-S-methyl, (6.02) isotianil, (6.03) probenazole, (6.04) tiadinil, (6.05) laminarin.

7) Inhibitors of the amino acid and/or protein biosynthesis, for example (7.01) andoprim, (7.02) blasticidinS, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) Inhibitors of the ATP production, for example (8.01) fentin acetate, (8.02) fentin chloride, (8.03) fentin hydroxide, (8.04) silthiofam.

9) Inhibitors of the cell wall synthesis, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Inhibitors of the lipid and membrane synthesis, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of the melanin biosynthesis, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Inhibitors of the nucleic acid synthesis, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazol, (12.09) metalaxyl, (12.10) metalaxyl-M (mefenoxam), (12.11) ofurace, (12.12) oxadixyl, (12.13) oxolinic acid, (12.14) octhilinone.

13) Inhibitors of the signal transduction, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable to act as an uncoupler, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) chinomethionat, (15.006) pyriofenone (chlazafenone), (15.007) cufraneb, (15.008) cyflufenamid, (15.009) cymoxanil, (15.010) cyprosulfamide, (15.011) dazomet, (15.012) debacarb, (15.013) dichlorophen, (15.014) diclomezine, (15.015) difenzoquat, (15.016) difenzoquat metilsulfate, (15.017) diphenylamine, (15.018) ecomate, (15.019) fenpyrazamine, (15.020) flumetover, (15.021) fluoroimide, (15.022) flusulfamide, (15.023) flutianil, (15.024) fosetyl-aluminium, (15.025) fosetylcalcium, (15.026) fosetyl-sodium, (15.027) hexachlorobenzene, (15.028) irumamycin, (15.029) methasulfocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and its salts, (15.041) propamocarb-fosetylate, (15.042) propanosine-sodium, (15.043) pyrimorph, (15.044) pyrrolnitrine, (15.045) tebufloquin, (15.046) tecloftalam, (15.047) tolnifanide, (15.048) triazoxide, (15.049) trichlamide, (15.050) zarilamid, (15.051) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-[(4-[(5S)-5-(2,6-difluorophenyl)-4,5-dihydro-1,2-oxazol-3-yl]-1,3-thiazol-2-yl]piperidin-1-yl)-2-[5-methyl-3-(trifluoromethyl)-1H-pyrazol-1-yl]ethanone, (15.054) Oxathiapiprolin, (15.055) 1-(4-methoxyphenoxy)-3,3-dimethylbutan-2-yl 1H-imidazole-1-carboxylate, (15.056) 2,3,5,6-tetrachloro-4-(methylsulfonyl)pyridine, (15.057) 2,3-dibutyl-6-chlorothieno[2,3-d]pyrimidin-4(3H)-one, (15.058) 2,6-dimethyl-1H,5H-[1,4]dithimino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062) 2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarbonitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-yn-1-yl)thiophene-2-sulfonohydrazide, (15.071) 5-fluoro-2-[(4-fluorobenzyl)oxy]pyrimidin-4-amine, (15.072) 5-fluoro-2-[(4-methylbenzyl)oxy]pyrimidin-4-amine, (15.073) 5-methyl-6-octyl[1,2,4]triazolo[1,5-a]pyrimidin-7-amine, (15.074) ethyl (2Z)-3-amino-2-cyano-3-phenylacrylate, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-yn-1-yloxy)phenyl]propanamide, (15.077) N-[(4-chlorophenyl)(cyano)methyl]-3-[3-methoxy-4-(prop-2-yn-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N-{(E)-[(cyclopropylmethoxy)imino][6-(difluoromethoxy)-2,3-difluorophenyl]methyl}-2-phenylacetamide, (15.082) N-{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.087) pentyl {6-[({[(1-methyl-1H-tetrazol-5-yl)(phenyl)methylene]amino}oxy)methyl]pyridin-2-yl}carbamate, (15.088) phenazine-1-carboxylic acid, (15.089) quinolin-8-ol, (15.090) quinolin-8-ol sulfate (2:1), (15.091) tert-butyl {6-[({[(1-methyl-1H-tetrazol-5-yl)(phenyl)methylene]amino}oxy)methyl]pyridin-2-yl}carbamate, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulfonyl)valinamide, (15.094) 4-oxo-4-[(2-phenylethyl)amino]butanoic acid, (15.095) but-3-yn-1-yl {6-[(R{[(Z)-(1-methyl-1H-tetrazol-5-yl)(phenyl)methylene]amino}oxy)methyl]pyridin-2-yl}carbamate, (15.096) 4-amino-5-fluoropyrimidin-2-ol (tautomeric form: 4-amino-5-fluoropyrimidin-2(1H)-one), (15.097) propyl 3,4,5-trihydroxybenzoate, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) Abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-methylimidoformamide, (15.108) N'-{5- bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazol-5-amine, (15.135) 9-fluoro-2,2-dimethyl-5-(quinolin-3-yl)-2,3-dihydro-1,4-benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazol-5-amine, (15.139) 4-(2-chloro-4-fluorophenyl)-N-(2,6-difluorophenyl)-1,3-dimethyl-1H-pyrazol-5-amine, (15.140) 4-(2-chloro-4-fluorophenyl)-N-(2-chloro-6-fluorophenyl)-1,3-dimethyl-1H-pyrazol-5-amine, (15.141) 4-(2-bromo-4-fluorophenyl)-N-(2-chloro-6-fluorophenyl)-1,3-dimethyl-1H-pyrazol-5-amine, (15.142) N-(2-bromo-6-fluorophenyl)-4-(2-chloro-4-fluorophenyl)-1,3-dimethyl-1H-pyrazol-5-amine, (15.143) 4-(2-bromo-4-fluorophenyl)-N-(2-bromophenyl)-1,3-dimethyl-1H-pyrazol-5-amine, (15.144) 4-(2-bromo-4-fluorophenyl)-N-(2-bromo-6-fluorophenyl)-1,3-dimethyl-1H-pyrazol-5-amine, (15.145) 4-(2-bromo-4-fluorophenyl)-N-(2-chlorophenyl)-1,3-dimethyl-1H-pyrazol-5-amine, (15.146) N-(2-bromophenyl)-4-(2-chloro-4-fluorophenyl)-1,3-dimethyl-1H-pyrazol-5-amine, (15.147) 4-(2-chloro-4-fluorophenyl)-N-(2-chlorophenyl)-1,3-dimethyl-1H-pyrazol-5-amine, (15.148) 4-(2-bromo-4-fluorophenyl)-N-(2,6-difluorophenyl)-1,3-dimethyl-1H-pyrazol-5-amine, (15.149) 4-(2-bromo-4-fluorophenyl)-N-(2-fluorophenyl)-1,3-dimethyl-1H-pyrazol-5-amine, (15.150) N'-(4-{3-[(difluoromethyl)sulfanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulfanyl]phenoxy}phenyl)-N-ethyl-N-methylimidoformamide, (15.152) N'-(2,5-dimethyl-4-{3-[(2,2,2-trifluoroethyl)sulfanyl]phenoxy}phenyl)-N-ethyl-N-methylimidoformamide, (15.153) N'-(2,5-dimethyl-4-{3-[(2,2,3,3-tetrafluoropropyl)sulfanyl]phenoxy}phenyl)-N-ethyl-N-methylimidoformamide, (15.154) N'-(2,5-dimethyl-4-{3-[(pentafluoroethyl)sulfanyl]phenoxy}phenyl)-N-ethyl-N-methylimidoformamide, (15.155) N'-(4-{[3-(difluoromethoxy)phenyl]sulfanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulfanyl}phenyl)-N-ethyl-N-methylimidoformamide, (15.157) N'-(2,5-dimethyl-4-{[3-(2,2,2-trifluoroethoxy)phenyl]sulfanyl}phenyl)-N-ethyl-N-methylimidoformamide, (15.158) N'-(2,5-dimethyl-4-{[3-(2,2,3,3-tetrafluoropropoxy)phenyl]sulfanyl}phenyl)-N-ethyl-N-methylimidoformamide, (15.159) N'-(2,5-dimethyl-4-{[3-(pentafluoroethoxy)phenyl]sulfanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl}-4,5-dihydro-1,2-oxazol-3-yl]-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]

ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate.

Formulations

Although the composition according to the present invention comprises compounds of the formula (I) and at least a biological control agent, the final used composition is usually formulated to be suitable for agrochemical application e.g. by mixing the compounds of the formula (I) with the biological control agent and an agriculturally suitable additive such as suitable extenders, solvents, spontaneity promoters, carriers, emulsifiers, dispersants, frost protectants, biocides, thickeners, adjuvants or the like. Those compositions are referred to as formulations or commercial formulations. Those compositions are also referred to as agricultural compositions.

Accordingly, in one aspect of the present invention such formulations, and application forms prepared from them, are provided as crop protection agents and/or pesticidal agents, such as drench, drip and spray liquors, comprising the composition of the invention. The application forms may comprise activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared either in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.00000001% and 98% by weight of active compound or, with particular preference, between 0.01% and 95% by weight of active compound, more preferably between 0.5% and 90% by weight of active compound, based on the weight of the formulation. The content of the active compound is defined as the sum of the compound of formula (I) and the at least one biological control agent.

The active compound content of the application forms (crop protection products) prepared from the formulations may vary within wide ranges. The active compound concentration of the application forms may be situated typically between 0.00000001% and 95% by weight of active compound, preferably between 0.00001% and 1% by weight, based on the weight of the application form. Application takes place in a customary manner adapted to the application forms.

The compositions according to the invention may be present as such or in their formulations and in the use forms prepared from these formulations as a mixture with other (known) active ingredients, such as attractants, sterilants, bactericides, acaricides, nematicides, fungicides, insecticides, growth regulators, herbicides, fertilizers, safeners and/or semiochemicals. The formulation comprising a compound of the formula (I) and a biological control agent and the agriculturally suitable additives as described above, can be used as a pesticide. In a specific embodiment of the invention the formulation as defined above can be used as a fungicide. In another specific embodiment of the invention the formulation as defined above acts in a synergistic fashion.

According to the present invention, in the composition and/or formulation according to the invention, the compound ratio (I)/B may be advantageously chosen so as to produce a synergistic effect. The term "synergistic effect" as well as the term "acting in a synergistic fashion" is understood to have the meaning as defined by Colby in an article entitled "Calculation of the synergistic and antagonistic responses of herbicide combinations" Weeds, (1967), 15, pages 20-22 as described in detail further below.

The composition and/or formulation according to the present invention can be combined in any specific ratio between the two mandatory components. In the compositions and/or formulations according to the invention the compounds of the general formula (I) and the biological control agent (B) as defined above are present in a synergistically effective weight ratio of (I):(B) in a range of 1000:1 to 1:10 000, preferably in a weight ratio of 1000:1 to 1:1000, more preferably in a weight ratio of 500:1 to 1:500, most preferably in a weight ratio of 100:1 to 1:100. Further ratios of (I):(B) which can be used according to the present invention with increasing preferences the order given are: 800:1 to 1:800, 700:1 to 1:700, 750:1 to 1:750, 600:1 to 1:600, 400:1 to 1:400, 300:1 to 1:300, 250:1 to 1:250, 200:1 to 1:200, 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 20:1 to 1:20, 15:1 to 1:15, 10:1 to 1:10, 5:1 to 1:5, 4:1 to 1:4, 3:1 to 1:3, 2:1 to 1:2.

In a preferred embodiment the biological control agent e.g. their spores are present in a solo-formulation or the combined formulation in a concentration of at least $10^5$ colony forming units per gram preparation (e.g. cells/g preparation or spores/g preparation), such as $10^5$-$10^{12}$ cfu/g, preferably $10^6$-$10^{11}$ cfu/g, more preferably $10^7$-$10^{10}$ cfu/g and most preferably $10^9$-$10^{10}$ cfu/g at the time point of applying biological control agents on a plant or plant parts such as seeds, fruits or vegetables. Also references to the concentration of biological control agents in form of, e.g., spores or cells—when discussing ratios between the amount of a preparation of at least one biological control agent and the amount of the compound of the formula (I)—are made in view of the time point when the biological control agent is applied on a plant or plant parts such as seeds, fruits or vegetables.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the compositions and/or formulations which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the compositions and/or formulations according to the invention may also have a strengthening effect in plants. Accordingly, they are also suitable for mobilizing the defense system of the plant against attack by phytopathogenic fungi. This may, if appropriate, be one of the reasons of the enhanced activity of the compositions and/or formulations according to the invention, for example against fungi, in particular phytopathogenic fungi. "Plant-strengthening" (resistance-inducing) substances are to be understood as meaning, in the present context, those substances or combinations of substances which are capable of stimulating the defense system of plants in such a way that, when subsequently inoculated with harmful microorganisms, the treated plants display a substantial degree of resistance to these microorganisms. In a specific embodiment of the invention, harmful microorganisms are phytopathogenic fungi. Thus, the compositions and/or formulations according to the invention can be employed for protecting plants against attack by the below-mentioned pathogens within a certain period of time after the treatment. The period of time within which protection is effected generally extends from 1 to 10 days, preferably 1 to 7 days, after the treatment of the plants with the inventive composition.

In a specific embodiment, the invention comprises a method for reducing damage of plants and plant parts or losses in harvested fruits or vegetables caused by phytopathogenic fungi by controlling such phytopathogenic fungi, comprising applying the composition and/or formulation to the plant or the phytopathogenic fungi or the habitat of the plant or the habitat of the phytopathogenic fungi. Accordingly, the present invention also relates to compositions and/or formulations for controlling phytopathogenic fungi, comprising an effective but non-phytotoxic amount of the compositions and/or formulations according to the invention. These are preferably fungicidal compositions which comprise agriculturally suitable additives as described above, i.e. formulations.

By "plants" is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. Plants also comprise plant parts.

By "plant parts" is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

In this context the term "damage of plants" or "damage of plant parts" comprises in comparison to uninfected or unharmed plants e.g. the decrease of plant growth or yield or the decrease of plant vigor, comprising plant health, plant quality and seed vigor, a decreased resistance to harmful microorganisms such as phytopathogenic fungi, a decreased abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) or the like, an increased stand failure, decreased recovery, impaired greening effect and decreased photosynthetic efficiency. Reducing the damage of plants and plant parts often results in healthier plants and/or in an increase in plant vigor and yield. The compositions and/or formulations according to the invention, in combination with good plant tolerance and favourable toxicity to warm-blooded animals and being tolerated well by the environment, are suitable for protecting plants and plant parts, for increasing harvest yields and for improving the quality of the harvested material.

An "effective but non-phytotoxic amount" means an amount of the composition and/or formulation according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions and/or formulations.

In the context of the present invention, "control of phytopathogenic fungi" means a reduction in infestation by phytopathogenic fungi as defined above, compared with the untreated plant measured as fungicidal efficacy, preferably a reduction by 25-50%, compared with the untreated plant (100%), more preferably a reduction by 40-79%, compared with the untreated plant (100%); even more preferably, the infection by phytopathogenic fungi is entirely suppressed (by 70-100%). The control may be curative, i.e. for treatment of already infected plants, or protective, for protection of plants which have not yet been infected. In a specific embodiment the compositions and/or formulations according to the invention can be used for curative or protective or preventive control of phytopathogenic fungi. The invention therefore also relates to curative and protective methods for controlling phytopathogenic fungi by the use of the inventive compositions and/or formulations. The compositions and/or formulations according to the invention are active against normally sensitive and resistant species of phytopathogenic fungi and against all or some stages of development. The term "preventive control of phytopathogenic fungi" comprises the use of compositions and/or formulations according to the invention for the prevention of diseases. Thus, a further aspect of the present invention is the use of compositions and/or formulations according to the invention for controlling diseases such as phytopathogenic fungi, e.g., in agriculture, in horticulture, in forests, in gardens and leisure facilities as well as in the protection of stored products and materials.

The term "applying the composition and/or formulation to the plant or the phytopathogenic fungi or the habitat of the plant or the habitat of the phytopathogenic fungi" refers to the treatment of a plant and/or phytopathogenic fungi and/or the habitat of the plant or the phytopathogenic fungi with the compositions and/or formulations according to the invention. The treatment is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching) and drip irrigating. It is also possible to deploy the compositions and/or formulations by the ultra-low volume method or to inject the composition and/or formulation preparation or the compositions and/or formulations itself into the soil.

When using the compositions according to the invention or the formulation comprising the composition according to the invention and the agriculturally suitable additives as described above as fungicides, the application rates can be varied within a relatively wide range, depending on the kind of application. The application rate of the compositions is

- in the case of treatment of a plant or plant parts, for example leaves: from 0.1 to 10 000 g/ha, preferably from 1 to 10 000 g/ha, more preferably from 10 to 5000 g/ha, more preferably from 10 to 1000 g/ha, (in the case of application by watering or dripping, it is even possible to reduce the application rate, especially when inert substrates such as rockwool or perlite are used);
- in the case of soil treatment: from 0.1 to 10 000 g/ha, preferably from 1 to 5000 g/ha.

These application rates are merely by way of example and are not limiting for the purposes of the invention.

The compositions and/or formulations according to the invention can thus be used to protect plants from attack by the pathogens mentioned below for a certain period of time after treatment. The period for which protection is provided extends generally for 1 to 28 days, preferably for 1 to 14 days, more preferably for 1 to 10 days, most preferably for 1 to 7 days, after the treatment of the plant or the plant parts with the inventive compositions and/or formulations.

The method of treatment according to the invention also provides the use or application of compounds according to formula (I) and one biological control agent as defined above in a simultaneous, separate or sequential manner. In a preferred embodiment the method of treatment according to the invention provides the use or application of compounds according to formula (I) and one biological control agent as defined above in a simultaneous manner.

The plants listed further down in the description can particularly advantageously be treated in accordance with the compositions and/or formulations according to the invention. The preferred ranges stated above for the compositions also apply to the treatment of these plants. Particular emphasis is given to the treatment of plants with the compositions and/or formulations specifically mentioned in the present text.

The inventive compositions and/or formulations, when they are well tolerated by plants, have favourable homeotherm toxicity and are well tolerated by the environment, are suitable for protecting plants and plant organs, for enhancing harvest yields, for improving the quality of the harvested material. They can preferably be used as crop protection compositions and/or formulations. They are active against normally sensitive and resistant species and against all or some stages of development.

The fact that the compositions and/or formulations are well tolerated by plants at the concentrations required for controlling phytopathogenic fungi allows the treatment of above-ground parts of plants, of propagation stock and seeds, and of the soil.

The "habitat of the plant" comprises the environment where the plant is growing, e.g. the soil or nutrition medium—which is in a radius of at least 30 cm, 20 cm, 10 cm around the caulis or bole of a plant to be treated or which is at least 30 cm, 20 cm, 10 cm around the root system of said plant to be treated, respectively. The term "habitat of the phytopathogenic fungi" as used herein is defined as the seed, the plant or plant parts or the fruit. It also comprises the soil or the nutrition medium in which the plant grows—which is in a radius of at least 30 cm, 20 cm, 10 cm around the caulis or bole of a plant to be treated or which is at least 30 cm, 20 cm, 10 cm around the root system of said plant to be treated, respectively.

Plants

Plants which can be treated in accordance with the invention include the following main crop plants including fruits and vegetables such as maize, soya bean, alfalfa, cotton, sunflower, *Brassica* oil seeds such as *Brassica napus* (e.g. canola, rapeseed), *Brassica rapa, B. juncea* (e.g. (field) mustard) and *Brassica carinata, Arecaceae* sp. (e.g. oilpalm, coconut), rice, wheat, sugar beet, sugar cane, oats, rye, barley, millet and sorghum, triticale, flax, nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, capsicum, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. *cannabis*), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Plants which can particularly be treated in accordance with the invention include the following main crop plants including fruits and vegetables such as: *Brassica* oil seeds such as *Brassica napus* (e.g. canola, rapeseed), *Brassica rapa, Brassica juncea* (e.g. (field) mustard) and *Brassica carinata, Arecaceae* sp. (e.g. oilpalm, coconut), nuts, grapes and vine and various fruit and vegetables from various botanic taxa, e.g. *Rosaceae* sp. (e.g. pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae*sp., *Oleaceae* sp. (e.g. olive tree), *Actinidaceae* sp., *Lauraceae* sp. (e.g. avocado, cinnamon, camphor), *Musaceae* sp. (e.g. banana trees and plantations), *Rubiaceae* sp. (e.g. coffee), *Theaceae* sp. (e.g. tea), *Sterculiceae* sp., *Rutaceae* sp. (e.g. lemons, oranges, mandarins and grapefruit); *Solanaceae* sp. (e.g. tomatoes, potatoes, peppers, *capsicum*, aubergines, tobacco), *Liliaceae* sp., *Compositae* sp. (e.g. lettuce, artichokes and chicory—including root chicory, endive or common chicory), *Umbelliferae* sp. (e.g. carrots, parsley, celery and celeriac), *Cucurbitaceae* sp. (e.g. cucumbers—including gherkins, pumpkins, watermelons, calabashes and melons), *Alliaceae* sp. (e.g. leeks and onions), *Cruciferae* sp. (e.g. white cabbage, red cabbage, broccoli, cauliflower, Brussels sprouts, pak choi, kohlrabi, radishes, horseradish, cress and chinese cabbage), *Leguminosae* sp. (e.g. peanuts, peas, lentils and beans—e.g. common beans and broad beans), *Chenopodiaceae* sp. (e.g. Swiss chard, fodder beet, spinach, beetroot), *Linaceae* sp. (e.g. hemp), *Cannabeacea* sp. (e.g. *cannabis*), *Malvaceae* sp. (e.g. okra, cocoa), *Papaveraceae* (e.g. poppy), *Asparagaceae* (e.g. asparagus); useful plants and ornamental plants in the garden and woods including turf, lawn, grass and *Stevia rebaudiana*; and in each case genetically modified types of these plants.

Preferably the treated plant is selected from canola, rapeseed, field mustard, oilpalm, coconut, nuts, grapes and vine, apples, pears, apricots, cherries, almonds, plums, peaches, strawberries, raspberries, red and black currant and gooseberry, *Ribesioidae* sp., *Juglandaceae* sp., *Betulaceae* sp., *Anacardiaceae* sp., *Fagaceae* sp., *Moraceae* sp., olive tree, avocado, cinnamon, camphor, banana trees and plantations, coffee, tea, *Sterculiceae* sp., lemons, oranges, mandarins, grapefruit, tomatoes, potatoes, peppers, *capsicum*, aubergines, tobacco, *Liliaceae* sp., lettuce, artichokes, chicory, including root chicory, endive or common chicory, carrots, parsley, celery, celeriac, cucumbers, gherkins, pumpkins, watermelons, calabashes, melons, leeks, onions, white cabbage, red cabbage, broccoli, cauliflower, Brussels sprouts, pak choi, kohlrabi, radishes, horseradish, cress, chinese cabbage, peanuts, peas, lentils, beans, including common beans and broad beans, Swiss chard, fodder beet, spinach, beetroot, hemp, *cannabis*, okra, cocoa, poppy, asparagus, useful plants and ornamental plants in the garden and woods including turf, lawn, grass and *Stevia rebaudiana*; and in each case genetically modified types of these plants Genetically Modified Organisms As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts" or "parts of plants" or "plant parts" have been explained above. More preferably, plants of the plant cultivars which are commercially available or are in use are treated in accordance with the invention. Plant cultivars are understood to mean plants which have new properties ("traits") and have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology, RNA interference—RNAi—technology or microRNA—miRNA—technology). A heterologous gene that is located in the genome is also called a transgene. A transgene that is defined by its particular location in the plant genome is called a transformation or transgenic event.

Plants and plant cultivars which are to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against diseases, such as against phytopathogenic fungi.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), comprising early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Phytopathogenic Fungi

The compositions and/or formulations according to the invention comprise a method for reducing damage of plants and plant parts or losses in harvested fruits or vegetables caused by phytopathogenic fungi by controlling such phytopathogenic fungi. Accordingly the compositions and/or formulations according to the invention have potent microbicidal activity and can be used for control of phytopathogenic fungi in crop protection and in the protection of materials.

Such phytopathogenic fungi include soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. *Fungi imperfecti*). Some fungicides are systemically active and ca be used in plant protection as foliar, seed dressing or soil fungicide. Furthermore, they are suitable for combating fungi, which inter alia infest wood or roots of plant.

Examples of phytopathogenic fungi which can be treated in accordance with the invention comprise:
diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*;
diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondita*, *P. triticina*, *P. graminis* or *P. striiformis*; *Uromyces* species, for example *Uromyces appendiculatus*; diseases caused by pathogens from the group of the Oomycetes, for example *Albugo* species, for example *Algubo candida*; *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*;
leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*), *Cochliobolus miyabeanus*; *Colletotrichum* species, for example *Colletotrichum lindemuthanium*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*, *Leptosphaeria nodorum*; *Magnaporthe* species, for example *Magnaporthe grisea*; *Microdochium* species, for example *Microdochium nivale*; *Mycosphaerella* species, for example *Mycosphaerella graminicola*, *M. arachidicola* and *M. fijiensis*; *Phaeosphaeria* species, for example *Phaeosphaeria nodorum*; *Pyrenophora* species, for example *Pyrenophora teres*, *Pyrenophora tritici repentis*; *Ramularia* species, for example *Ramularia collo-cygni*, *Ramularia areola*; *Rhynchosporium* species, for example *Rhynchosporium secalis*; *Septoria* species, for example *Septoria apii*, *Septoria lycopersii*; *Typhula* species, for example *Typhula incarnata*; *Venturia* species, for example *Venturia inaequalis*;
root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, such as, for example *Rhizoctonia solani*; *Sarocladium* diseases caused for example by *Sarocladium oryzae*; *Sclerotium* diseases caused for example by *Sclerotium oryzae*; *Tapesia* species, for example *Tapesia acuformis*; *Thielaviopsis* species, for example *Thielaviopsis basicola*;
ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example *Septoria nodorum*;
diseases caused by smut fungi, for example *Sphacelotheca* species, for example *Sphacelotheca reiliana*; *Tilletia* species, for example *Tilletia caries*, *T. controversa*; *Urocystis* species, for example *Urocystis occulta*; *Ustilago* species, for example *Ustilago nuda*, *U. nuda tritici*;

fruit rot caused, for example, by *Aspergillus* species, for example *Aspergillus flavus*; *Botrytis* species, for example *Botrytis cinerea*; for example *Monilinia* species, for example *Monilinia laxa*; *Penicillium* species, for example *Penicillium expansum* and *P. purpurogenum*; *Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (Conidiaform: *Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma lingam*; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani*; *Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;

wilt diseases caused, for example, by *Verticilium* species, for example *Verticilium longisporum*;

leaf blister or leaf curl diseases caused, for example, by *Exobasidium* species, for example *Exobasidium vexans*; *Taphrina* species, for example *Taphrina deformans*;

decline diseases of wooden plants caused, for example, by Esca disease, caused for example by *Phaemoniella clamydospora, Phaeoacremonium aleophilum* and *Fomitiporia mediterranea*; Eutypa dyeback, caused for example by *Eutypa lata*; *Ganoderma* diseases caused for example by *Ganoderma boninense*; *Rigidoporus* diseases caused for example by *Rigidoporus lignosus*;

diseases of flowers and seeds caused, for example, by *Botrytis* species, for example *Botrytis cinerea*;

diseases of plant tubers caused, for example, by *Rhizoctonia* species, for example *Rhizoctonia solani*; *Helminthosporium* species, for example *Helminthosporium solani*;

Club root caused, for example, by *Plasmodiophora* species, for example *Plamodiophora brassicae*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

In particular, the compositions and/or formulations according to the invention are suitable for controlling the following plant diseases: *Albugo* spp. (white rust) on ornamental plants, vegetable crops (e.g. *A. candida*) and sunflowers (e.g. *A. tragopogonis*); *Alternaria* spp. (black spot disease, black blotch) on vegetables, oilseed rape (e.g. *A. brassicola* or *A. brassicae*), sugar beet (e.g. *A. tenuis*), fruit, rice, soybeans and also on potatoes (e.g. *A. solani* or *A. alternata*) and tomatoes (e.g. *A. solani* or *A. alternata*) and *Alternaria* spp. (black head) on wheat; *Aphanomyces* spp. on sugar beet and vegetables; *Ascochyta* spp. on cereals and vegetables, e.g. *A. tritici* (*Ascochyta* leaf blight) on wheat and *A. hordei* on barley; *Bipolaris* and *Drechslera* spp. (teleomorph: *Cochliobolus* spp.), e.g. leaf spot diseases (*D. maydis* and *B. zeicola*) on corn, e.g. glume blotch (*B. sorokiniana*) on cereals and e.g. *B. oryzae* on rice and on lawn; *Blumeria* (old name: *Erysiphe*) *graminis* (powdery mildew) on cereals (e.g. wheat or barley); *Botryosphaeria* spp. ('Slack Dead Arm Disease') on grapevines (e.g. *B. obtusa*); *Botrytis cinerea* (teleomorph: *Botryotinia fuckeliana*: gray mold, gray rot) on soft fruit and pomaceous fruit (inter alia strawberries), vegetables (inter alia lettuce, carrots, celeriac and cabbage), oilseed rape, flowers, grapevines, forest crops and wheat (ear mold); *Bremia lactucae* (downy mildew) on lettuce; *Ceratocystis* (syn. *Ophiostoma*) spp. (blue stain fungus) on deciduous trees and coniferous trees, e.g. *C. ulmi* (Dutch elm disease) on elms; *Cercospora* spp. (*Cereospora* leaf spot) on corn (e.g. *C. zeae-maydis*), rice, sugar beet (e.g. *C. beticola*), sugar cane, vegetables, coffee, soybeans (e.g. *C. sojina* or *C. kikuchi*) and rice; *Cladosporium* spp. on tomato (e.g. *C. fulvum*: tomato leaf mold) and cereals, e.g. *C. herbarum* (ear rot) on wheat; *Claviceps purpurea* (ergot) on cereals; *Cochliobolus* (anamorph: *Helminthosporium* or *Bipolaris*) spp. (leaf spot) on corn (e.g. *C. carbonum*), cereals (e.g. *C. sativus*, anamorph: *B. sorokiniana*: glume blotch) and rice (tor example *C. miyabeanus*, anamorph: *H. oryzae*); *Colletotrichum*(teleomorph: *Glomerella*) spp. (anthracnosis) on cotton (e.g. *C. gossypii*), corn (e.g. *C. graminicola*: stem rot and anthracnosis), soft fruit, potatoes (e.g. *C. coccodes*: wilt disease), beans (e.g. *C. lindemuthianum*) and soybeans (e.g. *C. truncatum*); *Corticium* spp., e.g. *C. sasakii* (sheath blight) on rice; *Corynespora cassiicola* (leaf spot) on soybeans and ornamental plants; *Cycloconium* spp., e.g. *C. oleaginum* on olives; *Cylindrocarpon* spp. (e.g. fruit tree cancer or black foot disease of grapevine, teleomorph: *Nectria* or *Neonectria* spp.) on fruit trees, grapevines (e.g. *C. liriodendron*; teleomorph: *Neonectria liriodendri*, black foot disease) and many ornamental trees; *Dematophora* (teleomorph: *Rosellinia*) *necatrix*(root/stem rot) on soybeans; *Diaporthe* spp. *D. phaseolorum* (stem disease) on soybeans; *Drechslera* (syn. *Helminthosporium*, teleomorph: *Pyrenophora*) spp. on corn, cereals, such as barley (e.g. *D. teres*, net blotch) and on wheat (e.g. *D. tritici-repentis*: DTR leaf spot), rice and lawn; Esca disease (dieback of grapevine, apoplexia) on grapevines, caused by *Formitiporia* (syn. *Phellinus*) *punctata*, *F mediterranea*, *Phaeomoniella chlamydospora* (old name *Phaeoacremonium chlamydosporum*), *Phaeoacremonium aleophilum* and/or *Botryosphaeria obtusa*; *Elsinoe* spp. on pome fruit (*E. pyri*) and soft fruit (*E. veneta*: anthracnosis) and also grapevines (*E. ampelina*: anthracnosis); *Entyloma oryzae* (leaf smut) on rice; *Epicoccum* spp. (black head) on wheat; *Erysiphe* spp. (powdery mildew) on sugar beet (*E. betae*), vegetables (e.g. *E. pisi*), such as cucumber species (e.g. *E. cichoracearum*) and cabbage species, such as oilseed rape (e.g. *E. cruciferarum*); *Eutypa fata* (*Eutypa* cancer or dieback, anamorph: Cytosporina *lata*, syn. *Libertella blepharis*) on fruit trees, grapevines and many ornamental trees; *Exserohilum* (syn. *Helminthosporium*) spp. on corn (e.g. *E. turcicum*); *Fusarium* (teleomorph: *Gibberella*) spp. (wilt disease, root and stem rot) on various plants, such as e.g. *F. graminearum* or *F. culmorum* (root rot and silver-top) on cereals (e.g. wheat or barley), *F. oxysporum* on tomatoes, *F. solani* on soybeans and *F. verticillioides* on corn; *Gaeumannomyces graminis* (takeall) on cereals (e.g. wheat or barley) and corn; *Gibberella* spp. on cereals (e.g. *G. zeae*) and rice (e.g. *G. fujikuroi*: bakanae disease); *Glomerella cingulata* on grapevines, pomaceous fruit and other plants and *G. gossypii* on cotton; grainstaining complex on rice; *Guignardia bidwellii* (black rot) on grapevines; *Gymnosporangium* spp. on *Rosaceae* and juniper, e.g. *G. sabinae* (pear rust) on pears; *Helminthosporium* spp. (syn. *Drechslera*, teleomorph: *Cochliobolus*) on corn, cereals and rice; *Hemileia* spp., e.g. *H. vastatrix* (coffee leaf rust) on coffee; *Isariopsis clavispora* (syn. *Cladosporium vitis*) on grapevines; *Macrophomina phaseolina* (syn. *phaseoli*) (root/stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, *M. fructicola* and *M. fructigena* (blossom and twig blight) on stone fruit and other *Rosaceae*; *Mycosphaerella* spp. on cereals, bananas, soft fruit and peanuts, such as e.g. *M. graminicola* (anamorph: *Septoria tritici*, *Septoria* leaf blotch) on wheat or *M. fijiensis* (Sigatoka disease) on bananas; *Peronospora* spp. (downy mildew) on cabbage (e.g. *P. brassicae*), oilseed rape (e.g. *P. parasitica*), bulbous plants (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on grapevines (e.g. *P. tracheiphila* and *P. tetraspora*) and soybeans (e.g. *P. gregata*: stem disease); *Phoma lingam* (root and stem rot) on oilseed rape and cabbage and *P. betae* (leaf spot) on sugar beet; *Phomopsis* spp. on sunflowers, grapevines (e.g. *P. viticola*: dead-arm disease) and soybeans (e.g. stem canker/stem blight: *P. phaseoli*, teleomorph: *Diaporthe phaseolorum*); *Physoderma maydis* (brown spot) on corn; *Phytophthora* spp. (wilt disease, root, leaf, stem and fruit rot) on various plants, such as on bell peppers and cucumber species (e.g. *P. capsici*), soybeans (e.g. *P. megasperma*, syn. *P. sojae*), potatoes and tomatoes (e.g. *P. infestans*. late blight and brown rot) and deciduous trees (e.g. *P. ramorum* sudden oak death); *Plasmodiophora brassicae* (club-root) on cabbage, oilseed rape, radish and other plants; *Plasmopara* spp., e.g. *P. viticola* (*peronospora* of grapevines, downy mildew) on grapevines and *P. halstedii* on sunflowers; *Podosphaera* spp. (powdery mildew) on *Rosaceae*, hops, pomaceaus fruit and soft fruit, e.g. *P. leucotricha* on apple; *Polymyxa* spp., e.g. on cereals, such as barley and wheat (*P. graminis*) and sugar beet (*P. betae*) and the viral diseases transmitted thereby; Pseudocercosporella herpotrichoides (eyespot/stem break, teleomorph: *Tapesia yallundae*) on cereals. e.g. wheat or barley; *Pseudoperonospora* (downy mildew) on various plants, e.g. *P. cubensis* on cucumber species or *P. humili* on hops; *Pseudopezicula tracheiphila* (angular leaf scorch, anamorph *Phialophora*) on grapevines; *Puccinia* spp. (rust disease) on various plants, e.g. *P. triticina* (brown rust of wheat), *P. striiformis* (yellow rust). *P. hordei* (dwarf leaf rust), *P. graminis* (black rust) or *P. recondita* (brown rust of rye) on cereals, such as e.g. wheat, barley or rye. *P. kuehnii* on sugar cane and, e.g., on asparagus (e.g. *P. asparagi*); *Pyrenophora* (anamorph: *Drechslera*) *nitici-repentis* (speckled leaf blotch) on wheat or *P. teres* (net blotch) on barley; *Pyricularia* spp., e.g. *P. oryzae* (teleomorph: *Magnaporthe grisea*. rice blast) on rice and *P. grisea* on lawn and cereals; *Pythium* spp. (damping-off disease) on lawn, rice, corn, wheat, cotton, oilseed rape, sunflowers, sugar beet, vegetables and other plants (e.g. *P. ultimum* or *P. aphanidermatum*); *Ramularia* spp., e.g. *R. collo-cygni*(*Ramularia* leaf and lawn spot/physiological leaf spot) on barley and *R. beticola* on sugar beet; *Rhizoctonia* spp. on cotton, rice, potatoes, lawn, corn, oilseed rape, potatoes, sugar beet, vegetables and on various other plants, for example *R. solani* (root and stem rot) on soybeans, *R. solani* (sheath blight) on rice or *R. cerealis* (sharp eyespot) on wheat or barley; *Rhizopus stolonifer* (soft rot) on strawberries, carrots, cabbage, grapevines and tomato; *Rhynchosporium secalis* (leaf spot) on barley, rye and triticale; *Sarocladium oryzae* and *S. attenuatum* (sheath rot) on rice; *Sclerotinia* spp. (stem or white rot) on vegetable and field crops, such as oilseed rape, sunflowers (e.g. *Sclerotinia sclerotiorum*) and soybeans (e.g. *S. rolfsii*); *Septoria* spp. on various plants, e.g. *S. glycines* (leaf spot) on soybeans, *S. tritici* (*Septoria* leaf blotch) on wheat and S. (syn. *Stagonospora*) *nodorum* (leaf blotch and glume blotch) on cereals; *Uncinula* (syn. *Erysiphe*) *necator* (powdery mildew, anamorph: *Oidium tuckeri*) on grapevines; Setospaeria spp. (leaf spot) on corn (e.g. *S. turcicum*, syn. *Helminthosporium turcicum*) and lawn; *Sphacelotheca* spp. (head smut) on corn, (e.g. *S. reiliana*: kernel smut), millet and sugar cane; *Sphaerotheca fuliginea* (powdery mildew) on cucumber species; *Spongospora subterranea* (powdery scab) on potatoes and the viral diseases transmitted thereby; *Stagonospora* spp. on cereals, e.g. *S. nodorum* (leaf blotch and glume blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (curly-leaf disease) on peach and *T. pruni* (plum-pocket disease) on pi ums; *Thielaviopsis* spp. (black root rot) on tobacco, pome fruit, vegetable crops, soybeans and cotton, e.g. *T. basicola* (syn. *Chalara elegans*); *Tilletia* spp. (bunt or stinking smut) on cereals, such as e.g. *T. tritici* (syn. *T. caries*, wheat bunt) and *T. controversa* (dwarf bunt) on wheat; *Typhula incarnata* (gray snow mold) on barley or wheat; *Urocystis* spp., e.g. *U. occulta* (flag smut) on rye; *Uromyces* spp. (rust) on vegetable plants, such as beans (e.g. *U. appendiculatus*, syn. *U. phaseoli*) and sugar beet (e.g. *U. betae*); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears and *Verticillium* spp. (leaf and shoot wilt) on various plants, such as fruit trees and ornamental trees, grapevines, soft fruit, vegetable and field crops, such as e.g. *V. dahliae* on strawberries, oilseed rape, potatoes and tomatoes.

In particular, the compositions and/or formulations according to the invention are most suitable for controlling the following plant diseases: *Alternaria* spp. (black spot disease, black blotch) on vegetables, oilseed rape (e.g. *A.*

*brassicola* or *A. brassicae*), sugar beet (e.g. *A. tenuis*), fruit, rice, soybeans and also on potatoes (e.g. *A. solani* or *A. alternata*) and tomatoes (e.g. *A. solani* or *A. alternata*) and *Alternaria* spp. (black head) on wheat; *Aphanomyces* spp. on sugar beet and vegetables; *Ascochyta* spp. on vegetables, *Botryosphaeria* spp. ('Slack Dead Arm Disease') on grapevines (e.g. *B. obtusa*); *Botrytis cinerea* (teleomorph: *Botryotinia fuckeliana*: gray mold, gray rot) on soft fruit and pomaceous fruit (inter alia strawberries), vegetables (inter alia lettuce, carrots, celeriac and cabbage), oilseed rape, flowers and grapevines; *Cercospora* spp. (*Cereospora* leat spot) on vegetables and coffee; *Cladosporium* spp. on tomato (e.g. *C. fulvum*: tomato leaf mold) *Colletotrichum* (teleomorph: *Glomerella*) spp. (anthracnosis) on soft fruit, potatoes (e.g. *C. coccodes*: wilt disease) and beans (e.g. *C. lindemuthianum*); *Cycloconium* spp., e.g. *C. oleaginum* on olives; *Cylindrocarpon* spp. (e.g. fruit tree cancer or black foot disease of grapevine, teleomorph: *Nectria* or *Neonectria* spp.) on fruit trees, grapevines (e.g. *C. liriodendron*; teleomorph: *Neonectria liriodendri*, black foot disease) and many ornamental trees; Esca disease (dieback of grapevine, apoplexia) on grapevines, caused by *Formitiporia* (syn. *Phellinus*) *punctata*, *F mediterranea*, *Phaeomoniella chlamydospora* (old name *Phaeoacremonium chlamydosporum*), *Phaeoacremonium aleophilum* and/or *Botryosphaeria obtusa*; *Elsinoe* spp. on pome fruit (*E. pyri*) and soft fruit (*E. veneta*: anthracnosis) and also grapevines (*E. ampelina*: anthracnosis); *Epicoccum* spp. (black head) on vegetables (e.g. *E. pisi*), such as cucumber species (e.g. *E. cichoracearum*) and cabbage species, such as oilseed rape (e.g. *E. cruciferarum*); *Eutypa fata* (*Eutypa* cancer or dieback, anamorph: *Cytosporina lata*, syn. *Libertella blepharis*) on fruit trees, grapevines and many ornamental trees; *Fusarium* (teleomorph: *Gibberella*) spp. (wilt disease, root and stem rot) on various plants, such as *F. oxysporum* on tomatoes; *Glomerella cingulata* on grapevines, pomaceous fruit and other plants; *Guignardia bidwellii* (black rot) on grapevines; *Gymnosporangium* spp. on *Rosaceae* and juniper, e.g. *G. sabinae* (pear rust) on pears; *Hemileia* spp., e.g. *H. vastatrix* (coffee leaf rust) on coffee; *Isariopsis clavispora* (syn. *Cladosporium vitis*) on grapevines; *Marssonia* species on various crops, e.g. *Marssonia coronaria* on apple; *Monilinia* spp., e.g. *M. laxa*, *M. fructicola* and *M. fructigena* (blossom and twig blight) on stone fruit and other *Rosaceae*; *Mycosphaerella* spp. on bananas, soft fruit and peanuts, such as *M. fijiensis* (Sigatoka disease) on bananas; *Peronospora* spp. (downy mildew) on cabbage (e.g. *P. brassicae*), oilseed rape (e.g. *P. parasitica*), bulbous plants (e.g. *P. destructor*), tobacco (*P. tabacina*); *Phialophora* spp. e.g. on grapevines (e.g. *P. tracheiphila* and *P. tetraspora*); *Phoma lingam* (root and stem rot) on oilseed rape and cabbage and *P. betae* (leaf spot) on sugar beet; *Phomopsis* spp. on sunflowers, grapevines (e.g. *P. viticola*: dead-arm disease); *Plasmodiophora brassicae* (club-root) on cabbage, oilseed rape, radish and other plants; *Plasmopara* spp., e.g. *P. viticola* (*peronospora* of grapevines, downy mildew) on grapevines; *Podosphaera* spp. (powdery mildew) on *Rosaceae*, hops, pomaceaus fruit and soft fruit, e.g. *P. leucotricha* on apple; *Pseudoperonospora* (downy mildew) on various plants, e.g. *P. cubensis* on cucumber species or *P. humili* on hops; *Pseudopezicula tracheiphila* (angular leaf scorch, anamorph *Phialophora*) on grapevines; *Puccinia* spp. (rust disease) on various plants, *Rhizoctonia* spp. on potatoes, oilseed rape, potatoes, sugar beet, vegetables and on various other plants; *Rhizopus stolonifer* (soft rot) on strawberries, carrots, cabbage, grapevines and tomato; *Sclerotinia* spp. (stem or white rot) on vegetable and field crops, such as oilseed rape, sunflowers (e.g. *Sclerotinia sclerotiorum*) and soybeans (e.g. *S. rolfsii*), *Septoria* spp. on various plants; *Uncinula* (syn. *Erysiphe*) necator (powdery mildew, anamorph: *Oidium tuckeri*) on grapevines; *Sphaerotheca fuliginea* (powdery mildew) on cucumber species; *Spongospora subterranea* (powdery scab) on potatoes and the viral diseases transmitted thereby; *Synchytrium endobioticum* on potatoes (potato wart disease); *Taphrina* spp., e.g. *T. deformans* (curly-leaf disease) on peach and *T. pruni* (plum-pocket disease) on pi ums; *Thielaviopsis* spp. (black root rot) on tobacco, pome fruit and vegetable crops; *Uromyces* spp. (rust) on vegetable plants, such as beans (e.g. *U. appendiculatus*, syn. *U. phaseoll*) and sugar beet (e.g. *U. betae*); *Venturia* spp. (scab) on apples (e.g. *V. inaequalis*) and pears and *Verticillium* spp. (leaf and shoot wilt) on various plants, such as fruit trees and ornamental trees, grapevines, soft fruit, vegetable and field crops, such as e.g. *V. dahliae* on strawberries, oilseed rape, potatoes and tomatoes.

Plant Growth Regulation

In some cases, the compositions and/or formulations according to the invention can, at particular concentrations or application rates, also be used as herbicides, safeners, growth regulators or agents to improve plant properties, or as microbicides, for example as fungicides, antimycotics, bactericides, viricides (including compositions and/or formulations against viroids) or as compositions and/or formulations against MLO (*Mycoplasma*-like organisms) and RLO (*Rickettsia*-like organisms). The active ingredients of the composition and/or formulation according to the invention intervene in the metabolism of the plants and can therefore also be used as growth regulators.

Plant growth regulators may exert various effects on plants. The effect of the substances depends essentially on the time of application in relation to the developmental stage of the plant, and also on the amounts of active ingredient applied to the plants or their environment and on the type of application. In each case, growth regulators should have a particular desired effect on the crop plants.

Plant growth-regulating compounds can be used, for example, to inhibit the vegetative growth of the plants. Such inhibition of growth is of economic interest, for example, in the case of grasses, since it is thus possible to reduce the frequency of grass cutting in ornamental gardens, parks and sport facilities, on roadsides, at airports or in fruit crops. Also of significance is the inhibition of the growth of herbaceous and woody plants on roadsides and in the vicinity of pipelines or overhead cables, or quite generally in areas where vigorous plant growth is unwanted.

Also important is the use of growth regulators for inhibition of the longitudinal growth of cereal. This reduces or completely eliminates the risk of lodging of the plants prior to harvest. In addition, growth regulators in the case of cereals can strengthen the culm, which also counteracts lodging. The employment of growth regulators for shortening and strengthening culms allows the deployment of higher fertilizer volumes to increase the yield, without any risk of lodging of the cereal crop.

In many crop plants, inhibition of vegetative growth allows denser planting, and it is thus possible to achieve higher yields based on the soil surface. Another advantage of the smaller plants obtained in this way is that the crop is easier to cultivate and harvest.

Inhibition of the vegetative plant growth may also lead to enhanced yields because the nutrients and assimilates are of more benefit to flower and fruit formation than to the vegetative parts of the plants.

Frequently, growth regulators can also be used to promote vegetative growth. This is of great benefit when harvesting the vegetative plant parts. However, promoting vegetative growth may also promote generative growth in that more assimilates are formed, resulting in more or larger fruits.

In some cases, yield increases may be achieved by manipulating the metabolism of the plant, without any detectable changes in vegetative growth. In addition, growth regulators can be used to alter the composition of the plants, which in turn may result in an improvement in quality of the harvested products. For example, it is possible to increase the sugar content in sugar beet, sugar cane, pineapples and in citrus fruit, or to increase the protein content in soya or cereals. It is also possible, for example, to use growth regulators to inhibit the degradation of desirable ingredients, for example sugar in sugar beet or sugar cane, before or after harvest. It is also possible to positively influence the production or the elimination of secondary plant ingredients. One example is the stimulation of the flow of latex in rubber trees.

Under the influence of growth regulators, parthenocarpic fruits may be formed. In addition, it is possible to influence the sex of the flowers. It is also possible to produce sterile pollen, which is of great importance in the breeding and production of hybrid seed.

Use of growth regulators can control the branching of the plants. On the one hand, by breaking apical dominance, it is possible to promote the development of side shoots, which may be highly desirable particularly in the cultivation of ornamental plants, also in combination with an inhibition of growth. On the other hand, however, it is also possible to inhibit the growth of the side shoots. This effect is of particular interest, for example, in the cultivation of tobacco or in the cultivation of tomatoes.

Under the influence of growth regulators, the amount of leaves on the plants can be controlled such that defoliation of the plants is achieved at a desired time. Such defoliation plays a major role in the mechanical harvesting of cotton, but is also of interest for facilitating harvesting in other crops, for example in viticulture. Defoliation of the plants can also be undertaken to lower the transpiration of the plants before they are transplanted.

Growth regulators can likewise be used to regulate fruit dehiscence. On the one hand, it is possible to prevent premature fruit dehiscence. On the other hand, it is also possible to promote fruit dehiscence or even flower abortion to achieve a desired mass ("thinning"), in order to eliminate alternation. Alternation is understood to mean the characteristic of some fruit species, for endogenous reasons, to deliver very different yields from year to year. Finally, it is possible to use growth regulators at the time of harvest to reduce the forces required to detach the fruits, in order to allow mechanical harvesting or to facilitate manual harvesting.

Growth regulators can also be used to achieve faster or else delayed ripening of the harvested material before or after harvest. This is particularly advantageous as it allows optimal adjustment to the requirements of the market. Moreover, growth regulators in some cases can improve the fruit colour. hi addition, growth regulators can also be used to concentrate maturation within a certain period of time. This establishes the prerequisites for complete mechanical or manual harvesting in a single operation, for example in the case of tobacco, tomatoes or coffee.

By using growth regulators, it is additionally possible to influence the resting of seed or buds of the plants, such that plants such as pineapple or ornamental plants in nurseries, for example, germinate, sprout or flower at a time when they are normally not inclined to do so. In areas where there is a risk of frost, it may be desirable to delay budding or germination of seeds with the aid of growth regulators, in order to avoid damage resulting from late frosts.

Finally, growth regulators can induce resistance of the plants to frost, drought or high salinity of the soil. This allows the cultivation of plants in regions which are normally unsuitable for this purpose.

Resistance Induction/Plant Health and Other Effects

The compositions and/or formulations according to the invention also exhibit a potent strengthening effect in plants. Accordingly, they can be used for mobilizing the defences of the plant against attack by undesirable microorganisms.

Plant-strengthening (resistance-inducing) substances are to be understood as meaning, in the present context, those substances which are capable of stimulating the defence system of plants in such a way that the treated plants, when subsequently inoculated with undesirable microorganisms, develop a high degree of resistance to these microorganisms.

The active compounds according to the invention are also suitable for increasing the yield of crops. In addition, they show reduced toxicity and are well tolerated by plants.

Further, in context with the present invention plant physiology effects comprise the following:

Abiotic stress tolerance, comprising temperature tolerance, drought tolerance and recovery after drought stress, water use efficiency (correlating to reduced water consumption), flood tolerance, ozone stress and UV tolerance, tolerance towards chemicals like heavy metals, salts, pesticides (safener) etc.

Biotic stress tolerance, comprising increased fungal resistance and increased resistance against nematodes, viruses and bacteria. In context with the present invention, biotic stress tolerance preferably comprises increased fungal resistance and increased resistance against nematodes Increased plant vigor, comprising plant health/plant quality and seed vigor, reduced stand failure, improved appearance, increased recovery, improved greening effect and improved photosynthetic efficiency.

Effects on plant hormones and/or functional enzymes.

Effects on growth regulators (promoters), comprising earlier germination, better emergence, more developed root system and/or improved root growth, increased ability of tillering, more productive tillers, earlier flowering, increased plant height and/or biomass, shorting of stems, improvements in shoot growth, number of kernels/ear, number of ears/m$^2$, number of stolons and/or number of flowers, enhanced harvest index, bigger leaves, less dead basal leaves, improved phyllotaxy, earlier maturation/earlier fruit finish, homogenous riping, increased duration of grain filling, better fruit finish, bigger fruit/vegetable size, sprouting resistance and reduced lodging.

Increased yield, referring to total biomass per hectare, yield per hectare, kernel/fruit weight, seed size and/or hectoliter weight as well as to increased product quality, comprising:

improved processability relating to size distribution (kernel, fruit, etc.), homogenous riping, grain moisture, better milling, better vinification, better brewing, increased juice yield, harvestability, digestibility, sedimentation value, falling number, pod stability, storage stability, improved fiber length/strength/uniformity, increase of milk and/or meet quality of silage fed animals, adaption to cooking and frying; further comprising improved marketability relating to improved fruit/grain quality, size distribution (kernel, fruit, etc.), increased storage/shelf-life, firmness/softness, taste (aroma, texture, etc.), grade (size, shape, number of berries, etc.), number of berries/fruits per bunch, crispness, freshness, coverage with wax, frequency of physiological disorders, colour, etc.;

further comprising increased desired ingredients such as e.g. protein content, fatty acids, oil content, oil quality, aminoacid composition, sugar content, acid content (pH), sugar/acid ratio (Brix), polyphenols, starch content, nutritional quality, gluten content/index, energy content, taste, etc.;

and further comprising decreased undesired ingredients such as e.g. less mycotoxines, less aflatoxines, geosmin level, phenolic aromas, lacchase, polyphenol oxidases and peroxidases, nitrate content etc.

Sustainable agriculture, comprising nutrient use efficiency, especially nitrogen (N)-use efficiency, phosphorus (P)-use efficiency, water use efficiency, improved transpiration, respiration and/or $CO_2$ assimilation rate, better nodulation, improved Ca-metabolism etc.

Delayed senescence, comprising improvement of plant physiology which is manifested, for example, in a longer grain filling phase, leading to higher yield, a longer duration of green leaf colouration of the plant and thus comprising colour (greening), water content, dryness etc. Accordingly, in the context of the present invention, it has been found that the specific inventive application of the compositions and/or formulations according to the invention makes it possible to prolong the green leaf area duration, which delays the maturation (senescence) of the plant. The main advantage to the farmer is a longer grain filling phase leading to higher yield. There is also an advantage to the farmer on the basis of greater flexibility in the harvesting time.

Therein "sedimentation value" is a measure for protein quality and describes according to Zeleny (Zeleny value) the degree of sedimentation of flour suspended in a lactic acid solution during a standard time interval. This is taken as a measure of the baking quality. Swelling of the gluten fraction of flour in lactic acid solution affects the rate of sedimentation of a flour suspension. Both a higher gluten content and a better gluten quality give rise to slower sedimentation and higher Zeleny test values. The sedimentation value of flour depends on the wheat protein composition and is mostly correlated to the protein content, the wheat hardness, and the volume of pan and hearth loaves. A stronger correlation between loaf volume and Zeleny sedimentation volume compared to SDS sedimentation volume could be due to the protein content influencing both the volume and Zeleny value (*Czech J. Food Sci. Vol.* 21, No. 3: 91-96, 2000).

Further the "falling number" as mentioned herein is a measure for the baking quality of cereals, especially of wheat. The falling number test indicates that sprout damage may have occurred. It means that changes to the physical properties of the starch portion of the wheat kernel has already happened. Therein, the falling number instrument analyzes viscosity by measuring the resistance of a flour and water paste to a falling plunger. The time (in seconds) for this to happen is known as the falling number. The falling number results are recorded as an index of enzyme activity in a wheat or flour sample and results are expressed in time as seconds. A high falling number (for example, above 300 seconds) indicates minimal enzyme activity and sound quality wheat or flour. A low falling number (for example, below 250 seconds) indicates substantial enzyme activity and sprout-damaged wheat or flour.

The term "more developed root system"/"improved root growth" refers to longer root system, deeper root growth, faster root growth, higher root dry/fresh weight, higher root volume, larger root surface area, bigger root diameter, higher root stability, more root branching, higher number of root hairs, and/or more root tips and can be measured by analyzing the root architecture with suitable methodologies and Image analysis programmes (e.g. WinRhizo).

The term "crop water use efficiency" refers technically to the mass of agriculture produce per unit water consumed and economically to the value of product(s) produced per unit water volume consumed and can e.g. be measured in terms of yield per ha, biomass of the plants, thousand-kernel mass, and the number of ears per m2.

The term "nitrogen-use efficiency" refers technically to the mass of agriculture produce per unit nitrogen consumed and economically to the value of product(s) produced per unit nitrogen consumed, reflecting uptake and utilization efficiency.

Improvement in greening/improved colour and improved photosynthetic efficiency as well as the delay of senescence can be measured with well-known techniques such as a HandyPea system (Hansatech). Fv/Fm is a parameter widely used to indicate the maximum quantum efficiency of photosystem II (PSII). This parameter is widely considered to be a selective indication of plant photosynthetic performance with healthy samples typically achieving a maximum Fv/Fm value of approx. 0.85. Values lower than this will be observed if a sample has been exposed to some type of biotic or abiotic stress factor which has reduced the capacity for photochemical quenching of energy within PSII. Fv/Fm is presented as a ratio of variable fluorescence (Fv) over the maximum fluorescence value (Fm). The Performance Index is essentially an indicator of sample vitality. (See e.g. *Advanced Techniques in Soil Microbiology,* 2007, 11, 319-341; *Applied Soil Ecology,* 2000, 15, 169-182.)

The improvement in greening/improved colour and improved photosynthetic efficiency as well as the delay of senescence can also be assessed by measurement of the net photosynthetic rate (Pn), measurement of the chlorophyll content, e.g. by the pigment extraction method of Ziegler and Ehle, measurement of the photochemical efficiency (Fv/Fm ratio), determination of shoot growth and final root and/or canopy biomass, determination of tiller density as well as of root mortality.

Within the context of the present invention preference is given to improving plant physiology effects which are selected from the group comprising: enhanced root growth/more developed root system, improved greening, improved water use efficiency (correlating to reduced water consumption), improved nutrient use efficiency, comprising especially improved nitrogen (N)-use efficiency, delayed senescence and enhanced yield.

Within the enhancement of yield preference is given as to an improvement in the sedimentation value and the falling number as well as to the improvement of the protein and sugar content—especially with plants selected from the group of cereals (preferably wheat).

Preferably the novel use of the fungicidal compositions and/or formulations of the present invention relates to a combined use of a) preventively and/or curatively controlling pathogenic fungi, with or without resistance management, and b) at least one of enhanced root growth, improved greening, improved water use efficiency, delayed senescence and enhanced yield. From group b) enhancement of root system, water use efficiency and N-use efficiency is particularly preferred.

Mycotoxins

In addition, the inventive treatment can reduce the mycotoxin content in the harvested material and the foods and feeds prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *F. acuminatum, F. asiaticum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudo graminearum, F. sambucinum, F. scirpi, F. semitectum, F. solani, F. sporotrichoides, F. langsethiae, F. subglutinans, F. tricinctum, F. verticillioides* etc., and also by *Aspergillus* spec., such as *A. flavus, A. parasiticus, A. nomius, A. ochraceus, A. clavatus, A. terreus, A. versicolor, Penicillium* spec., such as *P. verrucosum, P. viridicatum, P. citrinum, P. expansum, P. claviforme, P. roqueforti, Claviceps* spec., such as *C. purpurea, C. fusiformis, C. paspali, C. africana, Stachybotrys* spec. and others.

Material Protection

The compositions and/or formulations according to the invention can also be used in the protection of materials, for protection of industrial materials against attack and destruction by phytopathogenic fungi.

In addition, the compositions and/or formulations according to the invention can be used as antifouling compositions and/or formulations, alone or in combinations with other active ingredients.

Industrial materials in the present context are understood to mean inanimate materials which have been prepared for use in industry. For example, industrial materials which are to be protected by compositions and/or formulations according to the invention from microbial alteration or destruction may be adhesives, glues, paper, wallpaper and board/cardboard, textiles, carpets, leather, wood, fibers and tissues, paints and plastic articles, cooling lubricants and other materials which can be infected with or destroyed by microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials within the scope of the present invention preferably include adhesives, sizes, paper and card, leather, wood, paints, cooling lubricants and heat transfer fluids, more preferably wood.

The compositions and/or formulations according to the invention may prevent adverse effects, such as rotting, decay, discoloration, decoloration or formation of mould.

In the case of treatment of wood the compositions and/or formulations according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting a composition and/or formulation according to the invention; this includes for example direct application, spraying, dipping, injection or any other suitable means.

In addition, the compositions and/or formulations according to the invention can be used to protect objects which come into contact with saltwater or brackish water, especially hulls, screens, nets, buildings, moorings and signalling systems, from fouling.

The inventive method for controlling phytopathogenic fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The compositions and/or formulations according to the invention may prevent adverse effects, such as rotting, decay, discoloration, decoloration or formation of mould.

Microorganisms capable of degrading or altering the industrial materials include, for example, bacteria, fungi, yeasts, algae and slime organisms. The compositions and/or formulations according to the invention preferably act against fungi, especially moulds, wood-discoloring and wood-destroying fungi (Ascomycetes, Basidiomycetes, Deuteromycetes and Zygomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Ophiostoma* spp., *Ceratocystis* spp., *Humicola* spp., *Petriella* spp., *Trichurus* spp., *Coriolus* spp., *Gloeophyllum* spp., *Pleurotus* spp., *Poria* spp., *Serpula* spp. and *Tyromyces* spp., *Cladosporium* spp., *Paecilomyces* spp. *Mucor* spp., *Escherichia*, such as *Escherichia coli*; *Pseudomonas*, such as *Pseudomonas aeruginosa*; *Staphylococcus*, such as *Staphylococcus aureus*, *Candida* spp. and *Saccharomyces* spp., such as *Saccharomyces cerevisae*.

The advanced fungicidal activity of the compositions and/or formulations according to the invention is evident from the examples below. While the individual active compounds exhibit weaknesses with regard to the fungicidal activity, the combinations have an activity which exceeds a simple addition of activities.

A synergistic effect of fungicides is always present when the fungicidal activity of the compositions and/or formulations exceeds the total of the activities of the active compounds when applied individually. The expected activity for a given combination of two active compounds can be calculated as follows (cf. Colby, S. R., "Calculating Synergistic and Antagonistic Responses of Herbicide Combinations", *Weeds* 1967, 15, 20-22):

If

X is the efficacy when active compound A is applied at an application rate of m ppm (or g/ha), Y is the efficacy when active compound B is applied at an application rate of n ppm (or g/ha), E is the efficacy when the active compounds A and B are applied at application rates of m and n ppm (or g/ha), respectively, and then $$E = X + Y - \frac{X \cdot Y}{100}$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in Neth. J. Plant Path., 1964, 70, 73-80).

The invention is illustrated by the following examples. However the invention is not limited to the examples.

Example A

Alternaria Test (Tomatoes)/Preventive

Biological control agents and diverse chemical active compounds were tested solo and in a mixture of both. The biological control agents SERENADE® DPZ (comprising the biological control agent B1.1.18, Bacillus subtilis, strain AQ30002, Accession No. NRRL B-50421), SERENADE® ASO (comprising the biological control agent B1.1.1, Bacillus subtilis, strain QST713/AQ713, Accession No. NRRL B-21661) and SONATA® (comprising the biological control agent B1.1.6, Bacillus pumilus, strain QST2808, Accession No. NRRL B-30087) were diluted with water to the desired application rate of 100 ppm a.i. to 500 ppm a.i., referring to the amount of 1.34% Bacillus subtilis or 1.38% Bacillus pumilis product.

The chemical compounds were solved in acetone+dimethylacetamide in a ratio of 1/1+2% PS 16 (Alkylarylpolyglykolether) and diluted with water or the prepared bacteria suspension. Chemical compounds were tested in the concentration of 80 ppm a.i.

In order to test the activity, young plants of tomatoes (21 d after sowing) were sprayed with the preparation of active compound at the stated rate of application. 24 h after application, the plants were inoculated with an aqueous spore suspension (7.500 spores/ml) of Alternaria solani. The wetted plants were then placed in an incubation cabinet at approximately 20° C. and a relative atmospheric humidity of 100% and darkness.

The test was evaluated 3 days after the inoculation. Assessment: % infested leaf. 0% efficacy corresponds to the level of disease in the untreated control while an efficacy of 100% means that no disease is observed.

The table below (Table A) clearly shows that the observed activity of the composition according to the invention is greater than the calculated activity, i.e. a synergistic effect is present.

TABLE A

| Active compound | Application rate of active compound in ppm a.i. | Efficacy in % Found* | Calc.** |
|---|---|---|---|
| B1.1.1 (Serenade ® ASO) | 100 | 2 | |
| | 200 | 43 | |

TABLE A-continued

| Active compound | Application rate of active compound in ppm a.i. | Efficacy in % Found* | Calc.** |
|---|---|---|---|
| B1.1.18 (Serenade ® DPZ) | 250 | 11 | |
| B1.1.6 (Sonata ®) | 250 | 31 | |
| | 500 | 38 | |
| (I-1) | 80 | 37 | |
| (I-3) | 80 | 37 | |
| (I-2) | 80 | 13 | |
| B1.1.1 (Serenade ® ASO) + (I-1) | 100 + 80 | 84 | 38 |
| B1.1.1 (Serenade ® ASO) + (I-1) | 200 + 80 | 90 | 64 |
| B1.1.1 (Serenade ® ASO) + (I-3) | 100 + 80 | 83 | 38 |
| B1.1.1 (Serenade ® ASO) + (I-3) | 200 + 80 | 94 | 64 |
| B1.1.1 (Serenade ® ASO) + (I-2) | 100 + 80 | 83 | 15 |
| B1.1.1 (Serenade ® ASO) + (I-2) | 200 + 80 | 89 | 50 |
| B1.1.18 (Serenade ® DPZ) + (I-1) | 250 + 80 | 92 | 44 |
| B1.1.18 (Serenade ® DPZ) + (I-3) | 250 + 80 | 80 | 44 |
| B1.1.18 (Serenade ® DPZ) + (I-2) | 250 + 80 | 69 | 23 |
| B1.1.6 (Sonata ®) + (I-1) | 500 + 80 | 76 | 61 |
| B1.1.6 (Sonata ®) + (I-3) | 500 + 80 | 80 | 61 |
| B1.1.6 (Sonata ®) + (I-2) | 500 + 80 | 90 | 46 |

*found = activity found
**calc. = activity calculated using Colby's formula

Example B

Sphaerotheca Test (Cucumbers)/Preventive

Biological control agents and diverse chemical active compounds were tested solo and in a mixture of both. The biological control agents SERENADE® DPZ (comprising the biological control agent B1.1.18, Bacillus subtilis, strain AQ30002, Accession No. NRRL B-50421), SERENADE ASO (comprising the biological control agent B1.1.1, Bacillus subtilis, strain QST713/AQ713, Accession No. NRRL B-21661) and SONATA® (comprising the biological control agent B1.1.6, Bacillus pumilus, strain QST2808, Accession No. NRRL B-30087) were diluted with water to the desired application rate of 100 ppm a.i. to 500 ppm a.i., referring to the amount of 1.34% Bacillus subtilis or 1.38% Bacillus pumilis product.

The chemical compounds were solved in acetone+dimethylacetamide in the ratio 1/1+2% PS 16 (Alkylarylpolyglykolether) and diluted with water or the prepared bacteria suspension. Chemical compounds were tested in the concentration of 80 ppm a.i.

In order to test the activity, young plants (kotyledones are fully developed) of cucumber c.v. "Delikatess" were sprayed with the undermentioned preparation of compounds at the stated time of application. 24 h after application, the plants were inoculated with an aqueous spore suspension of Sphaerotheca fuliginea. Infested plants were stored in greenhouse at 22° C. and 70% relative humidity.

The test was evaluated 7 d after inoculation. Assessment: % infested leaf. 0% efficacy corresponds to the level of disease in the untreated control while an efficacy of 100% means that no disease is observed.

The table below (Table B) clearly shows that the observed activity of the composition according to the invention is greater than the calculated activity, i.e. a synergistic effect is present.

TABLE B

| Active compound | Application rate of active compound in ppm a.i. | Efficacy in % Found* | Calc.** |
|---|---|---|---|
| B1.1.1 (Serenade ® ASO) | 100 | 60 | |
| | 200 | 92 | |
| B1.1.18 (Serenade ® DPZ) | 250 | 47 | |
| B1.1.6 (Sonata ®) | 250 | 56 | |
| | 500 | 49 | |
| (I-1) | 80 | 49 | |
| (I-3) | 80 | 32 | |
| (I-2) | 80 | 35 | |
| B1.1.1 (Serenade ® ASO) + (I-1) | 100 + 80 | 96 | 80 |
| B1.1.1 (Serenade ® ASO) + (I-1) | 200 + 80 | 98 | 96 |
| B1.1.1 (Serenade ® ASO) + (I-3) | 100 + 80 | 93 | 73 |
| B1.1.1 (Serenade ® ASO) + (I-3) | 200 + 80 | 98 | 95 |
| B1.1.1 (Serenade ® ASO) + (I-2) | 100 + 80 | 93 | 74 |
| B1.1.1 (Serenade ® ASO) + (I-2) | 200 + 80 | 98 | 95 |
| B1.1.18 (Serenade ® DPZ) + (I-1) | 250 + 80 | 91 | 73 |
| B1.1.18 (Serenade ® DPZ) + (I-3) | 250 + 80 | 74 | 64 |
| B1.1.18 (Serenade ® DPZ) + (I-2) | 250 + 80 | 87 | 65 |
| B1.1.6 (Sonata ®) + (I-1) | 500 + 80 | 87 | 74 |
| B1.1.6 (Sonata ®) + (I-3) | 500 + 80 | 80 | 66 |
| B1.1.6 (Sonata ®) + (I-2) | 500 + 80 | 86 | 67 |

*found = activity found
**calc. = activity calculated using Colby's formula

The invention claimed is:

1. A composition, comprising
(A) at least one compound of formula (I)

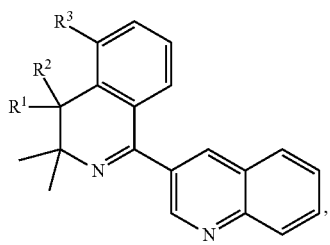

(I)

wherein
$R^1$ represents a methyl group or halogen and
$R^2$ represents a methyl group or halogen and
$R^3$ represents hydrogen or halogen and
(B) at least one biological control agent selected from B1.1.1 *Bacillus subtilis*, strain QST713/AQ713, Accession No. NRRL B-21661; B1.1.6 *Bacillus pumilus*, strain QST2808, Accession No. NRRL B-30087, and B1.1.18 *Bacillus subtilis* strain AQ30002, Accession No. NRRL B-50421.

2. A composition according to claim 1, whereby the compound of formula (I) is represented by one of the compounds (I-1) to (I-3):

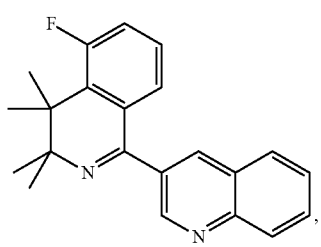

(I-1)

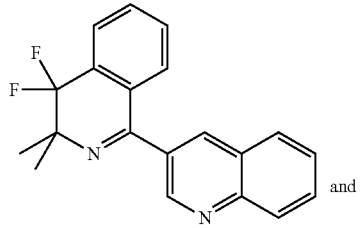

(I-2)

and

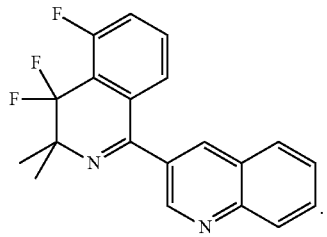

(I-3)

3. The composition according to claim 1, whereby the biological control agent (B) is B1.1.1 *Bacillus subtilis*, strain QST713/AQ713, Accession No. NRRL B-21661.

4. The composition according to claim 1, wherein said composition acts in a synergistic fashion.

5. The composition according to claim 1, whereby the biological control agent is B1.1.6 *Bacillus pumilus*, strain QST2808, Accession No. NRRL B-30087.

6. The composition according to claim 1, whereby the biological control agent is B1.1.18 *Bacillus subtilis* strain AQ30002, Accession No. NRRL B-50421.

7. An agricultural composition comprising a composition according to claim 1 and comprising at least one agriculturally suitable additive.

8. Method for preparing an agricultural composition comprising adding at least one agriculturally suitable additive to the composition according to claim 1.

9. Method for reducing damage of plants and plant parts or losses in harvested fruits or vegetables caused by phytopathogenic fungi by controlling such phytopathogenic fungi, comprising applying the composition according to claim 1 to the plant or the phytopathogenic fungi or the habitat of the plant or the habitat of the phytopathogenic fungi.

10. The method according to claim 9, wherein the plants are selected from the group consisting of fruit crops and vegetables.

11. The method of claim 9, wherein the plants are selected from the group consisting of canola, rapeseed, field mustard, oilpalm, coconut, nuts, grapes, vine, apples, pears, apricots, cherries, almonds, plums, peaches, strawberries, raspberries, red and black currant, gooseberry, *Ribesioidae* sp., *Juglandaceae* sp., *Betulaceae* sp., *Anacardiaceae* sp., *Fagaceae* sp., *Moraceae* sp., olive tree, avocado, cinnamon, camphor, banana trees, coffee, tea, *Sterculiceae* sp., lemons, oranges, mandarins, grapefruit, tomatoes, potatoes, peppers, *capsicum*, aubergines, tobacco, *Liliaceae* sp., lettuce, artichokes, chicory, root chicory, endive, common chicory, carrots, parsley, celery, celeriac, cucumbers, gherkins, pumpkins, watermelons, calabashes, melons, leeks, onions, white cabbage, red cabbage, broccoli, cauliflower, brussel sprouts, pak choi, kohlrabi, radishes, horseradish, cress, chinese cabbage, peanuts, peas, lentils, beans, common beans, broad beans, Swiss chard, fodder beet, spinach, beetroot, hemp, *cannabis*, okra, cocoa, poppy, asparagus, ornamental plants in the garden and woods, turf, lawn, grass and *Stevia rebaudiana*.

12. The method according to claim 9, wherein the plants are genetically modified.

13. The composition according to claim 1, wherein the only active components in the composition are the compound of formula (I) and the biological control agent.

14. The method according to claim 9, wherein the plants are tomato or cucumber plants.

15. The composition according to claim 2, wherein the biological control agent is B1.1.1 *Bacillus subtilis*, strain QST713/AQ713, Accession No. NRRL B-21661; and wherein the compound of formula (I) and the biological control agent are present in amounts to provide synergistic results.

16. The composition according to claim 2, wherein the biological control agent is B1.1.6 *Bacillus pumilus*, strain QST2808, Accession No. NRRL B-30087; and wherein the compound of formula (I) and the biological control agent are present in amounts to provide synergistic results.

17. The composition according to claim 2, wherein the biological control agent is B1.1.18 *Bacillus subtilis* strain AQ30002, Accession No. NRRL B-50421; and wherein the compound of formula (I) and the biological control agent are present in amounts to provide synergistic results.

18. The composition according to claim 15, wherein the only active components in the composition are the compound of formula (I) and the biological control agent.

19. The composition according to claim 16, wherein the only active components in the composition are the compound of formula (I) and the biological control agent.

20. The composition according to claim 17, wherein the only active components in the composition are the compound of formula (I) and the biological control agent.

* * * * *